(12) United States Patent
Mitre et al.

(10) Patent No.: US 10,441,642 B2
(45) Date of Patent: Oct. 15, 2019

(54) IMMUNOGENIC COMPOSITIONS AND VACCINES FOR PREVENTING OR TREATING FILARIAL DISEASE

(71) Applicants: The Henry M. Jackson Foundation for the Advancement of Military Medicine, Inc., Bethesda, MD (US); The United States Government, as Represented by the Secretary of the Department of Health and Human, Washington, DC (US)

(72) Inventors: Edward E. Mitre, Rockville, MD (US); Christopher Morris, North Potomac, MD (US); Sasisekhar Bennuru, Rockville, MD (US); Thomas Nutman, Chevy Chase, MD (US)

(73) Assignees: The Henry M. Jackson Foundation for the Advancement of Military Medicine, Inc., Bethesda, MD (US); The United States Government, as Represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 15/558,336

(22) PCT Filed: Mar. 17, 2016

(86) PCT No.: PCT/US2016/022787
§ 371 (c)(1),
(2) Date: Sep. 14, 2017

(87) PCT Pub. No.: WO2016/149460
PCT Pub. Date: Sep. 22, 2016

(65) Prior Publication Data
US 2018/0064791 A1 Mar. 8, 2018

Related U.S. Application Data

(60) Provisional application No. 62/135,115, filed on Mar. 18, 2015.

(51) Int. Cl.
| | |
|---|---|
| *A61K 38/16* | (2006.01) |
| *A61K 39/00* | (2006.01) |
| *A61K 38/17* | (2006.01) |
| *A61K 39/39* | (2006.01) |
| *C07K 14/435* | (2006.01) |
| *A61P 33/10* | (2006.01) |

(52) U.S. Cl.
CPC ...... *A61K 39/0003* (2013.01); *A61K 38/1767* (2013.01); *A61K 39/39* (2013.01); *A61P 33/10* (2018.01); *C07K 14/4354* (2013.01); *A61K 2039/55566* (2013.01)

(58) Field of Classification Search
None
See application file for complete search history.

(56) References Cited

U.S. PATENT DOCUMENTS

2003/0224007 A1 12/2003 Van Milligen et al.

FOREIGN PATENT DOCUMENTS

WO 98/40497 A2 9/1998

OTHER PUBLICATIONS

Arumugam et al (Parasites & Vectors (2014), 7, 43/1-43/7, 7 pp. 1756-3305).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
International Search Report and Written Opinion dated Jun. 27, 2016 in corresponding International Application No. PCT/US2016/022787, 10 pages.
Mcgonigle, S. et al., "Immunisation of Mice with Fractions Derived from the Intestines of Dirofilaria immitis", International Journal for Parasitology, vol. 31, 2001, pp. 1459-1466.
Morris, C. P. et al., "Vaccination with Intestinal Tract Antigens Does Not Induce Protective Immunity in a Permissive Model of Filariasis", Experimental Parasitology, vol. 135, Jun. 19, 2013, pp. 87-95.
Rosa, B. A. et al., "Functional and Phylogenetic Characterization of Proteins Detected in Various Nematode Intestinal Compartments", Molecular and Cellular Proteomics, vol. 14, Jan. 21, 2015, pp. 812-827.
Bennuru, S. et al., "Stage-Specific Proteomic Expression Patterns of the Human Filarial Parasite *Brugia malayi* and its Endosymbiont Wolbachia", PNAS, vol. 108, No. 23, Jun. 7, 2011, pp. 9649-9654.
Morris, C. P. et al., "A Proteomic Analysis of the Body Wall, Digestive Tract, and Reproductive Tract of Brugia malayi", PLoS Neglected Tropical Diseases, vol. 9, No. 9, pp. 1-21.
Extended European Search Report and Opinion dated Jul. 20, 2018 in European Patent Application No. 16765723.8, 10 pages.

(Continued)

*Primary Examiner* — Jennifer E Graser
(74) *Attorney, Agent, or Firm* — MH2 Technology Law Group, LLP

(57) ABSTRACT

The present disclosure is directed to an immunogenic composition including: at least one or at least two isolated polypeptides or immunogenic fragments thereof, and optionally a pharmaceutically acceptable carrier, wherein each polypeptide is expressed on a luminal surface of an intestine of a filarial worm, wherein each polypeptide is expressed at a level at least two-fold higher in the intestine in comparison to the level of expression of each polypeptide in a reproductive tract or a body wall of the filarial worm, wherein each isolated polypeptide has at least one transmembrane domain, and wherein each polypeptide is a non-mitochondrial polypeptide. Also provided herein is a method for preventing or treating a filarial disease.

11 Claims, 8 Drawing Sheets
Specification includes a Sequence Listing.

(56) References Cited

OTHER PUBLICATIONS

Morris, C., "Evaluating Vaccine Candidates for Filariasis", Dissertation for USU School of Medicine Graduate Program, URL: https://epo.summon.serialssolutions.com/2.0.0/link/0/eLvHCXMw Y2BQMUk1SEpJTjLQTTVPMtU1MQdd5G5uagZkGaWAjmszSQ Lf1hDpbBLibh7kbuKDuA4o0SXX0Aw0zgFaqA0sdVNy4buSQX L6wFpDHxRA4GVKefoFoAaAJUjAUB8Yd8B8C6xxmBIYgY0W 0Apm1tLi0oxipPrCTZCBxwVpnlulgSk1T4RBxxV6snZeukJYYjJo RIvBGbSrBNTpLIYAth4V3DKBHc3MxOLMYIEGTzfXEGc PXbD, Retrieved Jul. 11, 2018, 153 pages.

Kalyanasundaram, R. et al., "Multivalent vaccine formulation with BmVAL-1 and BmALT-2 confer significant protection against challenge infections with Brugia malayi in mice and jirds", Research and Reports in Tropical Medicine, Mar. 1, 2011, pp. 45-56.

Veerapathran, A. et al., "Evaluation of Wuchereria bancrofti GST as a Vaccine Candidate for Lymphatic Filariasis", PLOS Neglected Tropical Diseases, vol. 3, No. 6, Jun. 9, 2009, pp. 1-11.

Babayan, S. A. et al., "Future prospects and challenges of vaccines against filariasis", Parasite Immunology, vol. 34, No. 5, May 1, 2012, pp. 243-253.

\* cited by examiner

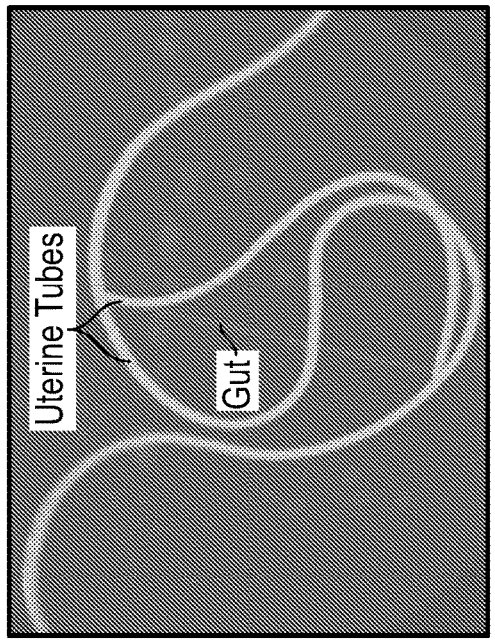
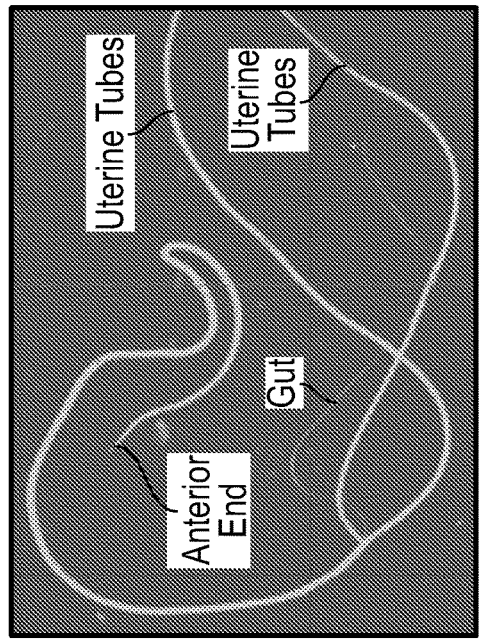
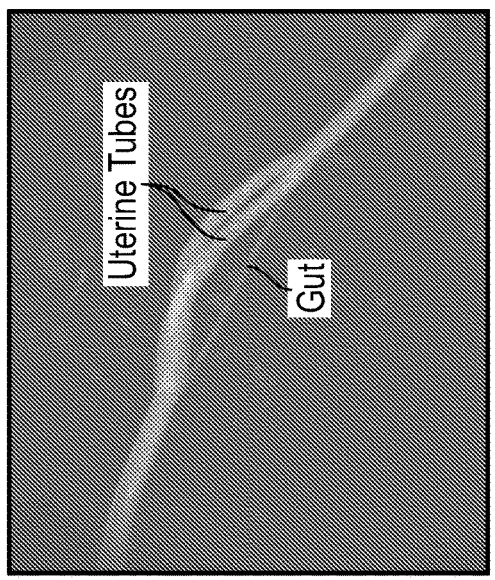
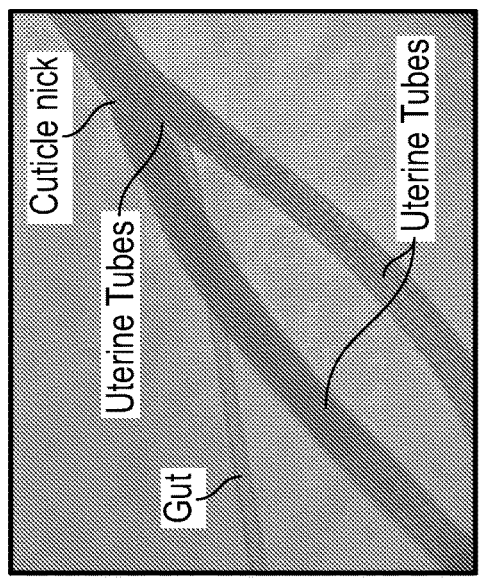
FIG. 2A
FIG. 2B

SEQUENCE LISTING

<160> NUMBER OF SEQ ID NOS: 27

<210> SEQ ID NO 1
<211> LENGTH: 1171
<212> TYPE: PRT
<213> ORGANISM: Brugia malayi
<220> FEATURE:
<221> NAME/KEY: MISC_FEATURE
<223> OTHER INFORMATION: >gi|170589239|ref|XP_001899381.1|
Immunoglobulin I-set domain containing protein [Brugia malayi]

<400> SEQUENCE: 1

```
Met Ile Thr Leu Ser Ile Leu Trp Cys Ser Leu Phe Gln Phe Ile Ala
 1               5                   10                  15

Phe Ser Arg Thr Leu Gly Pro Pro Lys Leu Asp Pro Glu Asn Gly Gly
             20                  25                  30

Glu Val Trp Phe Gln Val Asn Ser Thr Gly Ile Ala Arg Gly Lys Phe
         35                  40                  45

Ile Leu Pro Cys Tyr Ala Thr Gly Asn Pro Glu Thr Tyr Glu Trp Phe
     50                  55                  60

Lys Asp Gly Glu Lys Leu Lys Val Asp Gly Asp Arg Ile Ala Trp Glu
 65                  70                  75                  80

Lys Gln Phe Gln Ser Gly Thr Ile Ile Asn Asp Ala Arg Asp Gly
                 85                  90                  95

Asp Gln Gly Tyr Tyr Gln Cys His Ala Ser Asn Ile Phe Gly Ile Ala
            100                 105                 110

Val Ser Asn Lys Phe His Val Gln Ile Gly Val Leu Asp His Phe Val
        115                 120                 125

Pro Arg Gly Val Arg Arg Leu Ile Val Asp Glu Gly Gln Ser Leu Ser
    130                 135                 140

Ile Arg Cys Asp Ile Pro Tyr Gly Val Pro Lys Pro Ser Val Phe Trp
145                 150                 155                 160

Leu Tyr Arg Asp Thr Gln Arg Thr Asn Met Ile Glu Thr Ile Arg Tyr
                165                 170                 175

Lys His Ile Ala Val Asp Thr Glu Gly Thr Leu His Phe Thr Ala Val
            180                 185                 190

Lys Lys His Asp Gly Arg Gln Asn Leu Ile Tyr Gln Cys Ala Val Thr
        195                 200                 205

Ser Pro Val Leu Arg Gly Glu Tyr Arg Ala Gly Asn Glu Phe Gln Leu
    210                 215                 220

Ile Val Asn Pro Ala Lys Lys Asn Asn Gly Thr Ala Ile His Lys Leu
225                 230                 235                 240

Trp Phe Ser Pro Glu Lys Val Ser Val Lys Val Gly Thr Lys Leu Lys
                245                 250                 255

Leu Met Cys Ile Phe Gly Gly Arg Pro Leu Pro Asn Ile Thr Trp Ser
            260                 265                 270

Lys Leu Asn Asp Asp Leu Pro Leu Ala Arg Leu Lys Asp Phe Lys Ser
        275                 280                 285

Gln Glu Ala Asp Tyr Gly Lys Ala Leu Ile Ile Glu Asn Val Arg Ser
    290                 295                 300

Glu Asp Ala Gly Ile Tyr Glu Cys Arg Ser Gln His Leu Phe His Gln
305                 310                 315                 320

Met His Val Thr Thr Asn Ala Ala Pro Phe Trp Ile Asp Lys Pro Pro
                325                 330                 335

Glu Asp Ile Asp Glu Pro Glu Gly Ser Ser Ala Glu Ile His Cys Thr
            340                 345                 350
```

```
Ile Ser Gly Ile Pro Thr Pro Ile Ile Gln Trp Phe Ile Asn Gly Val
        355                 360                 365

Pro Leu His Glu Leu Ala Asp Asn Asp Arg Arg Met Ile Leu Asn Ser
    370                 375                 380

Gly Gln Ile Leu Arg Ile Val Asn Leu Asp His Asp Val Asp Thr Ala
385                 390                 395                 400

Val Tyr Gln Cys Asn Ala Ser Asn Pro Phe Gly Tyr Val Phe Gly Asn
                405                 410                 415

Ala Phe Val Asn Val Arg Ala Tyr Ala Pro Tyr Phe Lys Met Pro Ser
            420                 425                 430

His Arg Ile Trp Asn Val Val Arg Lys Ser Thr Val Glu Met Ser Cys
        435                 440                 445

Asp Val Glu Ala Ala Pro Lys Ala Val Val Lys Trp Val Asp Thr Asn
    450                 455                 460

Asp His Ser Ile Ala Val Val Leu Glu Lys Ile Asn Ile Phe Pro Asn
465                 470                 475                 480

His Thr Leu Arg Ile Ser Gln Val Asn Ser Ala Asp Glu Gly Leu Tyr
                485                 490                 495

Tyr Cys Asn Val Ser Asn Lys Tyr Gly Ile Asn Arg Ala Val Asn Gln
            500                 505                 510

Leu Gln Val Phe Asn Pro Thr His Phe Ile Arg Val Pro Ser Pro Lys
        515                 520                 525

Lys Ser Ile Leu Glu Ala His Glu Ser Val Glu Tyr Val Cys Glu Ala
    530                 535                 540

Val Cys Asp Pro Arg Leu Thr Ile Glu Tyr Ser Trp Thr His Asn Gly
545                 550                 555                 560

Ile Pro Ile Asn Asp Ser Val His Phe Lys Leu Leu Asn Asn Ser Leu
                565                 570                 575

Leu Ile Val Asn Ala Arg Gly Phe His Ser Gly Thr Ile Asp Cys Ile
            580                 585                 590

Val Leu Thr Asp Val Asp Val Lys Ile Ser Gly Ile Glu Leu Thr Val
        595                 600                 605

Leu Asp Val Pro Ala Ala Pro Ile Ile Thr Gly Ile Asn Cys Asn Glu
    610                 615                 620

Arg Arg Ala Met Leu Arg Trp Arg Arg Pro Asp Asp His Gly Asp Gln
625                 630                 635                 640

Ile Lys Gln Phe Leu Ile Gln Met His Thr Glu Phe Glu Glu Gly Leu
                645                 650                 655

Trp Gln Thr Val Val Glu Glu Asn Thr Ala Ala Asp Phe Tyr Gln
            660                 665                 670

Ala Asp Ile Ala Leu Ser Pro Trp Val Asn Tyr Thr Phe Arg Ile Ile
        675                 680                 685

Ala Arg Asn Ser Arg Gly Glu Ser Glu Pro Gly Phe Lys Glu Gly Ile
    690                 695                 700

Val Cys Ser Thr Lys Ala Tyr Tyr Pro Phe Thr Asn Pro Lys Asp Val
705                 710                 715                 720

Arg Ala Glu Gly Ser Glu Pro Asn Asn Met Ile Ile Glu Trp Lys Pro
                725                 730                 735

Met Asp Lys Tyr Asp Trp Asn Gly Pro Gly Leu Gln Tyr Ile Val Arg
            740                 745                 750

Tyr Lys Phe Asn Lys Pro Gly Glu Ala Trp Thr Glu Ile Arg Ile Glu
        755                 760                 765
```

-continued

Asp Pro Leu Ala Asn Tyr Thr Val Ile Arg Glu Gln Pro Thr Phe Arg
770                 775                 780

Glu Tyr Leu Ile Gln Val Glu Ser Leu Asn Ser Phe Gly Arg Ala Val
785                 790                 795                 800

Val Lys Pro Thr Ser Val Lys Gly Tyr Ser Gly Glu Asp Thr Pro Leu
                    805                 810                 815

Leu Ser Pro Ile Asp Phe Ser Val Ser Glu Phe Ile Asn Cys Thr Ala
                820                 825                 830

Val Leu Leu Ile Trp Lys His Val Asp Arg Asp Ser Val Arg Gly His
                835                 840                 845

Phe Lys Gly Tyr Leu Ile Asp Tyr Trp Glu Asn Glu Lys Pro Phe Ala
850                 855                 860

Ile Met Asn Ala Gly Ala Glu Lys His Lys Asn Glu Thr Ile Leu Tyr
865                 870                 875                 880

Asp Leu Lys Pro Met Thr Asn Tyr Thr Ala Arg Ile Arg Thr Ala Asn
                885                 890                 895

Ser Arg Tyr Leu Ser Glu Ser Pro Ser Ile Ile Lys Phe Thr Thr Pro
                900                 905                 910

Glu Gly Ile Pro Ser Lys Val His Asn Met Arg Val Arg Ala Val Gly
                915                 920                 925

Ala Arg Ser Leu Tyr Val Thr Trp Glu Pro Pro Arg Gln Pro Asn Gly
930                 935                 940

Tyr Val Arg Gly Tyr Phe Ile Thr Phe Glu Asn Ser Ser Thr Gly Val
945                 950                 955                 960

Lys Glu Glu Thr Phe Val Leu Asn Arg Gln Leu Tyr Tyr Leu Asn Glu
                965                 970                 975

Glu Gly Glu Pro Asp Thr Gly Tyr Arg Val Ser Val Trp Ala Glu Thr
                980                 985                 990

Lys Gly Gly Glu Gly Pro Lys Val  Val Arg Pro Val Arg  Thr Trp Pro
                995                 1000                1005

Leu Arg  Glu Pro Asp Val Pro  Asn Phe Thr Val Glu  Ala Ile Ser
    1010                1015                1020

Pro Thr  Thr Ala Arg Val Gln  Trp Leu Pro Ser Asn  Gly Ser Glu
    1025                1030                1035

Trp Ala  Met Pro Gly Pro Ile  Phe Leu Val Asn Tyr  Ser Ile Ala
    1040                1045                1050

Asn Ser  Asn Asn Trp Ile Glu  Ser Glu Gln Ile Ser  Leu Pro Arg
    1055                1060                1065

Thr Glu  Val Trp Leu Ser Asp  Leu Glu Glu Asp Thr  Arg Tyr Lys
    1070                1075                1080

Met Ile  Gly Ile Ala Lys Glu  Gly Gln Arg Gln Arg  Ala Ser Glu
    1085                1090                1095

Ile Ile  Thr Met Arg Ser Leu  Ser Arg Ala Thr Ile  Thr His Ile
    1100                1105                1110

Ser His  Glu Ser Leu Gln Ser  Ala Ala Trp Phe Ile  Ala Val Val
    1115                1120                1125

Ser Ala  Ile Met Phe Ala Leu  Phe Thr Ala Ser Val  Met Cys Cys
    1130                1135                1140

Cys Glu  Arg Gln Arg Asp Ser  Lys Tyr Ser Val Lys  Gln Lys Glu
    1145                1150                1155

Leu Glu  Gln Gly His His Ile  Asp Ile Glu Glu Asp  Gln
    1160                1165                1170

-continued

<210> SEQ ID NO 2
<211> LENGTH: 269
<212> TYPE: PRT
<213> ORGANISM: Brugia malayi
<220> FEATURE:
<221> NAME/KEY: MISC_FEATURE
<223> OTHER INFORMATION: >gi|170572325|ref|XP_001892066.1| EGF-like domain containing protein [Brugia malayi]

<400> SEQUENCE: 2
```

Met Thr Ile Pro Thr Asp Phe Arg Phe Thr Gly Ser Leu Leu Ile Leu
1               5                   10                  15

Ser Val Val Leu Gln Ile Pro Asn Ile Ala Thr Ile Thr Asn Pro Val
            20                  25                  30

Phe Gly Asn Asp Glu Asn Ser Met Glu His Gly Val His Tyr Gly Arg
        35                  40                  45

Thr Asn Phe Ser Cys Phe Asn Gly Gly Ser Leu Ile Asn Gly Arg Cys
    50                  55                  60

His Cys Gln Glu Arg Phe Glu Gly Glu Ala Cys Glu Ile Glu Pro Cys
65                  70                  75                  80

Leu His Gly Gly Arg Lys Ser Lys Ala Gly Lys Cys His Cys Pro Tyr
                85                  90                  95

Gly Leu Thr Gly Glu Arg Cys Glu Met Val Thr Gln Cys Ile Glu Gly
            100                 105                 110

Lys Gly Lys Leu Glu Asn Gly Arg Cys Lys Cys Glu Asp Arg Trp Thr
        115                 120                 125

Gly Ile Phe Cys Gln Ser Arg Met Cys His Asn Gly Ile Ser Val Gly
    130                 135                 140

Ser Gly Glu Gln Ile Gly Gly Phe Cys Leu Cys Asp Ile Gly Phe Thr
145                 150                 155                 160

Gly Pro Phe Cys Glu Thr Pro Ile Glu Cys Asn His Gly Ser Ile Thr
                165                 170                 175

Val Glu Asn Leu Cys Ser Cys Ala Pro Asn Trp Val Gly Glu Asp Cys
            180                 185                 190

Asn Gln Cys Ala Tyr Glu Tyr Gln Leu Ile Asp Gly Asp Cys Lys Leu
        195                 200                 205

Ile Thr Thr Glu Asn Ser Leu Ile Ala Val Arg Asn Ser Lys Ala Val
    210                 215                 220

Thr Leu Trp Ser Leu Ile Leu Val Ile Ala Ala Ala Ser Phe Ser Thr
225                 230                 235                 240

Val Leu Ile Ala Ala Val Ile Ile Ile Tyr Ile Lys Lys Cys Lys Arg
                245                 250                 255

Lys Pro Ser Arg Val Gly Ser Asp Ala Gly Thr Asp Val
            260                 265

```
<210> SEQ ID NO 3
<211> LENGTH: 306
<212> TYPE: PRT
<213> ORGANISM: Brugia malayi
<220> FEATURE:
<221> NAME/KEY: MISC_FEATURE
<223> OTHER INFORMATION: >gi|170585572|ref|XP_001897556.1| Tyrosine-protein kinase abl-1 [Brugia malayi]

<400> SEQUENCE: 3

```
Met Lys Ile Asn Leu Phe Ala Phe Pro Ala Ala Val Val Gln Ser Gly
1               5                   10                  15

Arg Leu Glu Lys Glu Pro Leu Thr Gln Lys Ala Val Ala Lys Leu His
            20                  25                  30
```

```
Pro Arg Ala Tyr Ser Thr Leu Gln Arg Ser Ile Lys Ala Ser Ser Val
            35                  40                  45

Ile Leu Pro Lys Arg Val Thr Ser Asn Asn Gly Ile Asp Asp Gly Asp
 50                  55                  60

Ala Leu Thr Lys Leu Lys Arg Lys Val Ala Ala His Pro Thr Met Pro
 65                  70                  75                  80

Asp Cys Asn Glu Thr Asp Glu Leu Glu Leu Ser Gly Ser Met Thr Arg
                85                  90                  95

Thr Gln Ser Leu Arg Asp Leu Thr Ser Lys Phe Glu Lys Leu Gly Asn
                100                 105                 110

Pro Gly Leu Ile Ala Thr Pro Ser Lys Gly Pro Phe Arg Ser Gly Glu
            115                 120                 125

Lys Arg Tyr Ser Met Met Glu Asn Val Ala Asp Thr Arg Gly Ala Val
130                 135                 140

Ser Thr Ser Asp Ser Ser Ile Ser Ser Ala Arg Glu Ser Ser Gln Pro
145                 150                 155                 160

Thr Val Ser Arg Asp Ser Leu Leu Asp Leu Tyr Arg Arg Leu Glu Ser
                165                 170                 175

Cys Ile Cys Asp Leu Arg Asn Glu Arg Val Ser Arg Val Lys Gly Gln
            180                 185                 190

His Ala Asp Tyr Ser Asp Gly Gln His Ala Leu Leu Ile Arg Leu Ser
            195                 200                 205

Asp Leu Met Gln Gln Phe His His Leu Cys Ala Ile Tyr Ala Glu Asn
210                 215                 220

Ile Ser Pro His Ser Lys Phe Arg Tyr Arg Glu Leu Leu Asn Arg Met
225                 230                 235                 240

Asp Val Phe Ile Arg Gln Leu Arg Gln Cys Ala Ser Ser Ser Asn Glu
                245                 250                 255

Val Met Gln Ala Glu Gln His Ile Ile Pro Gln Phe Glu Gln Thr Ile
            260                 265                 270

Arg Gln Ile Met His Leu Val Gln Arg Asn Leu Asp Tyr Ala Asp Thr
            275                 280                 285

Val Pro Ile Asn Thr Ser Val Ile Ile Ile Ile Ile Val Phe Ile
            290                 295                 300

Gly Ile
305

<210> SEQ ID NO 4
<211> LENGTH: 1283
<212> TYPE: PRT
<213> ORGANISM: Brugia malayi
<220> FEATURE:
<221> NAME/KEY: MISC_FEATURE
<223> OTHER INFORMATION: >gi|170580602|ref|XP_001895334.1| Protein
      kinase domain containing protein [Brugia malayi]

<400> SEQUENCE: 4

Met Ala Phe Gln Asp Lys Glu Thr Asn Glu Lys Trp Ser Thr Leu Ala
 1               5                  10                  15

Asn Cys Thr Val Met Glu Gly Asp Phe Ser Val Ser Met Ile Thr Ser
                20                  25                  30

Ser Asn Phe Thr His Glu Asn Phe Pro Val Phe Lys Arg Leu Arg Val
            35                  40                  45

Ile Thr Gly His Leu Leu Ile Phe Gln Val Ser Ala Leu Arg Ser Leu
 50                  55                  60
```

```
Lys Arg Leu Phe Pro Asn Leu Arg Ile Ile Gly Gln Glu Leu Ile
 65                  70                  75                  80

Met Asn Tyr Ala Leu Val Ile Tyr Gln Asn Thr His Leu Val Glu Ile
                 85                  90                  95

Gly Leu Pro Lys Leu Thr Thr Ile Ile Asn Gly Gly Val Arg Ile Met
            100                 105                 110

Asp Asn Thr Gln Leu Cys Tyr Ser Arg Tyr Ile Asp Trp Ser Gln Ile
            115                 120                 125

Leu Ile Gly Pro Ala Asn Asp Ile Leu Thr Asp Gln Asn Lys Gly Ser
        130                 135                 140

Asp Ser Asp Leu Cys Ser Asp Cys Val Pro Gln Asn Glu His Arg
145                 150                 155                 160

Cys His Lys Arg Asp His Met Leu Ser Cys Trp Asp Ala Glu Thr Cys
                165                 170                 175

Gln Leu Glu Cys Lys Tyr Ala Trp Asn Asp Asp Lys Thr Val Gly Pro
            180                 185                 190

Gly Cys Asp Asp Gly Glu Arg Cys His Asp Gln Cys Leu Gly Gly
    195                 200                 205

Cys Ser Ala Pro Asp Asp Pro Ser Ala Cys His Phe Cys Lys Asn Val
210                 215                 220

Val Tyr Gln Gly Ile Cys Met Asp Lys Cys Pro Ile Gly Leu Tyr Glu
225                 230                 235                 240

Ile His His Ile Tyr Leu Val Arg Arg Cys Val Thr Ile Glu Glu Cys
                245                 250                 255

Arg Asn Ile Ser Ala Pro Val Thr Met Glu Ser Thr Lys Lys Arg Met
            260                 265                 270

Leu Ile Val Glu Asn Met Cys Arg Val Asp Cys Pro Phe Gly Gln Glu
        275                 280                 285

Ile Asp Pro Thr Thr Ser Ser Gly Cys Ile Lys Cys Glu Gly Tyr Cys
        290                 295                 300

Pro Val Lys Cys Lys Gly Gly Thr Ile Asp Ser Phe Ala Arg Ile Asn
305                 310                 315                 320

Asp Tyr Leu Phe Lys Lys Cys Asn Val Ile Glu Gly Tyr Leu Glu Ile
                325                 330                 335

Glu Leu Arg Lys Gly Leu Asp Ala Ala Gly Met Glu Lys Ile Gly Glu
            340                 345                 350

Ala Leu Gly Tyr Ile Glu Val Ile Glu Gly Tyr Leu Leu Ile Asp Phe
        355                 360                 365

Ser Ile Ser Phe Ile Ser Leu His Met Phe Lys Arg Leu Arg Leu Ile
        370                 375                 380

Lys Gly Ser Ile Leu Tyr Arg Asp Arg Tyr Ala Leu Ala Ile Phe Glu
385                 390                 395                 400

Asn Ala Asn Leu Arg Gln Ile Phe Asp Ile Glu Lys Gln Pro Leu Val
                405                 410                 415

Ile Gly Asn Gly Thr Val Leu Phe Gln Asn Asn Arg Met Leu Cys Tyr
            420                 425                 430

Asn Arg Ile Lys Ala Leu Ile Asp His Thr Gly Leu Thr Asp Val Lys
        435                 440                 445

Glu Asn Asp Val Ser Tyr Tyr Ser Asn Gly Asp Arg Ala Val Cys Asp
        450                 455                 460

Glu Thr Thr Phe Glu Val Gln Thr Glu Asp Val His Ser Phe Gly Phe
465                 470                 475                 480

Met Ile Ser Trp Val Ala Phe Asn Thr Thr Asp Met Asp His Arg Lys
```

```
                485                 490                 495
Phe Leu Gly Tyr Gln Val Phe Tyr Lys Lys Val Asp Gly Pro Asp Pro
                500                 505                 510

Ser Leu Ser Ile Asp Asp Arg Ser Ala Cys Ser Asp Ser Trp Gln
        515                 520                 525

Met His Phe Glu Pro Glu Lys Gly Asn Gly Asn Glu Gly Leu Asn Arg
        530                 535                 540

Gly Ala Gly Ile Phe Ala Val Glu Ser Asn Thr Trp Tyr Ala Tyr Tyr
545                 550                 555                 560

Val Gln Thr Lys Leu Ile Asn His Pro Gly Ala Arg Asn Ala Ile Ser
                565                 570                 575

Lys Ile His Phe Leu Lys Thr Leu Phe Ser Thr Pro Asp Pro Pro Lys
                580                 585                 590

Asp Val Val Gly Lys Ser Leu Ile Met Lys Pro Asp Gln Ile Asp Leu
                595                 600                 605

Ala Trp Glu Pro Pro Glu Arg Pro Asn Gly Asp Ile Thr His Tyr Ile
610                 615                 620

Val Lys Trp Gln Val Leu Gly Asp Asp Pro Ser Thr Val Ser Gly Asn
625                 630                 635                 640

Val Cys Asp Asp Lys Thr Gly Ala Gly Leu Arg His His Lys Asp Ile
                645                 650                 655

Asn Asp Arg Phe Thr His Ala Pro Ala Gln Gln Ser Cys Ser Lys Ala
                660                 665                 670

Gly Cys Cys Asp Cys Arg Leu Leu Lys Gln Arg Gln Gln Ser Lys Pro
                675                 680                 685

Asn Asn Ile Tyr Leu Glu Asp Glu Arg Ala Asn Glu Ala Asp Phe Glu
690                 695                 700

Asn Ala Val Gln Asn Leu Val Phe Val Gln Asp Ser Lys Arg Ser
705                 710                 715                 720

Met Ile Glu Lys Ser Gln Ile Arg Arg Ser Arg Arg Ser Ile Leu Lys
                725                 730                 735

Asp Tyr Asn Glu Pro Asn Glu Lys Gln Tyr Gly Asp Glu Arg Phe Ile
                740                 745                 750

Phe Ile Thr Gln Asn Glu Val Asn Glu Thr Thr Ser Leu Tyr Arg Ser
                755                 760                 765

Glu Leu Asp Ile Gly Thr His Lys Ile Asn Val Thr Thr Arg Arg Leu
                770                 775                 780

Ser Ile Val Gly Leu Arg His Tyr Thr Gln Tyr Gln Ile Trp Ile His
785                 790                 795                 800

Ala Cys Gln Asn Ile Ser Ala Pro Gly Gly Ala Tyr Cys Ser Gln Arg
                805                 810                 815

Pro Gly Trp Met Val Val Arg Thr Ala Pro Ile Ala Ser Asn Asp Leu
                820                 825                 830

Val Asp Asn Arg Thr Ile Lys Val Ile Asn Ser Thr Ser Phe Lys Gln
                835                 840                 845

Asp Pro Arg Ser Arg Lys Ile Thr Trp Gln Glu Pro Ser Asn Pro Asn
                850                 855                 860

Gly Ile Ile Leu Ala Tyr Arg Val Thr Val Ala Glu Asn Leu Ala
865                 870                 875                 880

Gln Thr Pro Ile Ser Gln Cys Val Lys Ala Ser Asn Phe Arg Glu Arg
                885                 890                 895

Glu Gly Val Val Phe Asn Gly Leu Ala Glu Gly Glu Tyr Leu Val Gln
                900                 905                 910
```

Val Glu Thr Ile Ser Met Ala Ser Leu Ser Phe His Ala Ile Lys Glu
        915                 920                 925

Ile Ala Val Ala His Lys Leu Phe Lys Ile Val Lys Pro Thr Phe Phe
930                 935                 940

Thr Thr Thr Val Val Ser Phe Ile Ala Val Ile Val Leu Leu Val Leu
945                 950                 955                 960

Ser Ile Gly Ser Leu Ala Ala Tyr Tyr Ile Ser Arg Lys Ile Leu Gly
            965                 970                 975

Glu Lys Val Arg Glu Tyr Val Arg Gln Gln Ile Ser Ala Asn Pro Glu
            980                 985                 990

Tyr Leu Ser Gln Met Asp Val Tyr Lys Pro Asp Glu Trp Glu Leu Lys
            995                 1000                1005

Arg Ser Ala Ile His Leu Glu Asp Glu Ile Gly Arg Gly Thr Phe
    1010                1015                1020

Gly Lys Val Tyr Arg Gly Tyr Gly Asp Asn Cys Lys Ser Tyr Leu
    1025                1030                1035

Gly Val Thr Phe Gly Glu Cys Ala Ile Lys Thr Val Ser Glu Thr
    1040                1045                1050

Ala Asn Ser Ala Glu Arg Leu His Phe Leu Ile Glu Ala Ser Val
    1055                1060                1065

Met Lys Gln Phe Asn Thr Pro Phe Ile Val Lys Leu Tyr Gly Val
    1070                1075                1080

Val Ser Asp Gly Gln Pro Val Leu Val Val Met Glu Met Met Lys
    1085                1090                1095

Lys Gly Asn Leu Arg Asp Tyr Leu Arg Ser Arg Arg Pro Asn Ala
    1100                1105                1110

Glu Glu Asn Val Asn Gly Leu Pro Val Pro Gly Ala Ile Asp Phe
    1115                1120                1125

Phe Arg Trp Ala Ser Gln Val Ala Asp Gly Met Ala Tyr Leu Glu
    1130                1135                1140

Ser Leu Lys Phe Cys His Arg Asp Leu Ala Ala Arg Asn Cys Met
    1145                1150                1155

Val Asn Glu Phe Asp Thr Val Lys Ile Gly Asp Phe Gly Met Ala
    1160                1165                1170

Arg Asp Ile Tyr Tyr His Glu Tyr Tyr Lys Pro Ala Gly Lys Arg
    1175                1180                1185

Leu Met Pro Val Arg Trp Met Ala Pro Glu Ser Leu Met Asp Gly
    1190                1195                1200

Lys Phe Thr Met Lys Ser Asp Val Trp Ser Tyr Gly Ile Thr Leu
    1205                1210                1215

Tyr Glu Met Leu Thr Leu Ala Gln Gln Pro Tyr Leu Gly Leu Ala
    1220                1225                1230

Asn Glu Ser Val Phe Asp Tyr Ile Gly Val Lys Lys Lys Ile Leu
    1235                1240                1245

Thr Arg Pro Thr Gly Cys Pro Asp Phe Trp Tyr Glu Leu Met Lys
    1250                1255                1260

Arg Cys Trp Lys Tyr Asp Pro Arg Glu Arg Pro Thr Phe Ala Gln
    1265                1270                1275

Leu Leu Glu Phe Tyr
    1280

<210> SEQ ID NO 5
<211> LENGTH: 293

```
<212> TYPE: PRT
<213> ORGANISM: Brugia malayi
<220> FEATURE:
<221> NAME/KEY: MISC_FEATURE
<223> OTHER INFORMATION: >gi|170588697|ref|XP_001899110.1| Ser/Thr
      protein phosphatase family protein [Brugia malayi]

<400> SEQUENCE: 5

Met Asn Ser Lys His Phe Arg Phe Leu Arg Leu Val Ala Asn Glu
1               5                   10                  15

Leu Ser Asn Arg Ile Phe Ala Val Leu Ala Val Val Phe Val Leu
                20                  25                  30

Ala Gly Leu Trp Val Thr Leu Leu Pro Pro Ala Val Arg Arg Ile Thr
            35                  40                  45

Ile Lys Ile Asp Asn Leu Pro Glu Val Gln Lys Gly Phe Thr Val Ala
50                  55                  60

Leu Leu Ser Asp Leu His Ile Gly Pro Thr Val Gly Cys Ser Lys Ile
65                  70                  75                  80

Gln Lys Met Val Asn Thr Ile Asn Leu Phe Lys Pro Asp Val Ile Ala
                85                  90                  95

Ile Ser Gly Asp Leu Ala Asp Gly Leu Val Pro Asn Leu Glu Lys Ala
                100                 105                 110

Ala Tyr Pro Leu Met Asn Leu Thr Ser Lys Tyr Gly Ile Tyr Phe Ala
                115                 120                 125

Thr Gly Asn His Glu Tyr Leu His Gly Asn Val Asp Glu Trp Phe Val
130                 135                 140

Phe Leu Lys Lys Ile Lys Ile Pro Leu His Asn Lys Asn Lys Lys
145                 150                 155                 160

Ile Leu Val Gly Asn Ser Arg Ile Cys Ile Ala Gly Ser Asp Leu
                165                 170                 175

Phe Ala Glu Gln Ser Arg Phe Ser Gly His Val Met Asp Tyr Lys Lys
                180                 185                 190

Ala Leu Arg Gly Cys Asn Lys Asn Asp Thr Thr Ile Met Leu Ile His
                195                 200                 205

Gln Pro Asn Ala Val Arg Ile Ile Leu Asn Asp Val Glu Thr Ala Lys
210                 215                 220

Asn Ile Asp Leu Ile Leu Ser Gly His Thr His Gly Gly Gln Met Tyr
225                 230                 235                 240

Val Phe Val Pro Leu Val Tyr Phe Trp Asn Ala Tyr Phe Arg Gly Leu
                245                 250                 255

Tyr Tyr Asn Lys Ala Thr Gly Tyr Val Tyr Val Ser Ala Gly Val
                260                 265                 270

Asn Tyr Phe Gly Pro Pro Val Lys Ile Phe Asp Gly Asn Glu Ile Ile
                275                 280                 285

Ile Ile Lys Leu Val
                290

<210> SEQ ID NO 6
<211> LENGTH: 839
<212> TYPE: PRT
<213> ORGANISM: Brugia malayi
<220> FEATURE:
<221> NAME/KEY: MISC_FEATURE
<223> OTHER INFORMATION: >gi|170578901|ref|XP_001894589.1| DnaJ domain
      containing protein [Brugia malayi]
<220> FEATURE:
<221> NAME/KEY: misc_feature
<222> LOCATION: (351)..(351)
<223> OTHER INFORMATION: Xaa can be any naturally occurring amino acid
```

```
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid

<400> SEQUENCE: 6

Met Asn Tyr Leu Leu Phe Leu Val Leu Ser Leu Tyr Tyr Ile Asp
1               5                   10                  15

Gly Lys Ile Ser Thr Glu Ile Glu Asp Pro Tyr Gln Val Leu Gly Val
            20                  25                  30

Ser Arg Lys Ala Thr Ile Lys Glu Ile Lys His Ala Tyr Lys Ala Leu
        35                  40                  45

Val Lys Glu Trp His Pro Asp Lys Ser Glu Pro Asp Ser His Glu
50                  55                  60

Lys Phe Met Ala Ile Thr His Ala Tyr Glu Ile Leu Ser Asp Pro Val
65                  70                  75                  80

Lys Arg Glu Arg Tyr Asp Lys Phe Asp Ser Phe Asp Pro Pro Ser
                85                  90                  95

Ser His Ala Tyr Thr His Tyr Ser Ser Asp Asp Leu Phe Gly Phe Gly
                100                 105                 110

Phe Gly Gly Phe Asp Asn Gly Asn Ser Phe Phe Gln Lys His Arg Ile
            115                 120                 125

Ser Met Arg Ile Phe Ser His Ala Leu Met Gly Arg Ser Tyr Phe Gln
130                 135                 140

Pro Ile Ile Ile Phe Ala Tyr Ser Gly Tyr Cys Gln Leu Cys Phe His
145                 150                 155                 160

Leu Glu Pro Ile Trp Gln Ser Val Val Asn Asp Leu Glu Pro Leu Gly
                165                 170                 175

Tyr Gly Ile Gly Thr Val Ser Ala Ile Thr Asp Gly Asn Leu Leu Glu
            180                 185                 190

Lys Met Arg Ile Ser Arg Leu Pro Ser Ile Val Val Glu Gly
        195                 200                 205

Arg Val Ile His Tyr Arg Gly Ser Met Gln Arg Lys Ile Leu Tyr Ser
            210                 215                 220

Val Phe Leu Ile Ile Ser Leu Lys Asn Ile Thr Asn Ile Ala Phe Ala
225                 230                 235                 240

Ala Leu Ser Ala Lys Ala Val Arg Ile Phe Ala Arg Asp Val Ile Pro
                245                 250                 255

Asn Thr Phe Leu Leu Lys Ile Thr Asn His Asp Gly Leu Arg Arg Phe
                260                 265                 270

Ile Asp Gln Trp Gln Thr Ser Asn Lys Ile Ser Val Val Ile Phe Gly
            275                 280                 285

Asn Lys Glu Asn Pro Arg Ile Arg Tyr Met Leu Thr Ala Met Lys Tyr
290                 295                 300

Ala Thr Phe Ala Arg Phe Ala Tyr Val Tyr Leu Asn Asp Gln Ser Thr
305                 310                 315                 320

Glu Ile Val Lys Met Arg Glu Ala Leu Asp Ile Thr Cys Phe Lys Cys
            325                 330                 335

Glu Asn Ile Leu Ile Phe Asn Asp Phe Pro Gln Lys Gly Pro Xaa Ala
```

-continued

```
                340                 345                 350
Arg Leu Ser Val Gly Asn Gly Gln Gln Phe Asn Ile Asp Thr Met Gly
                355                 360                 365
Glu Phe Ile Glu Arg Asn Lys Tyr Leu Thr Leu Pro Arg Leu Ser Ser
        370                 375                 380
Gln Ser Tyr Phe Asp Asp Leu Cys Pro Ile Ser Ser Arg Ser Leu Arg
385                 390                 395                 400
Ser Leu Cys Val Ile Leu Met Thr Thr Asp Ser Ser Ser Asp Leu Ser
                405                 410                 415
Gln Ile Ala Ser Leu Arg Asn Phe Val His Xaa Arg Gly Ala Asn Phe
            420                 425                 430
Lys Asn Glu Arg Leu Arg Phe Ala Tyr Val Tyr Val Gly Lys Gln Lys
        435                 440                 445
Glu Phe Val Met Thr Phe Phe Asp Gly Leu Ser Pro Ser Glu Arg Ser
    450                 455                 460
Ser Leu Gln Glu Xaa Gly His Gly Leu Leu Ile Leu Trp Arg Tyr Asp
465                 470                 475                 480
Gln Lys Lys Val Arg Phe Ala Trp Leu Ser Asn Trp Ser Val Glu Glu
                485                 490                 495
Ser Val Ser Glu Asn Asp Leu Gln Phe Glu Leu Asp Ala Tyr Ile Lys
            500                 505                 510
Gly Val Lys Lys Leu Glu Tyr Gln Ala Thr Leu Lys Pro Val Leu Asp
        515                 520                 525
Glu Tyr Arg Pro Ser Trp Phe Thr Arg Val Ser Arg Ala Ala Val Arg
    530                 535                 540
Met Phe Glu Ala Met Trp Phe Ser Leu Thr Lys Glu Glu Ala Leu Pro
545                 550                 555                 560
Leu Leu Ser Ala Ile Gly Thr Leu Leu Ile Ile Phe Phe Ile Gly Tyr
                565                 570                 575
Gly Leu Ser Tyr Ala Asn Ala Leu Glu Glu Lys Ser Arg Ser His Val
            580                 585                 590
Ser Gln Glu Ile Arg Lys Glu Asn Lys Xaa Thr Val Asp Asp Asp Asp
        595                 600                 605
Gln Cys His Pro Glu Asp Pro Arg Val Gly Pro Arg Ile Ser Ser Asn
    610                 615                 620
Arg Pro Arg Val Leu Lys Arg Gln Gln Lys Ile Met Arg Glu Met Glu
625                 630                 635                 640
Pro Met Met His Glu Leu Arg Ala Glu Thr Tyr Phe Gly Met Ile Arg
                645                 650                 655
Leu Leu Lys Pro Gly Cys Arg Ser Ile Val Val Leu Val Asp Glu Gln
            660                 665                 670
Ser Lys Asp Ile Leu Leu Pro Gln Phe Ala Lys His Ile Trp Pro Phe
        675                 680                 685
Arg Asn Asn Lys Thr Phe Ser Phe Gly Tyr Leu Met Val Glu Lys Asn
    690                 695                 700
Leu Ser Trp Phe Arg Lys Leu Leu Glu His Thr Leu Pro Ala Glu Ser
705                 710                 715                 720
Gly Gln Ala His Glu Asp Gly Ser Ser Met Tyr Glu Arg Leu Lys Asn
                725                 730                 735
Ile Asn Pro Arg Lys Thr Leu Gly Thr Val Leu Val Leu Cys Gly Trp
            740                 745                 750
Lys Leu Tyr Phe Asn Met Tyr His Pro Met His Thr Pro Pro Gly Lys
        755                 760                 765
```

```
Lys His Phe Leu Gly Phe Asp Asp Asp Gly Lys Asp Cys Ser Ser Glu
    770                 775                 780

Asp Ser Asp Ala Asp Lys Ala Thr Arg Glu Glu Val Gln Thr Leu Arg
785                 790                 795                 800

Arg Gly Gln His Leu Lys Leu Glu Asp Val Leu Asn Gly Leu Pro Asn
                805                 810                 815

Trp Leu Asp Arg Leu Val Glu Gly Ser Ile Arg Arg Tyr Tyr Val Pro
            820                 825                 830

Glu Trp Pro Asn Asn Leu Arg
        835

<210> SEQ ID NO 7
<211> LENGTH: 125
<212> TYPE: PRT
<213> ORGANISM: Brugia malayi
<220> FEATURE:
<221> NAME/KEY: MISC_FEATURE
<223> OTHER INFORMATION: >gi|170582031|ref|XP_001895946.1|
      hemimethylated DNA binding domain containing protein [Brugia
      malayi]

<400> SEQUENCE: 7

Met Lys Leu Leu Ile Tyr Gln Lys Thr Arg Lys Lys Leu Asn Ile Leu
1               5                   10                  15

Val Val Ile Leu Leu Lys Leu Ile Ala Pro Phe Cys Ser Leu Glu Pro
            20                  25                  30

Arg Asp Pro Arg Pro Pro Tyr Ile Lys Tyr Arg Val Gly Asp Val Val
        35                  40                  45

Arg His Lys Ile His Gly Tyr Arg Gly Val Ile Ile Gly Trp Asp Glu
    50                  55                  60

Lys Ala Val Ala Pro Gln Ser Trp Leu Asp Lys Thr His Lys Gly Arg
65                  70                  75                  80

Lys Asp Trp Ser Glu Met Pro Asn Tyr Ser Val Ile Ile Asp Thr Arg
                85                  90                  95

Asp Arg Leu Ile Pro Gln Leu Ala Tyr Val Val Glu Glu Asn Ile Glu
            100                 105                 110

Leu Gly Glu Gly Arg Val Trp Val Ser Ser Leu Ser Phe
        115                 120                 125

<210> SEQ ID NO 8
<211> LENGTH: 364
<212> TYPE: PRT
<213> ORGANISM: Brugia malayi
<220> FEATURE:
<221> NAME/KEY: MISC_FEATURE
<223> OTHER INFORMATION: >gi|170591272|ref|XP_001900394.1| Fukutin
      [Brugia malayi]
<220> FEATURE:
<221> NAME/KEY: misc_feature
<222> LOCATION: (329)..(329)
<223> OTHER INFORMATION: Xaa can be any naturally occurring amino acid

<400> SEQUENCE: 8

Met Val Leu Leu Met Ile Lys His Leu Cys Leu Arg Phe Phe Val Ala
1               5                   10                  15

Ile Ile Val Leu Ala Gly Val Ile Tyr Tyr Phe Glu Tyr Ile Arg Ile
            20                  25                  30

Ser Ile Lys Asn Leu Thr Lys Tyr Thr Ala Ala Thr Asp Tyr His Ser
        35                  40                  45

His Ile Ser Asp Asp Asn Phe His Leu Glu Lys Gln Glu Leu Gln Tyr
```

```
            50                  55                  60
Leu Lys Gln Phe Asp His Leu Phe Trp Leu Arg Asp Ile Ile Pro Asn
 65                  70                  75                  80

Lys Tyr Val Phe Gly Thr Tyr Asp Asn Ser Glu Ile Ser Val Ala Ile
                 85                  90                  95

Gly Asn Ile Ile Val Tyr Arg Met Val Asn Ser Ser Asn Glu Asp Tyr
            100                 105                 110

Val Lys Phe Gln Arg Asn Glu Asp Leu Arg Ala Ala Tyr Gly Leu Tyr
        115                 120                 125

Ala Ile Lys Lys Tyr Val Phe Glu Arg Glu Thr Trp Ile Pro Ala Asn
    130                 135                 140

Lys Gly Glu Phe Leu Arg Lys Trp Asp Asn Gly Arg Phe Leu Asp Cys
145                 150                 155                 160

Ile Arg Leu Asn Ile Ser Asn Asn Trp Asn Lys Ser Val Ile Pro Asp
                165                 170                 175

Gly Tyr Val Asn Asn Met Ala Glu Phe Arg Asp Phe Leu Glu Ser Tyr
            180                 185                 190

Ala Ser Thr Pro Phe Leu Phe Gly Gly Thr Leu Leu Gly Trp Tyr Arg
        195                 200                 205

Glu Cys Ser Phe Ile Lys Asp Thr Thr Asp Val Asp Met Ala Met Lys
    210                 215                 220

Ile Thr Ser Leu Asp Leu Lys Met Leu Lys Asn Met Glu Lys Ser Ser
225                 230                 235                 240

Asp Phe Lys Leu Phe Trp Ile Leu Gly Lys Val Ser Asp Ser Leu Glu
                245                 250                 255

Leu Ser Val Tyr Ser Gly Ser Ile Lys Ile Asp Leu Phe Phe Leu Tyr
            260                 265                 270

Glu Ser Lys Asp Ser Ala Trp Val Gly Met Ile Val Ser Lys Arg
        275                 280                 285

Lys Lys Phe Arg Trp Ile Tyr Pro Pro Ile Ser Gln Ile Cys Thr Gly
    290                 295                 300

Asp Leu Leu Gly Arg Leu Phe His Val Pro Cys Asn Val Glu Lys Ile
305                 310                 315                 320

Leu Lys Ala Asp Tyr Gly Asn Trp Xaa Val Pro His Pro Thr Ala Asn
                325                 330                 335

Phe Thr Trp Tyr Gln Ser His Lys Asn Val Lys Glu Ala Gly Tyr Trp
            340                 345                 350

Ser Glu Ser Glu Trp Asn Asp Thr Tyr Lys Val Phe
        355                 360

<210> SEQ ID NO 9
<211> LENGTH: 538
<212> TYPE: PRT
<213> ORGANISM: Brugia malayi
<220> FEATURE:
<221> NAME/KEY: MISC_FEATURE
<223> OTHER INFORMATION: >gi|170577851|ref|XP_001894161.1| UDP-
    glucoronosyl and UDP-glucosyl transferase family protein [Brugia
    malayi]

<400> SEQUENCE: 9

Met Tyr His Ala Glu Trp Tyr Leu Ala Ser Leu Ile Ile Ile Phe His
  1               5                  10                  15

Ala Ser Gln Asn Asp Ser Tyr Lys Ile Leu Val Tyr Asn Pro Arg Phe
                 20                  25                  30

Gly Lys Ser His Thr Lys Phe Leu Gly Ser Ile Ala Asp Thr Leu Val
```

```
            35                  40                  45
Asn Ala Gly His Asn Val Thr Glu Phe Ala Pro Val Leu Phe Glu Phe
 50                  55                  60
Ser Asp Ser Thr Gly Ser Lys Leu Ala Lys Thr Val Lys Ile Asp Ala
65                  70                  75                  80
Asp Pro Glu Ile Ser Lys Ile Met Asn Val Glu Ile Phe Ala Gln Asp
                85                  90                  95
Ala Trp Lys Arg Asn Gln Gln Ser Ile Phe Ser Leu Ile Ser Val Met
                100                 105                 110
Lys Arg Met Ser Asp Ala Leu Leu Lys Asn Cys Glu Phe Gln Leu Lys
            115                 120                 125
Gln Glu Lys Ile Met Gln Glu Leu Lys Ser Glu Lys Phe Asp Leu Ala
            130                 135                 140
Ile Phe Glu Phe Asn Gln Cys Phe Ala Gly Ile Ile Glu Leu Leu Arg
145                 150                 155                 160
Ile Pro Ala His Ile Val Val Ser Pro Thr Ala Leu Phe Glu Tyr Ala
                165                 170                 175
Ile Glu Cys Phe Gly Ile Pro Asn Ile Pro Ser Tyr Ile Pro Ser Leu
                180                 185                 190
Leu Thr Gln Tyr Thr Asp Lys Met Thr Tyr Leu Gln Arg Leu Lys Asn
            195                 200                 205
Leu Ile Ile Thr Ile Leu Thr Thr Lys Leu Leu Asp Asn His Thr Ile
            210                 215                 220
Arg Cys Gln Ala Leu Phe Arg Arg Leu Tyr Gly Asp Gln Phe Ile Asp
225                 230                 235                 240
Leu Lys Glu Lys Leu Ala Gln Val Thr Tyr Val Leu Thr Asn Thr Asp
                245                 250                 255
Pro Leu Phe His Ile Ser Arg Pro Thr Ile His Lys Met Leu Glu Leu
                260                 265                 270
Gly Gly Leu Ala Leu Pro Lys Pro Gln Pro Leu Ser Lys Glu Trp Ile
            275                 280                 285
Ala Val Met Asn Lys Arg Lys Ala Val Val Leu Val Ser Phe Gly Thr
            290                 295                 300
Val Thr Leu Ser Cys Trp Met Pro Asn Glu Thr Lys Gln Ala Leu Leu
305                 310                 315                 320
Asp Ala Phe Asp Ser Phe Pro Asn Val Thr Phe Ile Trp Lys Tyr Glu
                325                 330                 335
Lys Asp Glu His Leu Ile Ala Glu Gly Arg Pro Asn Val Ile Thr Ser
            340                 345                 350
Lys Trp Leu Pro Gln Ser Asp Leu Leu Ala His Lys Asn Leu Ile Ala
            355                 360                 365
Phe Leu Thr His Gly Gly Met Asn Ser Ile Thr Glu Thr Leu Asn Arg
            370                 375                 380
Gly Lys Pro Ile Val Val Pro Leu Phe Gly Asp Gln Met Gln Asn
385                 390                 395                 400
Ala Val Leu Val Gln Arg Leu Gly Leu Gly Ile Lys Leu Ser Leu Ser
                405                 410                 415
Glu Leu Ala Ile Lys Glu Lys Ile Lys Asn Ala Ile Tyr Asn Ile Ile
            420                 425                 430
Tyr Asp Lys Ser Tyr Ala Gln Lys Val Glu Arg Leu Ser Lys Met Met
            435                 440                 445
Ala Lys Lys Pro Asn Gln Ala Glu Glu Gln Leu Ile Lys His Val Glu
            450                 455                 460
```

```
Phe Ala Ala Glu Phe Gly Gln Ile Ala Asn Phe Asp Pro Tyr Gly Arg
465                 470                 475                 480

Lys Met Ser Phe Val Ser Tyr Tyr Met Leu Asp Ile Ile Ile Pro Phe
            485                 490                 495

Ile Ile Leu Ile Phe Phe Ile Ile Thr Ile Ile Cys Tyr Leu Ile Ile
        500                 505                 510

Arg Leu Phe Arg Lys Leu Phe His Lys Ala Val Ile Cys Asn Asn Asn
        515                 520                 525

Asn Ser Ile Ile Thr Lys Val Lys Lys Asn
        530                 535
```

<210> SEQ ID NO 10
<211> LENGTH: 265
<212> TYPE: PRT
<213> ORGANISM: Brugia malayi
<220> FEATURE:
<221> NAME/KEY: MISC_FEATURE
<223> OTHER INFORMATION: >gi|170593263|ref|XP_001901384.1| CG3054-PA
      [Brugia malayi]

<400> SEQUENCE: 10

```
Met Asp Val Glu Ile Gly Leu Ser Thr Lys Glu Ala Phe Ala Lys Leu
1               5                   10                  15

Cys Ala Val Leu Glu Phe Glu Ile Asp Lys Glu Arg Gly Arg Ala Ala
            20                  25                  30

Gly Pro Phe Thr Phe Arg Phe Leu Ala His Asp Ala Leu Thr Thr Gly
        35                  40                  45

Asn Phe Cys Val Ile Tyr Ala Val Ala Ser Ile Ile Cys Cys Leu Val
    50                  55                  60

Leu Leu Ser Cys Ser Leu Leu Arg Asp Cys Thr Leu Leu Asp Gln Leu
65                  70                  75                  80

Ala Ser Phe Leu Phe Leu Thr Ile Ser Ile Cys Asn Ile Tyr Cys Ser
            85                  90                  95

Leu Lys Ile Tyr Arg Thr Glu Arg Tyr Ala Ile Ile Glu Lys Ala Leu
            100                 105                 110

Asp Ile Leu Asp Ile Leu Lys Ser Leu Lys Val Glu Asn Phe Arg Tyr
        115                 120                 125

Glu Asn Leu Tyr Ala Pro Pro Ser Asp Ala Ile Ser Leu Gln Trp Thr
130                 135                 140

Tyr Arg Asp His Lys Leu Val Asn Val Pro Trp Met Leu Leu Val Asp
145                 150                 155                 160

Gly Asp Ile Ile Gln Leu Arg Ala Gly Gln Ser Pro Pro Tyr Gln Cys
            165                 170                 175

Ile Ser Gln His Gly Asp Phe Ile Gly Leu Gly Asp Lys Pro Arg Leu
        180                 185                 190

Leu Lys Ile Leu Pro Ser Lys Ser Thr Leu Trp Lys Ile Val Glu Pro
    195                 200                 205

Pro Ile Val Asp His Ile Arg Ala Ala Phe Arg Asn His Arg Lys Lys
210                 215                 220

His Ser Asn Leu Leu Asn Phe Glu Ile His Thr Thr Leu His Phe Ile
225                 230                 235                 240

Leu Glu Arg Cys Phe Leu Pro Phe Ile Leu Thr Met Met Leu Ile Val
            245                 250                 255

His Cys Phe Arg Glu Val Pro Thr Ile
            260                 265
```

```
<210> SEQ ID NO 11
<211> LENGTH: 1513
<212> TYPE: PRT
<213> ORGANISM: Brugia malayi
<220> FEATURE:
<221> NAME/KEY: MISC_FEATURE
<223> OTHER INFORMATION: >gi|170576299|ref|XP_001893572.1| AMOP domain
      containing protein [Brugia malayi]

<400> SEQUENCE: 11
```

Met Ile Leu Ser Thr Ile Phe Leu Phe Val Ile Val Ile Lys Cys Leu
1               5                   10                  15

Ser Leu Leu Ser Ser Ala Gln Gln Ile Pro Gln Gln Asn Pro Val Pro
            20                  25                  30

Ser Thr Asn Gln Glu Asn Leu Asn Pro Gly Gln Glu Gly Ala Lys Ile
        35                  40                  45

Phe Thr Gly Arg Asp Ser Ile Ser Ala His Val Asn Leu Val Pro Phe
    50                  55                  60

Gly Pro Glu Ala Gly Asp Gln Lys Val His Pro Gly Met Leu Thr Ser
65                  70                  75                  80

Gly Gln Thr Ile Asn Leu His Met Phe Phe Pro Phe Tyr Gly Gly Leu
                85                  90                  95

Tyr Asn Tyr Ser Val Leu Ser Val Asn Gly Tyr Ile Ala Phe Ala Thr
            100                 105                 110

Val Leu Asp Gln Gly Pro Thr Ile Asn Val Gly Val Glu Ser Thr Asn
        115                 120                 125

Trp Pro Gln Gln Gln Asp Pro Ala Met Ile Ala Pro Tyr Leu Cys Lys
130                 135                 140

Gln Gln Ile Val Gln Asn Pro Ser Pro Gly Leu Lys Thr Gly Val Tyr
145                 150                 155                 160

Tyr Arg Leu Met Leu Arg Gln Ser Leu Phe Gly Arg Gly Ser Asn Ile
                165                 170                 175

Asn Ile Pro Phe Gly Gly Thr Met Glu Gln Ser Ser Phe Phe Arg Gln
            180                 185                 190

Pro Ala Ser Gln Ala Cys Pro Ser Thr Ser Asp Ser Tyr Val His Cys
        195                 200                 205

Asp Gln Asn Ser Asp Tyr Phe Leu Asp Gln Met Met Arg Trp Leu Gln
    210                 215                 220

Glu Gly Val Ala Gly Ala Ala Phe Arg Ala Asp Ala Phe Val
225                 230                 235                 240

Val Thr Trp Tyr Asn Thr Ala Ser Ala Ile Val Gly Arg Ser Asp Ile
                245                 250                 255

Asp Ala Gly Gln Leu Ser Thr Tyr Gln Ala Ile Trp Leu Thr Asp Gln
            260                 265                 270

Pro Gly Arg Leu Ser Tyr Val Ile Leu Asn Tyr Asp Lys Leu Gly Phe
        275                 280                 285

Asp Ala Ala Asp Phe Arg Met Asn Ser Arg Ser Gly Arg Cys Gln Ala
    290                 295                 300

Leu Phe Asn Gly Gly Asn His Thr Gly Ser Val Pro Val Asp Pro Thr
305                 310                 315                 320

Phe Met Tyr Lys Asn Thr Pro Thr Ile Leu Ala Gln Arg Ser Gly Val
                325                 330                 335

Pro His Met Val Arg Gly Arg Tyr Met Phe Arg Val Asp Asp Val Val
            340                 345                 350

Arg Pro Ala Gly Cys Ser Asn Lys Thr Gly Gly Thr Tyr Pro Met Leu

-continued

```
                355                 360                 365
Ile Tyr Pro Asn Ile Ala Asn Met Leu Gly Glu Thr Ser Val Asp Val
370                 375                 380

Asn Ala Leu Cys Leu Asp Arg Ser Gln Thr Tyr Val Leu Met Ile Glu
385                 390                 395                 400

Gln Arg Gln Thr Ala Ser Cys Thr Val Ile Asn Ser Ala Ile Ala Arg
                405                 410                 415

Cys His Leu Pro Lys Ile Tyr Asp Trp Gly Thr Lys Thr Val Tyr Phe
            420                 425                 430

Gln Pro Gln Ser Gly Ser His Gln Glu Asp Lys Ala Phe Val Gly Tyr
            435                 440                 445

Ile Tyr Phe Val Pro Pro Thr Leu Asp Pro Met Arg Leu Asp Ile Gly
            450                 455                 460

Asn Val Tyr Glu Trp Phe Arg Asn Pro Ile Leu Lys Val Ile Pro
465                 470                 475                 480

Ile Thr Trp Tyr Pro Arg Asn Phe Thr Asn Pro Asp Leu Asp Tyr Lys
                485                 490                 495

Asp Tyr Asn Ile Arg Ile Ser Asp Asn Gln Leu Tyr Ser Val Gln Leu
            500                 505                 510

Gly Leu Tyr Val Ile Gly Tyr Arg Glu Ala Ala Asp Gln Ile Lys
            515                 520                 525

Lys Phe Arg Pro Glu His Arg Val Leu Cys Arg Leu Ala Thr Tyr Thr
            530                 535                 540

Asn Arg Asn Ser Pro Asp Tyr Arg Trp Lys Pro Gln Glu Lys Ile
545                 550                 555                 560

Asn Leu Tyr Gln Val Glu Lys Trp Tyr Leu Thr Asp Trp Glu Arg Thr
                565                 570                 575

Asn Thr Leu Tyr Ser Tyr Arg Phe Gly Tyr Leu Lys Leu Ala Pro Val
            580                 585                 590

Thr Ala Asn Glu Asp Thr Ser Gln His Leu Thr His Leu Pro Ser Gly
            595                 600                 605

Leu Val Ser Pro Pro Ile Ser Ile His Trp Leu Trp Thr Ile Asn Asn
            610                 615                 620

Pro Gln Phe Val Ser Ser Thr Tyr Ser Gln Gln Asp Ala Glu Ser Arg
625                 630                 635                 640

Met His Phe Val Ser Thr Lys Ala Thr Glu Ile Cys His Asp Trp Phe
                645                 650                 655

Ala Glu Asp Gly Ala Gln Tyr Asn Phe Ile Arg Asp Thr Glu Thr Asn
            660                 665                 670

Ala Ser Cys Pro Cys Val Glu Ser Gln Ala Arg Val Asp Ile Gly Arg
            675                 680                 685

Phe Met Pro His Pro Arg Cys Ser Gln Ile Phe Arg Asp Ile Thr Cys
            690                 695                 700

Gln Thr Met Ile Gly Ala Lys Asn Cys Tyr Met Ser Ala Gln Asn Ile
705                 710                 715                 720

Tyr Gly Ser Tyr Ala Gly Glu Gly Ser Gly Tyr Glu Ser Glu Lys Thr
                725                 730                 735

Ala Arg Phe Gln Thr His Tyr Gly Gln Val Cys Cys Tyr Asp Glu Glu
            740                 745                 750

Gly Lys Leu Met Gln Thr Ser Tyr Gln Pro Val Ile Lys Val Thr Asp
            755                 760                 765

Asp Thr Pro Tyr Asn Pro Gly Tyr Pro Leu Arg Ala Tyr Glu Phe Gly
            770                 775                 780
```

```
Thr Asp Pro Tyr Ile Gly Gln Phe Glu Ala Lys Phe Lys Ser Leu
785                 790                 795                 800

Ser Val Phe Tyr His Asp Tyr Met Pro Tyr Phe Cys Cys Lys Tyr
            805                 810                 815

Ala Lys Phe Arg Cys Gln Leu Phe Tyr Trp Arg Arg Pro Ser Ser Gly
            820                 825                 830

Cys Gln Gln Tyr Gln Pro Pro Ala Val Gly Glu Ala Leu Gly Ala Val
            835                 840                 845

Ser Phe Asn Thr Ile Asp Asn Asp Lys Phe Ile Phe Asn Glu Pro Gly
850                 855                 860

Val Phe Thr Phe Leu Tyr Ile Pro Lys Thr Val Thr Thr Pro Glu Val
865                 870                 875                 880

Arg Ile Gln Val Arg Leu Glu Arg Tyr Pro Asp Arg Arg Val Asp Phe
                885                 890                 895

Ser Leu Leu Gly Arg Gln Ile Gly Gln Ala Asn Leu Val Gln Pro Thr
                900                 905                 910

Asn Ala Thr Val Ile Thr Gly Ile Ala Ile Glu Ala Thr Gly Thr Asp
                915                 920                 925

Arg Val His Val Val Ala Arg Lys Asp Thr Arg Arg Phe Arg Tyr Arg
    930                 935                 940

Thr Ser Ile Ile Val Gly Asn Ile Leu Arg Tyr Phe Asp Val Met Arg
945                 950                 955                 960

Ile Gln Arg Phe Arg Gly Val Met Val Tyr Val Asn Asn Val Glu Arg
                965                 970                 975

Gly Gln Pro Glu Ile Tyr Val Val Leu Glu Glu Ala Gln Ile Gly Ile
                980                 985                 990

Arg Ile Arg Glu Ser Tyr Asn Leu Asp Ile Asp Arg Leu Ser Met Tyr
                995                 1000                1005

Gln Glu Ser Met Gly Leu Leu Asp Ile Glu Leu Ser Val Pro Pro
    1010                1015                1020

Gln Tyr Gly Val Arg Pro Asp Gly Asp Lys Ala Arg Glu Gln Asp
    1025                1030                1035

Met Arg Thr Arg Tyr Asn Phe Pro Arg Val Ser Gly Leu Met Arg
    1040                1045                1050

Pro Phe Pro Asp Gln Thr Ser Ala Ser Tyr Leu Ser Gly Leu Ser
    1055                1060                1065

Leu Ser Asp Val Asn Ala Glu Gly Ile Arg Gln Gln Ile Ile Ser
    1070                1075                1080

Asn Tyr Leu Ile Pro Gly Thr Gly Asp Ser Arg Gln Thr Met Gly
    1085                1090                1095

Thr Leu Asn Gln Asn Ile Pro Thr Asp Asn Met Phe Thr Thr Ser
    1100                1105                1110

Gln Asp Ile Asp Lys Lys Phe Glu Val Phe Pro Glu Val Tyr Ile
    1115                1120                1125

Lys Ser Glu Pro Ile Tyr Lys Thr Ser Ala Glu Tyr Glu Thr Gly
    1130                1135                1140

Arg Tyr Arg Phe Val Pro Met Thr Gly Gln Met Leu Ser Gln Arg
    1145                1150                1155

Leu Gln Thr Cys Arg Asp Leu Gln Leu Ser Asp Arg Thr Asn Trp
    1160                1165                1170

Gln Pro Leu Gln Asn Leu Tyr Glu Gln Gln Tyr Gly Ile Asp Tyr
    1175                1180                1185
```

```
Cys Pro Asp Asn Pro Ser Gln Ile Ile Gln Glu Cys Gly Asp Ser
    1190                1195                1200

Val Ser Cys Leu Asn Asp Tyr Met Leu Phe Asn Ala Arg Leu Leu
1205                1210                1215

Gly Met Glu Ala Gln Asn Asn Trp Asn Ser Phe Ser Asn Asp Arg
    1220                1225                1230

Met His Ala Ser Arg His Tyr Asn Ser Cys Gly Pro Ile Met Ile
    1235                1240                1245

Glu Tyr Pro Glu Tyr Leu Met Lys Thr Pro Val Leu Ser Ser Gly
    1250                1255                1260

Tyr Leu Glu Gly Asp Val Ala Arg Phe Asp Cys Phe Gln Thr His
    1265                1270                1275

Trp Ile Lys Gly Asp Tyr Glu Tyr Lys Cys Gly Ile Val Val Asp
    1280                1285                1290

Tyr Asn Asp Pro His Ser Tyr Arg Phe Glu Trp Asn Lys Gly Ser
    1295                1300                1305

Gln Pro Trp Cys Arg Ser Arg Glu Lys Asp Asn Leu Phe Lys Trp
    1310                1315                1320

Leu Thr Gly Ile Phe Ser Thr Ile Gly Ile Ile Met Ala Ile Val
    1325                1330                1335

Phe Ile Phe Leu Cys Cys Trp Thr Leu Lys Gln Lys Arg Arg His
    1340                1345                1350

Gln Ala Glu Glu Lys Ile Ser Ser Leu Tyr Lys Val Pro Ile Arg
    1355                1360                1365

Gly Ser Met Val Ser Arg Asp Trp Arg Ser Ser Glu Thr Arg Pro
    1370                1375                1380

Phe Thr Lys Ala Arg Thr Asp Ser Met Ser Ser Glu Thr Asn Gly
    1385                1390                1395

Met Tyr His Gly Asn Glu His Asp Ser Gln Tyr Arg Gly Gly Pro
    1400                1405                1410

Ile Gly Gly Thr Val Pro Ile Val Val Asp Gly Ser Gly Gly Tyr
    1415                1420                1425

Arg Gly Glu Thr Asn Gly Gln Tyr Arg Ala Val Asp Ala Ile Ala
    1430                1435                1440

Pro Tyr Pro Glu Gln Tyr His Glu Ser Val Pro Asn Leu Ser Arg
    1445                1450                1455

Arg Pro Ser Ser Pro Val Lys Thr Thr Val Ile Arg Asn Asn Lys
    1460                1465                1470

Thr Val Pro Ala Gly Pro Gln Ser Thr Ser Ser Thr Pro Pro Val
    1475                1480                1485

Pro Val His Ser Arg Ile Ile Gly Glu Gln Asn Gly Ser Asp His
    1490                1495                1500

Thr Gln Leu Leu Gly Leu Asn Thr Ser Val
    1505                1510

<210> SEQ ID NO 12
<211> LENGTH: 577
<212> TYPE: PRT
<213> ORGANISM: Brugia malayi
<220> FEATURE:
<221> NAME/KEY: MISC_FEATURE
<223> OTHER INFORMATION: >gi|170592623|ref|XP_001901064.1| EGF-like
      domain containing protein [Brugia malayi]

<400> SEQUENCE: 12

Met Val Lys Ile Gly Lys Lys Lys Cys Glu Cys Asn Leu Asn Thr Gly
```

```
1               5                   10                  15
Ser Gln Cys Asn Pro Val Thr Gly Lys Cys Ile Cys Ala Ala Gly Tyr
                20                  25                  30
Gln Gly Ile Arg Cys Asp Glu Lys Cys Pro Glu Gly Leu Phe Gly Met
                35                  40                  45
Asp Cys Lys Ser Lys Cys Asn Cys Lys Asn Gly Ala Ser Cys Asp His
        50                  55                  60
Arg Phe Gly Thr Cys Lys Cys Thr Ala Gly Trp Arg Gly Pro Gln Cys
65                  70                  75                  80
Asn Leu Pro Cys Trp Gly Gly His Gly Asn Thr Glu Cys Arg Val Cys
                    85                  90                  95
Ser Cys Lys Asn Gly Ala Gly Cys Asn Pro Leu Thr Gly Ala Cys Ile
                100                 105                 110
Cys Pro Ala Gly Trp Thr Gly Lys Ser Cys Asp Val Pro Cys Ser Lys
            115                 120                 125
Asp Phe Tyr Gly Ile Asn Cys Ser Gln Glu Cys Arg Cys Trp Asn Gly
        130                 135                 140
Ala Thr Cys Asp Pro Ile Asn Gly Glu Cys Ser Cys Ala Asp Gly Trp
145                 150                 155                 160
Ala Gly Pro Asp Cys Ser Val Leu Cys Pro Leu Glu Glu Lys Glu Asn
                165                 170                 175
Cys Leu Asp Ser Cys Pro Cys Val His Gly Ile Cys Met Gly Asp Ser
            180                 185                 190
Gly Lys Cys Asp Cys Arg Pro Gly Tyr Ala Gly Arg Leu Cys Asp Arg
        195                 200                 205
Lys Cys Pro Phe Gly Tyr Tyr Gly Glu Lys Cys Ala Gln Arg Cys Ala
    210                 215                 220
Cys Lys His Gly Cys Asn Pro Phe Thr Gly Glu Cys Leu Gln Cys Pro
225                 230                 235                 240
Pro Gly Arg Ser Gly Val Leu Cys Glu Gln Ser Cys Pro Phe Lys Thr
                245                 250                 255
Trp Gly Asp Lys Cys Met Asn His Cys Asn Cys Ala Glu Ser Ala Glu
                260                 265                 270
Cys Asp Ser Ile Asp Gly Ser Cys Gln Cys Tyr His Gly Phe Thr Gly
            275                 280                 285
Ala Arg Cys Asp Leu Glu Cys Pro Thr Gly Lys Trp Gly Met Asn Cys
        290                 295                 300
Ser Gln Thr Cys Asn Lys Cys Lys Asn Lys Gly Glu Cys Asp Pro Ile
305                 310                 315                 320
Asp Gly Glu Cys His Cys Ala Pro Gly Phe Met Gly Lys Cys Glu
                325                 330                 335
Leu Asn Val Gln Val Ile Ala Lys Leu Cys Asn Pro Val Asn Gly Ile
                340                 345                 350
Cys His Cys Ala Ala Gly Leu Met Gly Asp Leu Cys Asn Gln Tyr Cys
            355                 360                 365
Pro Glu Gly Ser Trp Gly Pro Asp Cys Val Phe Arg Phe Cys Pro Glu
        370                 375                 380
Gly Phe Trp Gly Glu Gln Cys Ala His Val Cys Asp Cys Gly Glu Asp
385                 390                 395                 400
Ile Cys Asn Pro Val Ile Gly Cys Cys Lys Lys Asn Asp Leu Ser Cys
                405                 410                 415
Asp Pro Thr Lys Leu Lys His Leu Pro Lys Glu Arg Thr Thr Val Val
                420                 425                 430
```

-continued

```
Ile Met Ser Ser Ile Val Ser Gly Leu Tyr Val Ile Met Ile Leu
        435                 440                 445

Leu Ile Leu Val Phe Tyr Tyr Arg Arg Lys Tyr Val Lys Glu Arg Gly
450                 455                 460

Pro Thr Ile Pro Ile Ile Thr Tyr His Pro Thr Val Thr Asn Ser Glu
465                 470                 475                 480

Pro Ile Ser Thr Lys Asn Gly Phe Asn Asn Pro Leu Tyr Arg Lys Ser
                485                 490                 495

Ala Arg Ile Ala Thr Asn Asp Gln Leu Ala Gly Lys Asn Asn Lys Phe
                500                 505                 510

Glu His Leu Ala Asn Lys Glu Gln Ser Asp Arg Leu Gln Asn Asp Tyr
                515                 520                 525

Ala Lys Phe Asp Asp Phe Tyr Ala Glu Ile Asp Pro Ser Phe Asp Asn
530                 535                 540

Gly Lys Asn Leu Glu Asn Ser Ile Lys Gly Val Tyr Asp Tyr Gly Ile
545                 550                 555                 560

Ile Lys Glu Gln Leu Asn Tyr Lys Val Thr Thr Lys Ser Ser Leu
                565                 570                 575

Glu
```

<210> SEQ ID NO 13
<211> LENGTH: 1061
<212> TYPE: PRT
<213> ORGANISM: Brugia malayi
<220> FEATURE:
<221> NAME/KEY: MISC_FEATURE
<223> OTHER INFORMATION: >gi|170588703|ref|XP_001899113.1| Peptidase family M1 containing protein [Brugia malayi]

<400> SEQUENCE: 13

```
Met Ile Ser Glu Arg Asn Ser Leu Lys Asn Ser Pro Asn Asp Asp Thr
1               5                   10                  15

Glu Leu Trp Asn Val Asn Asp Ala Ser Ser Ile Ile Ile Ser Pro Gly
                20                  25                  30

Thr Met Asp Ser Phe Ser Ser His Tyr Ser Phe Leu Asn Lys Lys Cys
            35                  40                  45

Ser Ser Trp Leu Gly Lys Ser Ile Leu Leu Ser Leu Met Leu Thr Val
50                  55                  60

Phe Val Phe Gly Val Leu Leu Ala Phe Leu Ile Gly Gln Trp Val Ala
65                  70                  75                  80

Lys Ser Glu Lys Asn Ala His Lys Val Glu Asn Ser Glu Glu Ala Val
                85                  90                  95

Met Lys Asn Ile Thr Leu Leu Ser Val Tyr Pro Pro Leu Ser Asn Ser
                100                 105                 110

Ile Thr Pro Trp Ala Leu His Phe Ser Leu Ser Ser Ala Thr Ala Gln
            115                 120                 125

Lys His Arg Lys Val Pro Leu Ile Arg Leu Pro Arg Ala Leu Gln Pro
        130                 135                 140

Glu His Tyr Asp Leu Gln Leu Asp Phe Thr Asn Val Val Ser Lys Glu
145                 150                 155                 160

Gln Ile Ser Gly Asn Ile Ser Ile Leu Leu Lys Ser Tyr Val Asn Ser
                165                 170                 175

Thr Thr Leu His Glu Val Ala Phe His Ala Ala Asn Val His Ile
            180                 185                 190

Asp Gly Val Arg Leu Leu His Gln Gly Lys Val Val Arg Ile Glu Arg
```

-continued

```
            195                 200                 205
Phe Lys Arg Glu His Arg Ala Lys Val Ile Arg Leu Gln Leu Glu Gln
210                 215                 220
Pro Leu Lys Asn Gly Trp Tyr Met Leu Glu Met Gln Phe Val Thr Lys
225                 230                 235                 240
Ile Cys Lys Asp Asn Ser Gly Val His Cys Tyr Arg Gly Ile Arg
                245                 250                 255
Gln Asp Val Asn Ser Leu Pro Arg Asn His His Leu Pro Ile Ile Ser
                260                 265                 270
Phe Thr Thr Arg Phe Gln Pro Leu Leu Ala Arg Thr Phe Phe Pro Cys
            275                 280                 285
Trp Asp Glu Pro Ser Trp Lys Ala Ile Tyr Asn Ile Thr Ile Leu His
            290                 295                 300
Ser Thr Ser Ile Thr Val Leu Thr Asn Ala Ala Pro Leu His Phe Ile
305                 310                 315                 320
Gln Lys Gln Arg His Ser Phe Val Arg Thr Thr Phe Arg Glu Thr Pro
                325                 330                 335
Pro Ile Pro Ala Phe Leu Leu Ala Phe Ala Phe Gly Pro Tyr Ser Asn
                340                 345                 350
Leu Glu Arg Ser Thr Gly Tyr Asp Val Pro Leu Thr Ile Trp Thr Phe
            355                 360                 365
Pro Glu Asp Leu Val Tyr Ala Lys Phe Ala Ala Asn Phe Ser Pro Tyr
            370                 375                 380
Met Phe Asp Gln Leu Ala Lys Glu Phe Val Val Pro Tyr Pro Leu Ser
385                 390                 395                 400
Lys Ile Asp Phe Val Ala Ala His Ser Phe Pro Val Ser Gly Met Glu
                405                 410                 415
Asn Trp Gly Leu Ile Val Phe Gln Lys Glu Leu Phe Leu Leu Asp Ser
                420                 425                 430
Leu Leu Glu Ser Ser Ala Asn Met Thr Val Asp Leu Leu Ala Glu Gln
            435                 440                 445
Tyr Asp Ile Glu Lys Ile Ile Thr His Glu Leu Val His Gln Trp Phe
            450                 455                 460
Gly Asn Leu Val Thr Ile Asn Asp Trp Ser Glu Leu Trp Leu Ser Glu
465                 470                 475                 480
Gly Phe Ala Ser Tyr Tyr Val Asn Tyr Leu Leu Lys Lys Gln Arg Pro
                485                 490                 495
Ile Leu Ala Thr Asn Glu Tyr Phe Leu Arg Leu Ser Gln Leu Leu Ser
                500                 505                 510
Arg Gln Thr Ser Ser Glu Lys Val Ala Leu Val Lys Val Phe Lys Thr
            515                 520                 525
Glu Glu Val Glu Asn Ala Phe Asn Pro Tyr His Leu Tyr Thr Lys
            530                 535                 540
Gly Ala Val Ile Val Lys Met Met Cys Asp Leu Val Gly Lys Asp Asn
545                 550                 555                 560
Phe Arg Glu Gly Val Arg Arg Phe Leu Lys Thr Asn Ala Tyr Lys Ser
                565                 570                 575
Ile Gly Arg Ser Ala Leu Trp Lys Ala Met Pro Ala Tyr Thr Asp His
                580                 585                 590
Gly Leu Gln Asn Lys Lys Leu Glu Asn Val Ile Glu Pro Trp Leu Leu
            595                 600                 605
Asn Asp Gly Met Pro Glu Val Leu Val Ser Glu Pro Asp Leu Ser Arg
610                 615                 620
```

```
Asn Tyr Asp Tyr Gly Ser Ile Arg Leu Ile Pro Arg Pro Ser Asp Gln
625                 630                 635                 640

Asn Arg Tyr Val Thr Tyr Leu Arg Gly Ala Ser Thr Arg His Tyr Asn
            645                 650                 655

Val Lys Tyr Ser Lys Glu Thr Ile Lys Lys Val Arg Met Lys Lys Trp
                660                 665                 670

Ile Gly Arg Ser Lys Lys Ile Glu Val Gly Asn Ala Asn Glu Lys Ser
            675                 680                 685

Tyr Phe Tyr Val Glu Ser Val Asn Lys Gln Arg Ser Ile Glu Asn Ile
690                 695                 700

Trp Thr Asn Ser Lys Lys Gln Ala Ala Lys Ser Lys Gln Ile Val Asp
705                 710                 715                 720

Gly Asp Gln Ser Ile Ser Arg Lys Lys Glu Arg His Tyr Arg Lys Ile
                725                 730                 735

Lys Glu Asn Arg Arg Ser Val Arg Glu Lys Gln Phe Trp Ser Ile Pro
                740                 745                 750

Phe Ser Tyr Gln Leu Ser Ser Lys Thr Asn Val Phe Ala Asp Thr Ile
            755                 760                 765

Arg Glu Phe Trp Leu His Asn Lys Thr Val Val Leu Thr Asp Lys Lys
770                 775                 780

Tyr Gln Thr Ser Ala Ala Leu Leu Ala Asn Val Asn Trp Lys Tyr Pro
785                 790                 795                 800

Tyr Arg Val Asn Tyr Asp Ile Glu Asn Trp Lys Met Leu Ala Lys Leu
                805                 810                 815

Val Thr Glu Trp Leu Asn Lys Val Met Asp Asp Thr Lys Ala Lys Pro
            820                 825                 830

Glu Leu Ala Ala Leu Trp Leu Leu Asp Ala Asn Arg Leu Ile Gln Phe
                835                 840                 845

Tyr Lys Leu Arg Cys Ala Val Asn Leu Ser Thr Cys Asp Pro Glu His
850                 855                 860

Lys Val Gln Gln Trp Leu Lys Ser Gly Gly Leu Thr Lys Gly Asp His
865                 870                 875                 880

Tyr Ser Gln Met Thr Ala Ile Cys His His Leu Phe Thr Gln Gly Thr
                885                 890                 895

Lys Asp Gly His Asp Val Val Glu Asn Gly Leu Lys Gln Phe Ser Gly
            900                 905                 910

Lys Trp Thr Thr Thr Ile Gln Leu Ala Thr Cys Val Arg Asn Glu His
            915                 920                 925

Ile Leu Lys Lys Val Ala Ser Gln Ile Ile Ala Thr Arg Asn Ala Ala
930                 935                 940

Val Tyr Thr Ala Met Leu Gln Asn Glu Phe Thr Leu Leu Tyr Asn Lys
945                 950                 955                 960

Lys Phe Arg Ala Leu Phe Trp Lys Glu Ile Ala Asp Met Pro Leu Ile
                965                 970                 975

Glu Arg Lys Leu Leu Phe Ser Thr Gly Thr Asp Gln Thr Ala Gln Val
            980                 985                 990

Ala Gln Thr Leu Val His Ser Ile Arg Ser Phe Ser Glu Leu Glu Trp
            995                 1000                1005

Leu Val Asn Ile Val Pro Asp Trp Gly Pro Tyr Met Lys Pro His
    1010                1015                1020

Ile Asp Tyr Leu His Arg Lys Phe Gln Trp Ile Asp Glu Ile Ala
    1025                1030                1035
```

```
Thr Pro Arg Ile Glu His Phe Leu Leu Lys Val Ile Lys Ala Val
    1040                1045                1050

Lys Lys Lys Ser Val Thr Ala Arg
    1055                1060

<210> SEQ ID NO 14
<211> LENGTH: 169
<212> TYPE: PRT
<213> ORGANISM: Brugia malayi
<220> FEATURE:
<221> NAME/KEY: MISC_FEATURE
<223> OTHER INFORMATION: >gi|170576544|ref|XP_001893672.1| MGC84665
      protein [Brugia malayi]

<400> SEQUENCE: 14

Met Cys Leu Leu Pro Ser Arg Ile Leu Tyr Arg Cys Glu Trp Leu Arg
1               5                   10                  15

Met Leu Ala Ser Thr Ile Met His Val Asp Asp Met His Leu Tyr Phe
            20                  25                  30

Asn Met Ile Ser Leu Leu Trp Lys Gly Arg Arg Leu Glu Pro Trp Leu
        35                  40                  45

Gly Ser Asn Arg Phe Leu Leu Leu Ala Val Phe Ala Val Ala Thr
    50                  55                  60

Ser Ser Thr Met Val Gly Leu Ser Tyr Leu Ala Asp Glu Val Phe Ser
65                  70                  75                  80

Phe Asn Gly Gly Gly Tyr Met Asn Gln Cys Ala Ile Gly Phe Ser Gly
                85                  90                  95

Ser Ile Pro Lys Ser Phe Ser Gln Thr Arg Asn Arg Thr Arg Ser Asn
            100                 105                 110

Asn Arg Asn Trp Phe Thr Asn Leu Ser Phe Gly Gly Arg Asn Ser Ala
        115                 120                 125

Ala Tyr Glu Arg Pro Ser Tyr Gly Trp Glu Asn Gln Arg Asn Phe
    130                 135                 140

Asn Glu Tyr Thr Gly Gly Met Ser Glu Glu Gln Leu Trp Arg Ala
145                 150                 155                 160

Thr Gln Arg Ser Leu Tyr Glu Asp Ser
                165

<210> SEQ ID NO 15
<211> LENGTH: 845
<212> TYPE: PRT
<213> ORGANISM: Brugia malayi
<220> FEATURE:
<221> NAME/KEY: MISC_FEATURE
<223> OTHER INFORMATION: >gi|170594653|ref|XP_001902078.1| Reprolysin
      [Brugia malayi]

<400> SEQUENCE: 15

Met Gln Asp Gly Ile Tyr Cys Pro Leu His Ile Tyr Tyr Gly Glu Lys
1               5                   10                  15

Glu Leu Asn Ala Asn Gly Leu Ile Ser Ile Ser His Thr Val Arg Pro
            20                  25                  30

Thr Phe Glu Leu Arg Leu Gln Asn Asp Val Gly Glu Ser Arg Asn Phe
        35                  40                  45

Val Phe Gln Pro Asn Arg Glu Leu Leu Lys Thr Ala Gly Lys Thr Ala
    50                  55                  60

Leu Asn Asn Leu Thr Phe Ser Val Asn Thr Lys Ile His Leu Asp Asn
65                  70                  75                  80

Val Lys Gly Ile Lys Arg Thr Ser Leu Val Asn Gln Ile Phe Arg Gly
```

-continued

```
                85                  90                  95
Leu Phe Thr Ile Asn Gly Arg Arg Phe Val Leu Gly Ala Asn Pro Asn
                100                 105                 110
Ala Ser Phe His Phe Val Pro Leu Ser Asp His Ser Cys Asp Trp Gly
                115                 120                 125
Leu Arg Ser Lys Arg Ser Ile Gly Gly Ser His Thr Ala Glu Tyr Tyr
                130                 135                 140
Ala Gln Phe Leu Asp Asp Arg Trp Arg Tyr Val Glu Leu Ala Leu Ile
145                 150                 155                 160
Ala Asp Lys Leu Val Phe Glu Lys Tyr Asp Ser Asn Val Thr Glu Val
                165                 170                 175
Met Gln Arg Leu Asn Ala Ile Thr Ser Tyr Ile Asn Ser Leu Tyr Met
                180                 185                 190
Pro Ile Asn Ile Arg Val Val Leu Val Trp Ala Asp Val Trp Thr Asn
                195                 200                 205
Ser Asn Gln Val Asp Ile Thr Ser Asn Ser Asp Thr Thr Leu Trp Asn
210                 215                 220
Phe Leu Asn Trp Arg Lys Thr Leu Leu Lys Asp His Pro His Asp Asn
225                 230                 235                 240
Ala His Leu Leu Thr Gly Val Val Phe Glu Asn Asn Val Val Gly Lys
                245                 250                 255
Ala Phe Lys Gly Thr Met Cys Ser Tyr Asp Phe Ser Gly Gly Val Asp
                260                 265                 270
Met Glu His Ser Asp Gln Ala Ala Phe Val Ala Ala Thr Ile Ala His
                275                 280                 285
Glu Met Gly His Asn Phe Gly Met Glu His Asp Ile Asp Glu Val Glu
                290                 295                 300
Cys Arg Cys Pro Ala Lys Ser Cys Ile Met Ser Pro Ser Thr Gly Ile
305                 310                 315                 320
Ile Arg Pro Thr Phe Trp Ser Glu Cys Ser Met Arg Ala Leu Gln His
                325                 330                 335
Ser Phe Ser Arg Gly Val Asp Tyr Cys Leu Arg Asn Ser Pro Thr Ser
                340                 345                 350
Val Phe Gly Gly Ala Arg Cys Gly Asn Gly Ile Val Glu Val Gly Glu
                355                 360                 365
Glu Cys Asp Cys Gly Thr Pro Ser Ser Cys Ile Asn Lys Cys Cys Asn
                370                 375                 380
Pro Val Thr Cys Gln Leu Ala Glu Ala Val Cys Ala Ser Gly Glu
385                 390                 395                 400
Cys Cys Asp Leu Asn Thr Cys Gln Met Leu Pro Ala Thr Thr Asp Phe
                405                 410                 415
Cys Tyr Asn Gly Tyr Cys Gly Ser Arg Asp Ala Gln Cys Gln Tyr Ile
                420                 425                 430
Trp Gly Arg Thr Gly Arg Asp Ala Ala Pro Val Cys Tyr Asp Leu Asn
                435                 440                 445
Leu Tyr Gly Ser Ser Gly Gly Asn Cys Gly Phe Leu His Glu Thr Asn
                450                 455                 460
Arg Phe Val Pro Cys His Lys Asn Asn Ile Lys Cys Gly Arg Leu His
465                 470                 475                 480
Cys Ile His Glu Asn Glu Lys Leu Ala Phe Gly Asp Pro Ser Thr Val
                485                 490                 495
Tyr Thr Ser Tyr Thr Gly Leu Lys Leu Ser Ser Gly Glu Asp Val Ala
                500                 505                 510
```

Cys Arg Val Ile Trp Thr Lys Tyr Ile Ser Gly Gln Lys Glu Pro Asp
            515                 520                 525

Pro Gly Met Val Pro Asp Gly Ala Phe Cys Gly Gln Asp Lys Met Cys
        530                 535                 540

Val Asp Ala Lys Cys Gln Asn Arg Thr Ala Lys Val Leu Met Ala Pro
545                 550                 555                 560

Lys Cys Glu Pro Val Ser Cys Asn Asn Ala Gly Ile Cys Asn Asn Met
                565                 570                 575

Gly Asn Cys His Cys Asp Pro Gly Tyr Gly Pro Ser Cys Ala Ile
            580                 585                 590

Pro Gly Pro Gly Gly Ser Val Asn Ser Gly Pro Ala Ile Glu Gly Gly
        595                 600                 605

Val Ile His Val Gly Phe Val Val Phe Trp Leu Leu Leu Ile Leu Thr
        610                 615                 620

Ile Thr Phe Ile Gly Ile Ser Ile Ile Val Lys Arg Lys Arg Asp Phe
625                 630                 635                 640

Trp Leu His Lys Glu Ile Trp Glu Lys Leu Lys Lys Ala Leu Lys Ile
                645                 650                 655

Glu Lys Leu Leu Val Pro Ile Arg Lys Ala Pro Pro Pro Arg Ser
            660                 665                 670

Thr Ile Arg Thr Ala Asp Leu Asn Leu Ile Trp Gly Asp Thr Ala Ser
        675                 680                 685

Asp Ala Leu Arg Val Arg Ser Tyr His Gln Pro Leu Pro Ser Ile
        690                 695                 700

Ser Pro Pro Val Val Pro Ser Thr Thr Leu Asn Leu Val Pro Thr Lys
705                 710                 715                 720

Pro Ser Val Ile Ala Tyr Arg Asn Ser Met Arg Pro Thr Thr Ala Pro
                725                 730                 735

Pro Lys Val Pro Gln Arg Pro Ser Glu Ala Leu Gln Ala Leu Tyr
            740                 745                 750

Ala Glu Lys Gly Glu Glu Leu Ser Met Asn Leu Thr Lys Gln Thr Ser
        755                 760                 765

Pro Met Tyr Cys Ile Pro Ser Glu Ala Asn Ala Val Lys Arg Ile Glu
        770                 775                 780

Thr Glu Thr Phe Arg Pro Val Gln Ala Pro Pro Leu Pro Pro His His
785                 790                 795                 800

Asn His Val Leu Ala Lys Asn Asn Ala Leu Ser Asp Asn Arg Asp Lys
                805                 810                 815

Pro Leu Leu Ala Val Lys Pro Ser Ser Val Lys Asp Ile Ala Ala Arg
            820                 825                 830

Phe Asp Pro Lys Thr Ser Gln Val Ser Thr Lys Phe Ile
            835                 840                 845

<210> SEQ ID NO 16
<211> LENGTH: 264
<212> TYPE: PRT
<213> ORGANISM: Brugia malayi
<220> FEATURE:
<221> NAME/KEY: MISC_FEATURE
<223> OTHER INFORMATION: >gi|170571016|ref|XP_001891567.1| ShTK domain
      containing protein, partial [Brugia malayi]

<400> SEQUENCE: 16

Asn Lys Tyr Gln Arg Lys Met Phe Ser His Ile Val Ala Thr Met Ser
1               5                   10                  15

```
Ile Ile Phe Ile Thr Leu Ala Phe Ala Ala Asn Gln Val Cys Glu Asp
             20                  25                  30

Met Tyr Asn Gln Cys Glu Ser Thr Ile Cys Thr Asp Pro Met Ala Lys
         35                  40                  45

Glu Ile Cys Ala Lys Thr Cys Gly Phe Cys Glu Met Thr Thr Ser Thr
     50                  55                  60

Ala Val Thr Pro Val Cys Asp Asp Ala Tyr Asn Gln Cys Asp Ser Thr
65                  70                  75                  80

Ile Cys Thr Met Pro Ile Ala Ser Glu Ile Cys Ala Lys Thr Cys Gly
             85                  90                  95

Phe Cys Gly Val Ala Pro Ser Thr Ala Val Thr Pro Val Cys Asp Asp
            100                 105                 110

Leu Phe Asp Gln Cys Asp His Thr Val Cys Thr Ile Pro Met Ser Lys
            115                 120                 125

Glu Ile Cys Ala Arg Thr Cys Gly Phe Cys Gly Thr Thr Pro Leu Val
        130                 135                 140

Thr Val Thr Pro Ala Cys Glu Asp Leu Tyr Asn Gln Cys Glu Ser Ala
145                 150                 155                 160

Ile Cys Thr Thr Pro Ile Ala Asn Asp Ile Cys Ala Arg Thr Cys Gly
            165                 170                 175

Phe Cys Gly Thr Thr Pro Ser Thr Ala Ser Thr Ile Pro Val Cys Glu
            180                 185                 190

Asp Lys Tyr Ser Lys Cys Lys Ser Asn Met Asn Cys Thr Asn Ala Leu
            195                 200                 205

Ala Lys Glu Leu Cys Ala Lys Thr Cys Gly Phe Cys Asp Asn Asp Ser
210                 215                 220

Met Pro Thr Pro Glu Glu Cys Ser His Leu Cys Gln Pro Leu Gln Ser
225                 230                 235                 240

Leu Cys Thr Phe Val Gly Trp Ile Met Gly Pro Ile Thr His Gly Phe
            245                 250                 255

Cys Leu Arg Cys Gln Gln Cys Lys
            260

<210> SEQ ID NO 17
<211> LENGTH: 369
<212> TYPE: PRT
<213> ORGANISM: Brugia malayi
<220> FEATURE:
<221> NAME/KEY: MISC_FEATURE
<223> OTHER INFORMATION: >gi|170575897|ref|XP_001893428.1| serpin
      [Brugia malayi]
<220> FEATURE:
<221> NAME/KEY: misc_feature
<222> LOCATION: (212)..(212)
<223> OTHER INFORMATION: Xaa can be any naturally occurring amino acid

<400> SEQUENCE: 17

Met Lys Asn Gln Thr Ile Thr Ala Ile Phe Val Leu Val Ala Ser Ala
1               5                   10                  15

Gln Phe Ile Ser Ile Leu Gly Gln Ile Ser Leu Thr Glu Arg Ala Gln
            20                  25                  30

Leu Asp Phe Ala Val Ser Leu Leu Gln Asn Val Ala Glu Ser Asp Lys
         35                  40                  45

Ser Ser Val Leu Ser Pro Phe Ser Val Ser Thr Ser Leu Phe Ile Ala
     50                  55                  60

Tyr Leu Ala Ala Asp Gly Glu Thr Lys Gln Gln Leu Gln Ser Ala Leu
65                  70                  75                  80
```

```
Gly Lys Asp Ala Ser Ile Pro Glu Phe Arg Leu His Phe Ile Lys Gln
                85                  90                  95

Leu Ala Tyr Ile Ala Glu Ala Asn Arg Asn Tyr Thr Leu Ser Val
            100                 105                 110

Ala Asn Arg Leu Tyr Val Arg Glu Gly Leu Ser Val Lys Glu Ser Phe
            115                 120                 125

Gln Arg Val Leu Ser Phe Tyr Tyr Ser Glu Thr Leu His Lys Phe Ser
        130                 135                 140

Phe Gly Gln Arg Asn Glu Leu Val Gln Gln Ile Asn Asn Trp Ile Ser
145                 150                 155                 160

Ser Glu Thr Asn Asn Lys Val Arg Asn Met Ile Thr Glu Asn Ser Ile
                165                 170                 175

Thr Lys Asp Thr Arg Met Leu Leu Met Asn Ala Ile His Phe Lys Gly
            180                 185                 190

Thr Trp Ala Val Pro Met Met Ala Lys Ser Asp Thr Val Pro Tyr Tyr
            195                 200                 205

Glu Asp Asp Xaa Val Gln Val Ile Lys Leu Pro Tyr Ile Gly Asp Glu
        210                 215                 220

Val Glu Met Val Ile Ile Leu Pro Arg Arg Phe Gly Leu Ser Asp
225                 230                 235                 240

Val Leu Gly Asn Leu Ser Gly Glu Lys Leu Leu Lys Tyr Val Asn Glu
                245                 250                 255

Ala Thr Asn Arg Ser Val Ser Ile Lys Leu Pro Arg Phe Lys Val Glu
            260                 265                 270

Glu Lys Arg Asn Leu Asn Ser Ala Leu Gln Ala Ile Gly Ile Thr Asp
        275                 280                 285

Ala Phe Ser Gly Asn Ala Asn Phe Glu Glu Leu Phe Ser Asn Ser Leu
290                 295                 300

Pro Ile Ser Ile Gly Lys Ile Ile His Gly Gly Phe Ile Glu Val Asn
305                 310                 315                 320

Glu Lys Gly Thr Glu Ser Ala Ala Ala Thr Ile Ile Glu Leu Glu Asp
            325                 330                 335

Arg Met Gly Ser Ser Lys Ile Phe Asn Ala Asn Gln Pro Phe Leu Phe
        340                 345                 350

Ala Ile Val Lys Asp Leu Lys Thr Val Leu Phe Leu Gly Gln Phe Val
        355                 360                 365
Lys

<210> SEQ ID NO 18
<211> LENGTH: 433
<212> TYPE: PRT
<213> ORGANISM: Brugia malayi
<220> FEATURE:
<221> NAME/KEY: MISC_FEATURE
<223> OTHER INFORMATION: >gi|170594317|ref|XP_001901910.1| hypothetical
      protein Bm1_52210 [Brugia malayi]

<400> SEQUENCE: 18

Met Arg Thr Tyr Ile Val Leu Ile Phe Ile Val Glu Arg Ile Phe Cys
1               5                   10                  15

Asn Asn Thr Arg Gln Arg Leu Ile Thr Leu Leu Arg Thr Asp Gln Lys
                20                  25                  30

Phe His Asp Gln Trp Val His Leu Ile Glu Leu Gln His Arg Gln Val
            35                  40                  45

His Gly Gln Asn Met Gly Ser Ala Leu Glu Glu Ile Thr Asp Leu Met
        50                  55                  60
```

```
Leu Asn Cys Met Pro Lys Leu Asp Pro Lys Leu Asp His Ile Asp Tyr
 65                  70                  75                  80

Val Cys Pro Thr Asp Ile Gln Leu Tyr Ala Glu Leu Gly Gln Leu Thr
                 85                  90                  95

Arg Tyr Cys Asn Asp Ser Ile Met Glu Leu Ile Lys Gly Arg Ala Asp
            100                 105                 110

Ser Cys Gln His Ala Ser Tyr Thr Ser Ser Phe Pro Ser Ile Val Lys
            115                 120                 125

Phe Leu Met Lys Phe Val Arg Asn Leu Thr Val Ile Glu Thr Ser Asn
130                 135                 140

Ala Thr Lys Leu Gly Asn Gln Thr Gln Tyr Leu Val Glu Gln Phe Met
145                 150                 155                 160

Glu His Arg Ser Trp Arg Asn Lys Trp Lys Leu Ile Val Ile Met Pro
                165                 170                 175

Asn Met Glu Asp Gly Glu Leu Arg Glu Pro Glu Gln Ser Ala Val Glu
            180                 185                 190

Val Met Lys Ser Ile Lys Leu Leu Tyr Glu Val Ile Pro Gln Arg Thr
            195                 200                 205

Ile Leu Ile Val Val Arg Ser Ser Thr Leu Gln Leu Trp Gln Asp Ala
210                 215                 220

Ser Asn Ala His Arg Ala Cys Gln Thr Leu Leu Glu Pro Trp Lys Leu
225                 230                 235                 240

Tyr Lys Asn Leu Asn Pro Val Ser Ile Trp Asp Gln Val Glu Lys Ile
                245                 250                 255

Cys Gly Leu His Phe Gln Ser Ser Leu Phe Thr Val Gln Ile Leu Pro
            260                 265                 270

Leu Leu Lys Asp Ala Ser Leu Pro Phe Leu Ser Gly Ser Ser Gln Ile
            275                 280                 285

Asp Leu Ser Leu Leu Gly His Asp Cys Val His Leu Ser Pro Arg Gly
290                 295                 300

Leu Ser Leu Leu His Ile Ala Val Trp Asn Ala Ile Leu Thr Arg Leu
305                 310                 315                 320

Pro Asp Arg Ser Gln Thr Phe Asn Phe Ser Leu Glu Arg Pro Leu Cys
                325                 330                 335

Val Asp Pro Gln Cys Pro Phe Ile Arg Thr Thr Lys Asn Ser Ala Phe
            340                 345                 350

Cys Ile Trp Asn His Gln Lys Ile Asn Glu His Gly Arg Arg Ser Glu
            355                 360                 365

Gln Leu Ile Ala Ile Ser Ile Leu Ile Ile Ala Thr Ile Leu Phe Ile
370                 375                 380

Ile Ile Leu Gly Ile Met Cys Cys Phe Arg Arg Tyr Asp Asn Lys Val
385                 390                 395                 400

Asn Glu Val Ala Glu Asn Leu Ser Lys Lys Pro Pro Val Gly Val Asp
                405                 410                 415

Trp Thr Ser Trp Lys Tyr Ile Asp Glu Asp Ser Ser Val Ser Tyr Lys
            420                 425                 430

Ser

<210> SEQ ID NO 19
<211> LENGTH: 246
<212> TYPE: PRT
<213> ORGANISM: Brugia malayi
<220> FEATURE:
<221> NAME/KEY: MISC_FEATURE
```

<223> OTHER INFORMATION: >gi|170596866|ref|XP_001902925.1| Conserved
      hypothetical protein, partial [Brugia malayi]

<400> SEQUENCE: 19

Met Ala Ile Lys Asn Glu Asn Asp Gly Lys Met Met Phe Thr Val Ile
1               5                   10                  15

Phe Ile Ala Ser Ser Leu Leu Ile Ser Thr His Cys Phe Thr Ala Leu
            20                  25                  30

Lys His Asn Ser Leu Gly Asp Ile Leu Asn Asp Thr Ile Asn Leu
        35                  40                  45

Lys Asp Ser Ser Gly Gly Ala Gly Ile Lys Leu Pro Ala Lys Pro Val
    50                  55                  60

Phe Leu Lys Lys His Gly Ile Glu Gly Leu Asn Tyr Asn Leu Asp Asn
65                  70                  75                  80

Lys Ser Arg Pro Phe Ile Tyr Cys Asp Phe Tyr Asp Val Ser Ser Cys
                85                  90                  95

Asp Pro Met Glu Arg Ser Cys Pro Thr Val Lys Met Cys Tyr Ala Ser
            100                 105                 110

Val Asn Asp His Arg Leu Gly Cys Met Ala Ala Leu Val Asn Asn Ser
        115                 120                 125

Leu Thr Arg Gln Val Thr Leu Lys Gly Cys Trp Met His Asp Gly Asn
130                 135                 140

Leu Gly Asn Cys Asp Asn Ser Gln Cys Ile Ala Asp Glu Arg Pro Thr
145                 150                 155                 160

Gly His Gly Asn Ala Ala Leu Phe Cys Cys Ser Thr His Tyr Cys
                165                 170                 175

Asn Arg Arg Val Gln Phe Pro Pro Gln Arg Val Ala Thr Ser Pro Pro
            180                 185                 190

Thr Thr Val Glu Pro Met Glu Ile Glu Asp Pro Ala Phe Phe Gly Ala
        195                 200                 205

Gly Ser Arg Met Phe Ala Ile Ile Ile Leu Gly Phe Phe Ser Ile Cys
    210                 215                 220

Ala Leu Ala Leu Phe Cys Tyr Tyr Ser Tyr Arg Glu Tyr Arg Asn Ser
225                 230                 235                 240

Arg His Tyr Lys Glu Lys
                245

<210> SEQ ID NO 20
<211> LENGTH: 216
<212> TYPE: PRT
<213> ORGANISM: Brugia malayi
<220> FEATURE:
<221> NAME/KEY: MISC_FEATURE
<223> OTHER INFORMATION: >gi|170581122|ref|XP_001895546.1| hypothetical
      protein Bm1_20460 [Brugia malayi]

<400> SEQUENCE: 20

Met Asp Lys Pro Gly Thr Met Glu Leu Trp Gln Val Phe Arg Lys Asp
1               5                   10                  15

Met Cys Gln Gln Ala Ile Glu Lys Cys Gly Phe Leu Leu Glu Asn Asp
            20                  25                  30

Leu Trp Pro Ser Phe Ile Asn Cys Ser Asp Thr Ile Lys Ser Lys Asp
        35                  40                  45

Gly Arg Arg Ile Phe Ser Asp Gly Ser Cys Ala Met Thr Tyr Asn Lys
    50                  55                  60

Glu Pro Ser Lys Met Glu Pro Lys Gln Cys Leu Trp Pro Leu Ala Val
65                  70                  75                  80

```
Gly Ile Ser His Lys Pro Leu Ala Gln Pro Leu Ile Asp Asp Cys Tyr
                85                  90                  95

Leu Pro Cys Arg Pro Pro Leu Ile Ser Ser Gln Trp Leu Tyr Asp Gly
            100                 105                 110

Phe Arg Met Ser Ile Phe Ser Phe Ser Leu Leu Ile Val Val Gly Gly
            115                 120                 125

Leu Val Ser Ala Leu Tyr Leu Phe Ile Phe Ser Leu Leu Phe Thr Ser
130                 135                 140

Asp Leu Cys Val Tyr Ser Leu Thr His Ala Leu Leu Ser Ala Ser Val
145                 150                 155                 160

His Trp Phe Ile Trp Leu Leu Ser Tyr Ala Asp Arg Val Ala Glu Arg
                165                 170                 175

Ala Met Cys Phe Asp Met Leu Arg Arg Asp Ala Lys Ile Leu Arg Lys
            180                 185                 190

Arg Lys Val Val Asn Leu Phe Lys Leu Asp Val Tyr Asp Glu Lys Ile
            195                 200                 205

Ile Leu Ala Leu Arg Ala Arg Leu
210                 215

<210> SEQ ID NO 21
<211> LENGTH: 727
<212> TYPE: PRT
<213> ORGANISM: Brugia malayi
<220> FEATURE:
<221> NAME/KEY: MISC_FEATURE
<223> OTHER INFORMATION: >gi|170591448|ref|XP_001900482.1| hypothetical
      protein Bm1_45100 [Brugia malayi]
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (394)..(394)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid

<400> SEQUENCE: 21

Met Asp Gly Arg Asp Glu Arg Asp Asp Gln Lys Val Arg Arg Glu Met
1               5                   10                  15

Glu Arg Ile Lys Gln Arg Lys Gly Ile Glu Arg Arg Gln Asp Gly Leu
            20                  25                  30

His Lys Ile Tyr Ser Thr Ser Thr Ser Thr Ala Ala Leu Thr Asn Ser
        35                  40                  45

Xaa Ile Ser His Lys Val Ala Leu Ser Pro Val Ser Ser Ser Ser Ile
50                  55                  60

Gln Ser Pro Val Ile Ala Thr Thr Ser Asn Thr Phe Thr Ile Ser Ala
65                  70                  75                  80

Val Ile His Asn Asp Leu Leu Cys Asn Asp Gly Ser Glu Phe Val Cys
                85                  90                  95

Val Cys Gln Gln Asn Ala Gly Asn Leu Leu Lys Ser Tyr Val Leu Cys
            100                 105                 110

Asn Glu Leu Ile Glu Leu Asp Lys Leu Pro Val Ile Glu Met Asn Ile
            115                 120                 125

Arg Arg Val Asn Leu Ser Ala Arg Leu His Thr Asn Glu Thr Tyr Glu
130                 135                 140
```

```
Ser Tyr Phe Lys Arg Arg Val Ala Ala Val Val Ser Asn Tyr Cys Glu
145                 150                 155                 160

Gln Gln Ala Asp Glu Cys Met Ala Thr Thr Leu Arg Leu Arg Lys Glu
            165                 170                 175

Asn Val Val Leu Leu Ser Ile Lys Pro Asn Asn Leu Gln Ser Thr Ala
        180                 185                 190

Ile Gly Phe Val Ile Thr Lys Ser Gln Arg Arg Ser Thr Leu Ser Thr
    195                 200                 205

Met Thr Ile Leu Asp Ser Ile Lys Val Lys Tyr Val Leu Ser Ala Gln
    210                 215                 220

Leu Ala Ala Leu Ser Arg Ile Leu Gly Gly Val Arg Ile Glu Gln Val
225                 230                 235                 240

Glu Ile Val Thr Met Glu Lys Tyr Arg Asn Asn Asn Ser Ser Glu Ser
            245                 250                 255

Ile Gln Arg His Asn Phe Gly Leu Leu Leu Ile Leu Ser Ile Val Ala
        260                 265                 270

Thr Phe Leu Thr Met Thr Tyr Thr Ile Ala Ala Val Arg Val Cys Arg
    275                 280                 285

Asp Cys Tyr Ala Lys Arg Gln Ala Lys Lys Asn Ala Ser Asn Leu Asn
290                 295                 300

Ile Ala Phe Glu Thr Pro Asn Tyr Gly Thr Cys Thr Gln Gln Lys Gln
305                 310                 315                 320

Asn Glu Met Ser Gly Asn Tyr Glu Ile His Ser Thr Met Lys Met Arg
            325                 330                 335

Thr Ser Glu Glu Asn Asp Pro Asn Asn Ser Asn Gln Gly Glu Val Ala
        340                 345                 350

Val Phe Thr Asn Tyr Gln Met Lys Arg Met Phe Gln Cys Asp Pro Ser
    355                 360                 365

Gln Leu Pro Gly Glu Glu Ile Pro Pro Leu Pro His Asp Leu Phe Ile
    370                 375                 380

Ile Phe Ala Ser Lys Ser Leu Val Asp Xaa Lys Ser Gln Thr Cys Asn
385                 390                 395                 400

Pro Gln Ser Lys Leu Ile Ile His Gln Ser Leu Lys Ala Glu Gln Lys
            405                 410                 415

Lys Lys Asn Ser Pro Leu Ser His Lys Ser Asp Glu Glu Asn Asn Ile
        420                 425                 430

Val Glu Val Pro Gln Lys Cys Thr Asn Met Leu Ala Lys Xaa Glu Glu
    435                 440                 445

Thr Ala Lys Ala Ser Pro His Phe Asn Ser Asn Leu Thr Ala Cys Phe
450                 455                 460

Cys Glu Pro Lys Tyr Glu Phe Phe Glu Gln Gln Thr Lys Glu Leu Pro
465                 470                 475                 480

Thr Ser Thr Cys Asn Gln Pro Met Ala Glu Glu Ser Leu Gln Pro Thr
            485                 490                 495

Cys Ser Gln Thr Glu Thr Ile Pro Lys Leu Met Asn Ser Asn Leu Lys
        500                 505                 510

Gly Pro Thr Thr Asp Glu Gln Thr Glu Ala Val Trp Lys Gln Leu Glu
    515                 520                 525

Ile Gly Asn Glu Ser Thr Trp Leu Pro Asn Ala Gln Glu Pro Arg Asp
    530                 535                 540

Lys Pro Tyr Cys Leu Thr Gly Ser Phe Ser Glu Ser Ser Phe Lys Val
545                 550                 555                 560

Ala Asn Tyr Cys Asn Glu Glu Thr Val Asn Leu Glu Leu Tyr Gln Ser
```

```
                        565                 570                 575

Asn Arg Arg Thr Lys Ser Arg Thr Lys Asn Glu Ile Ser Gly Ser Lys
                580                 585                 590

Thr Ile Pro Leu Thr Asp Gln Leu Gly His Leu Gln Glu Ser Lys His
                595                 600                 605

Ser Asp Gly Phe Ala Lys Tyr Glu Asn His Ile Val Gln Lys Ser Arg
                610                 615                 620

Thr Thr His Gln Phe Asp Asp Trp Ser Ser Glu Ser Asp Asp Gly Glu
625                 630                 635                 640

Ile Gly Ala Tyr His Lys Leu Ser Glu Ile Glu Glu Glu Gly Gly Asn
                645                 650                 655

Asp Arg Ser Pro Glu Phe Ala Thr Asp Phe Arg Leu Asn Leu Asp Val
                660                 665                 670

Gln Ser Lys Thr Phe Ile Ser Thr Glu Gln Phe Lys Val Ser Asn Thr
                675                 680                 685

Asp Met Ser Cys Tyr Glu Gln Leu Gln Glu Ser Ala Pro Pro Leu Asn
                690                 695                 700

Ser Ser Thr Ser Asn Arg Val Thr Pro Lys Glu Phe Ala Ser Phe
705                 710                 715                 720

Thr Pro Thr Asp Asp Leu Lys
                725

<210> SEQ ID NO 22
<211> LENGTH: 231
<212> TYPE: PRT
<213> ORGANISM: Brugia malayi
<220> FEATURE:
<221> NAME/KEY: MISC_FEATURE
<223> OTHER INFORMATION: >gi|170574981|ref|XP_001893045.1| hypothetical
      protein [Brugia malayi]

<400> SEQUENCE: 22

Met Ile Gly Leu Trp Lys Asp Asn Gly Tyr Gln Gln Thr Tyr His Ser
1               5                   10                  15

Cys Gln Leu Arg Lys Glu Glu Val Lys Arg Gly Lys Arg Lys Ala Val
                20                  25                  30

Ala Glu Gln Gln Asp Gly Tyr Arg Arg Arg Gln Asp Ser Ala Asp Asp
                35                  40                  45

Asn Ser Gly Ser Met Gly Gly Ala Leu Ile Ser Pro Ala Ile Val Ala
                50                  55                  60

Ala Ala Arg Tyr Ala Val Met Val Ala Ala Ile Arg Gln Gln Met
65                  70                  75                  80

Arg Cys Cys Met Pro Ala Val Val Asp Asn Gln Leu Gln Lys Phe Glu
                85                  90                  95

Asn Asp Pro Glu Ile Arg Gln Leu Val Gly Pro Ser Gln Ile Ala Phe
                100                 105                 110

Ser Gly Leu Pro His Ala Pro Pro Val Glu Arg Arg Asn Ala Leu Leu
                115                 120                 125

Gln Ser Cys Thr Asp Gln Gln Gln Pro Arg Leu Pro Ile Thr Phe Thr
                130                 135                 140

Gln Phe Gly Tyr Asn Ser Asp Phe Pro Leu Ser Ser Cys Thr Ile Gly
145                 150                 155                 160

Gln Glu Glu Ile Thr Phe Glu Ser Arg Phe Ile Leu Asn Gly Val Cys
                165                 170                 175

Val Ile Leu Arg Gly Ile Leu Asn Arg Glu Leu Met Thr Gly Ser Ser
                180                 185                 190
```

```
Thr Leu Gln Phe Asp Glu Gln Lys Ala Ala Glu Glu Leu His Arg
        195                 200                 205

Gln Gln Ala Met Gln Gln Tyr Gly Asp Arg Ile Gln Ala Ile Arg Gln
210                 215                 220

Arg Phe Asn Leu Pro Gln Ser
225                 230

<210> SEQ ID NO 23
<211> LENGTH: 129
<212> TYPE: PRT
<213> ORGANISM: Brugia malayi
<220> FEATURE:
<221> NAME/KEY: MISC_FEATURE
<223> OTHER INFORMATION: >gi|170579749|ref|XP_001894967.1| hypothetical
      protein Bm1_17550 [Brugia malayi]

<400> SEQUENCE: 23

Met Val Ile Thr Ala His Asn Asp Pro Ile Leu Thr Tyr Ser Asn Val
1               5                   10                  15

Pro Thr Thr Ser Ala Ala Ala Asn Asp Asp Thr Ala Arg Ala Ile
            20                  25                  30

Gly Gly Gly Ala Thr Gly Ile Gly Thr Thr Asp Cys Gly Val Ile Asp
        35                  40                  45

Asp Asp Thr Ile Arg Asp Cys Val Ile Thr Asp Cys Thr Ile Gly Lys
    50                  55                  60

Met Val Leu Leu Met Val Leu Ala Val Val Leu Val Ala Ala
65                  70                  75                  80

Glu Ile Arg Thr Ser Ser Ser Gln Glu Ser Ala Ser Asn Leu Lys Arg
                85                  90                  95

Arg Ser Lys Phe Glu Gln Ile Pro Leu Arg Thr Glu Pro Pro Lys Ser
            100                 105                 110

Arg Lys Glu Leu Arg Lys Glu Arg Gln Ala His Glu Lys Thr Asp Thr
        115                 120                 125

Lys

<210> SEQ ID NO 24
<211> LENGTH: 210
<212> TYPE: PRT
<213> ORGANISM: Brugia malayi
<220> FEATURE:
<221> NAME/KEY: MISC_FEATURE
<223> OTHER INFORMATION: >gi|170574965|ref|XP_001893039.1| hypothetical
      protein Bm1_07845 [Brugia malayi]
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 24

Met Leu Arg Gln Val Leu Ile Ile Asn Asn Ser Leu Ala Gly Ile Phe
1               5                   10                  15

Gln Leu Leu Pro Ile Val Glu Ser Leu Arg Phe Arg Gln Leu Arg Leu
            20                  25                  30

Leu Ile Gln Leu Ile Val Ile Leu Leu Leu Phe Tyr Xaa Lys Thr
        35                  40                  45

Ile Phe Ala Ile Gly Thr Cys Thr Glu Pro Glu Met Ala Cys Gly Ala
    50                  55                  60
```

```
Gln Leu His Ser Tyr Pro Leu Leu Arg Leu Asp Glu Thr Ser Gly Xaa
 65                  70                  75                  80

Asn Phe Glu Ser Asn Met Asn Asp Phe Pro Leu Tyr Asp Glu Phe Phe
                 85                  90                  95

Thr Pro Thr His Val Phe Asn Phe Ser Lys Thr Val Asn Ile Thr Gly
            100                 105                 110

Glu Arg Ile Cys Glu Cys Ser Asn Asp Thr Ile Cys Arg Leu Glu Glu
            115                 120                 125

Glu Asn Ile Ile Lys Leu Asp Glu Met Ile Thr Leu Ile Phe Cys Asp
130                 135                 140

Arg Val Asp Asn Ile Phe Arg His Ser Cys His Gly Thr Arg Ser Leu
145                 150                 155                 160

Ile Arg Val Ile Gly Arg Ile His Glu Ser Gly Glu Ala Leu Thr Thr
                165                 170                 175

Ile Val Gln Thr Phe Leu Phe Cys Lys Cys Glu Arg Gly Tyr Arg Arg
            180                 185                 190

Ile Arg Val Glu Ala Trp Leu Asn His Leu Tyr Ala Phe Ile Tyr Arg
            195                 200                 205

Cys Leu
    210

<210> SEQ ID NO 25
<211> LENGTH: 251
<212> TYPE: PRT
<213> ORGANISM: Brugia malayi
<220> FEATURE:
<221> NAME/KEY: MISC_FEATURE
<223> OTHER INFORMATION: >gi|170579615|ref|XP_001894908.1| hypothetical
      protein Bm1_17255 [Brugia malayi]

<400> SEQUENCE: 25

Met Lys Met Lys Arg Asn Asp Asp Leu Gln Ser Leu Met Ser Cys
 1               5                  10                  15

Met Met His Val His Tyr Tyr Phe Cys Phe Phe Phe Leu Trp
                 20                  25                  30

Tyr Thr Phe Gly Asp Thr Ile Asn Thr Phe Ala Phe Thr Leu Asp
             35                  40                  45

Asp Tyr Ser Leu Ile Cys Arg Pro Gly Tyr Arg Val Ser Lys Leu Gln
 50                  55                  60

Arg Ser Pro Lys Tyr Asn Gly Lys Leu Gly Ser Leu Val Val Gln Cys
 65                  70                  75                  80

Glu Leu Ile Glu Arg Asn Thr Gln Leu Val Lys Cys Gly Ser Leu Gln
                 85                  90                  95

Ser Ala Pro Gln Cys Ser Gly Ile Leu Glu Gly Cys Pro Gly Gln Thr
            100                 105                 110

Trp Leu Ala Gly Phe Asn Leu Tyr Leu Ile Glu Asn Pro Ala Lys Val
            115                 120                 125

Met Leu Trp Asp Pro Ile Cys Cys Thr Ser Lys Asn Ile Ile Asp
130                 135                 140

Glu Asn Ala Cys Ile Asn Asp Arg Ile Asn Gln Pro Asn Glu Asn Phe
145                 150                 155                 160

Glu His Glu Ile Ala Asn Asp Leu Ile Tyr Arg Gly Leu Gln Cys Trp
                165                 170                 175

His Gln Tyr Asn Asp Asn Asn Thr Leu Phe Asp Ile Ile Trp Lys Met
            180                 185                 190
```

```
Glu Ile Cys Pro Phe Ser Ser Pro Met Gly Thr Leu His Lys Thr Gln
            195                 200                 205

Asp Cys Pro Glu Cys Gly Cys Asp Cys Gly Lys Ser Gln Cys Pro Asp
    210                 215                 220

Ser Ser Tyr Pro Ser Lys Leu Ile His Lys His Pro Glu Ser His Ser
225                 230                 235                 240

Cys Gln Cys Arg Cys Asp Cys Ile Thr Val Cys
            245                 250

<210> SEQ ID NO 26
<211> LENGTH: 487
<212> TYPE: PRT
<213> ORGANISM: Brugia malayi
<220> FEATURE:
<221> NAME/KEY: MISC_FEATURE
<223> OTHER INFORMATION: >gi|170581054|ref|XP_001895519.1| hypothetical
      protein [Brugia malayi]

<400> SEQUENCE: 26

Met Lys Glu Gln Ile His Glu Val Asp Thr Lys Ile Ala Leu Ser His
1               5                   10                  15

Leu Ala Gln Ile Arg Val Val Gly Tyr Ser Tyr Lys Pro Glu Ile Ala
            20                  25                  30

Leu Lys Trp Gly Leu Ser Glu Glu Asn Arg His Arg Val Gly Val Ile
        35                  40                  45

Ala Gln Glu Leu Ala Glu Ile Leu Pro Asp Ala Val Thr Asp Asn Gly
    50                  55                  60

Asp Tyr Leu Gln Val Asp Asp Ser Arg Ile Phe Tyr Glu Thr Val Ala
65                  70                  75                  80

Ala Ala Thr Glu Leu Cys Arg Leu Thr Gly Asn Leu Glu His Lys Ile
                85                  90                  95

Glu Ala Val Glu Lys Leu Ser His Lys Leu Ala Arg Leu His Arg Arg
            100                 105                 110

Lys Asn Lys Asp Val Gly Ser Leu Ala Ser Gly Leu Ser Asp Leu Gly
        115                 120                 125

Phe Ser Asp Lys Ala Ser Phe Met Ser Ser His Thr Ser Leu Ala Ser
    130                 135                 140

Ile Thr Pro Ser Cys Val Ser Arg Asp Lys Cys His Arg Arg Ser Asn
145                 150                 155                 160

Lys Glu Arg Gly Arg Asn Arg Glu Lys His Trp His Cys Arg Asn Pro
                165                 170                 175

Ser Cys His Arg Val Glu Pro Pro Leu Cys Ser Ser Lys Val Thr Gln
            180                 185                 190

Gly Thr Ile Val Val Leu Val Gly Ile Met Ala Ile Cys Leu Ile Ala
        195                 200                 205

Met Ser Thr Leu Tyr Val Leu Asp Trp His Asn Arg Thr Phe Gly Tyr
    210                 215                 220

Gln Lys Arg Pro Tyr Ile Phe Glu Ser Ser Thr Asn Gly Pro Val
225                 230                 235                 240

Val Leu Glu Gln Gly Gly Lys Ile Gly Gln Ile Val Gln Val Lys Asp
                245                 250                 255

Asn Ile Trp Lys Pro Pro Ile Gln Pro His Ala Pro Pro Leu Ser Val
            260                 265                 270

Ser Cys Asp His Met Tyr Cys His Met Phe Cys Cys Met Glu Arg Asp
        275                 280                 285

Glu Tyr Asn Val Pro Asn Asp Ile Ser Ile Asp Lys Asn Gln Gln Thr
```

```
                290                 295                 300
Val Leu Thr Leu Ser Gln Gln Gln Ser Phe Leu Lys Val Arg Asn
305                 310                 315                 320

Gly Ser Glu Asn Arg Pro Leu Ser Leu Asp Arg Arg Ala Val Phe Ser
                325                 330                 335

Ser Leu Ala Ser Asp Ile Ile Ile Glu Ile Leu Asp Phe Asn Val Thr
                340                 345                 350

Ile Asp Gly Arg Tyr Cys Ile Asn Asp Ser Cys Glu Pro Arg Arg Gly
                355                 360                 365

Leu Tyr Thr Leu Tyr Ile Pro Ile Ser Pro Thr Met Pro Thr Val Pro
                370                 375                 380

Leu Glu Ile Lys Phe Asp Val Gly Asp Ser Gly Thr Tyr Ile Asp Asn
385                 390                 395                 400

Cys Gly Ser Leu Arg Asp Phe Asp Gln Lys Pro Cys Asn Asp Glu His
                405                 410                 415

Ala Ile Arg Thr Asp Arg Gly Lys Gln Pro Val Val Gln Lys Ile Val
                420                 425                 430

Glu Gly Ile Tyr Glu Leu Pro Val Gly Asn Tyr Val His Ser Ala Tyr
                435                 440                 445

Arg Phe Arg Ile Gly Tyr Ser Thr Glu Ser Cys Asn Met Asn Glu Ser
                450                 455                 460

Gln Arg Gly Arg Ser Phe Asp Glu Tyr Asn Leu Ile Phe Tyr Arg Arg
465                 470                 475                 480

Cys Gln Thr Ala Met Asn Phe
                485

<210> SEQ ID NO 27
<211> LENGTH: 289
<212> TYPE: PRT
<213> ORGANISM: Brugia malayi
<220> FEATURE:
<221> NAME/KEY: MISC_FEATURE
<223> OTHER INFORMATION: >gi|170591901|ref|XP_001900708.1| hypothetical
      protein Bm1_46230 [Brugia malayi]
<220> FEATURE:
<221> NAME/KEY: misc_feature
<222> LOCATION: (22)..(22)
<223> OTHER INFORMATION: Xaa can be any naturally occurring amino acid

<400> SEQUENCE: 27

Met Lys Phe Gly Ser Val Thr Asn Ala Val Ser Glu Lys Val Thr Thr
1               5                   10                  15

Ala Gly Thr Glu Asp Xaa Tyr Met Lys Asn Arg Leu Glu Lys Glu Asp
                20                  25                  30

Asp Ser Glu Lys Ser Ile Thr Ser Asn Glu Asp Phe Glu Val Ile Gly
                35                  40                  45

Ser Gln Ala Arg Ile Ser Lys His Ser Ala Ser Asp Asp Gly Glu Leu
            50                  55                  60

Asn Asp Ser Phe Ile Asp Leu Phe Lys Lys His Ile Val Lys Arg Arg
65                  70                  75                  80

Val Pro Ser Ser Ile Gly Arg Asn Glu Ala Gln Asn Lys Asp Asp Cys
                85                  90                  95

Ser Arg Met Ser Trp Lys Val Leu Phe Ile Ile Leu Gly Ile Ile
                100                 105                 110

Ser Phe Gln Leu Gln Leu Ile Leu Lys Arg Pro Lys Val Phe Asp Glu
                115                 120                 125

Thr Leu Lys Asp Thr Ile Thr Lys Gln Gln Gln Ile Ile Asp Arg Leu
```

-continued

```
            130                 135                 140
Glu Asn Gln Leu Lys Ser Cys Ala Pro Leu Asp Val Tyr Ser Leu Pro
145                 150                 155                 160

Val Arg Ile Glu Glu Arg Val Thr Ala Phe Asp Arg Lys Asp Gly
                165                 170                 175

Phe Asn Tyr Phe Phe Val Ile Val Asp Trp Lys Lys Asn Asp Arg Gly
                180                 185                 190

Met Ala Arg Gln His Leu His Leu Ala Phe Lys Gln Ser Asn Ser Ser
            195                 200                 205

Ile Tyr Ile Tyr Asp His Gly Pro Leu Ser Gly Arg Tyr Phe Thr Val
            210                 215                 220

Gly Asp Arg Ile Ile Asp Ile Asp Gly Val Thr Phe Val Arg Ala Ala
225                 230                 235                 240

Asp Leu Arg Asp Arg Ile Leu Trp Ser His Tyr Asn Arg Asp Tyr Phe
                245                 250                 255

Thr Ser Ile Ile Glu Arg Pro Ala Thr Glu Gln Ala Val His Thr Val
                260                 265                 270

Ser Thr Leu Leu Gln Pro Ser Leu Ser Ser Phe Ser Val Val Leu Ser
            275                 280                 285

Ala
```

IMMUNOGENIC COMPOSITIONS AND VACCINES FOR PREVENTING OR TREATING FILARIAL DISEASE

CROSS-REFERENCE TO RELATED APPLICATIONS

This application is a U.S. National Stage application of PCT/US2016/022787 filed Mar. 17, 2016, which claims the benefit of, and relies on the filing date of, U.S. provisional patent application No. 62/135,115, filed Mar. 18, 2015, the entire disclosure of which is incorporated herein by reference.

STATEMENT OF GOVERNMENT INTEREST

This invention was made with government support under grant number R073UE awarded by the Uniformed Services University. The government has certain rights in the invention.

SEQUENCE LISTING

The instant application contains a Sequence Listing which has been submitted electronically in ASCII format and is hereby incorporated by reference in its entirety. Said ASCII copy, created on Mar. 9, 2016, is named HMJ-150-PCT_ST25.txt and is 120,000 bytes in size.

BACKGROUND

The filariae are thread-like parasitic nematodes (roundworms) that are transmitted by arthropod vectors. The adult worms inhabit specific tissues where they mate and produce microfilariae, the characteristic tiny, thread-like larvae.

The microfilariae infect vector arthropods, in which they mature to infective larvae. Diseases caused by filariae are a major health problem in many tropical and subtropical areas. *Wuchereria bancrofti* and *Brugia malayi* are filarial parasites that are the major causative agents of lymphatic filariasis. Currently, it is estimated that over 129 million people are infected with either of these organisms and over one billion live in at-risk areas. Since 2000, there has been an ongoing effort through the Global Program to Eliminate Lymphatic Filariasis to eradicate these infections. While this program is having a substantive impact on the prevalence of infection, its efficacy is limited by the need to repeatedly treat entire endemic populations for 6-10 years. The advent of new tools, such as vaccines or more effective anthelmintics, would be of great benefit toward these eradication efforts.

One of the principle obstacles in designing vaccines against such parasitic worms, however, is that previously exposed individuals frequently have IgE antibodies to surface and secreted worm antigens, putting them at risk for allergic reactions when re-exposed to these antigens. Since intestinal antigens of helminths may be "hidden" from the immune response during natural infection, yet accessible by antibodies after antigen administration, homogenates of such antigens have been proposed for use in vaccines. However, while the genomes of *Wuchereria bancrofti* and *Brugia malayi*, as well as the filarial genomes of the causative agents of loiasis and river blindness have been completed, the anatomic localization of proteins in these filarial worms is unknown. Moreover, the use of homogenates from helminth intestines has resulted in variable efficacy.

Other diseases known in the art, which are caused by filarial parasites, include heartworm disease. This disease is caused by the parasite *Dirofilaria immitis*. The physical presence of the heartworm parasite in the pulmonary artery and right ventricle of the canine heart, for example, and the resulting destruction of tissue, causes respiratory and circulatory problems which can be fatal under conditions of stress or vigorous exercise. The heartworm parasite has also been shown to be the cause of focal lung, liver, eye and cutaneous lesions in man. Currently, heartworm disease is treated by administering anti-parasitic agents to infected animals. Unfortunately, heartworm disease that has not been diagnosed in its early stages may be quite refractile to treatment.

Accordingly, there is a need in the art for immunogenic compositions, such as vaccines, which may be used to prevent or treat diseases caused by filarial worms including lymphatic filariasis, loiasis, river blindness and heartworm.

BRIEF SUMMARY

Further areas of applicability of the present disclosure will become apparent from the detailed description provided hereinafter. It should be understood that the detailed description and specific examples, while indicating embodiments of the disclosure, are intended for purposes of illustration only and are not intended to limit the scope of the disclosure.

The present disclosure is directed to an immunogenic composition including: at least one or at least two isolated polypeptides or immunogenic fragments thereof, and optionally a pharmaceutically acceptable carrier, wherein each polypeptide is expressed on a luminal surface of an intestine of a filarial worm, wherein each polypeptide is expressed at a level at least two-fold higher in the intestine in comparison to the level of expression of each polypeptide in a reproductive tract or a body wall of the filarial worm, wherein each isolated polypeptide has at least one transmembrane domain, and wherein each polypeptide is a non-mitochondrial polypeptide.

Also provided herein is a method for preventing or treating a filarial disease including administering an effective amount of a vaccine composition including at least one or at least two isolated polypeptides or immunogenic fragments thereof to a subject in need thereof, wherein each polypeptide is expressed on a luminal surface of an intestine of a filarial worm, wherein each polypeptide is expressed at a level at least two-fold higher in the intestine in comparison to the level of expression of each polypeptide in a reproductive tract or a body wall of the filarial worm, wherein each isolated polypeptide has at least one transmembrane domain, and wherein each polypeptide is a non-mitochondrial polypeptide.

BRIEF DESCRIPTION OF THE DRAWINGS

The present disclosure will become more fully understood from the detailed description and the accompanying drawings, wherein:

FIGS. 2A and 2B depict the dissection process of adult female *B. malayi*. FIG. 2A shows a break in the body wall and extrusion of the gut and reproductive tract as described in the Examples. Magnification: top left: 40×, bottom left: 100×. FIG. 2B shows the body wall in the process of being slid away from the gut and reproductive tract. Magnification: top right: 30×, bottom right: 20×.

DETAILED DESCRIPTION

Figure 1:
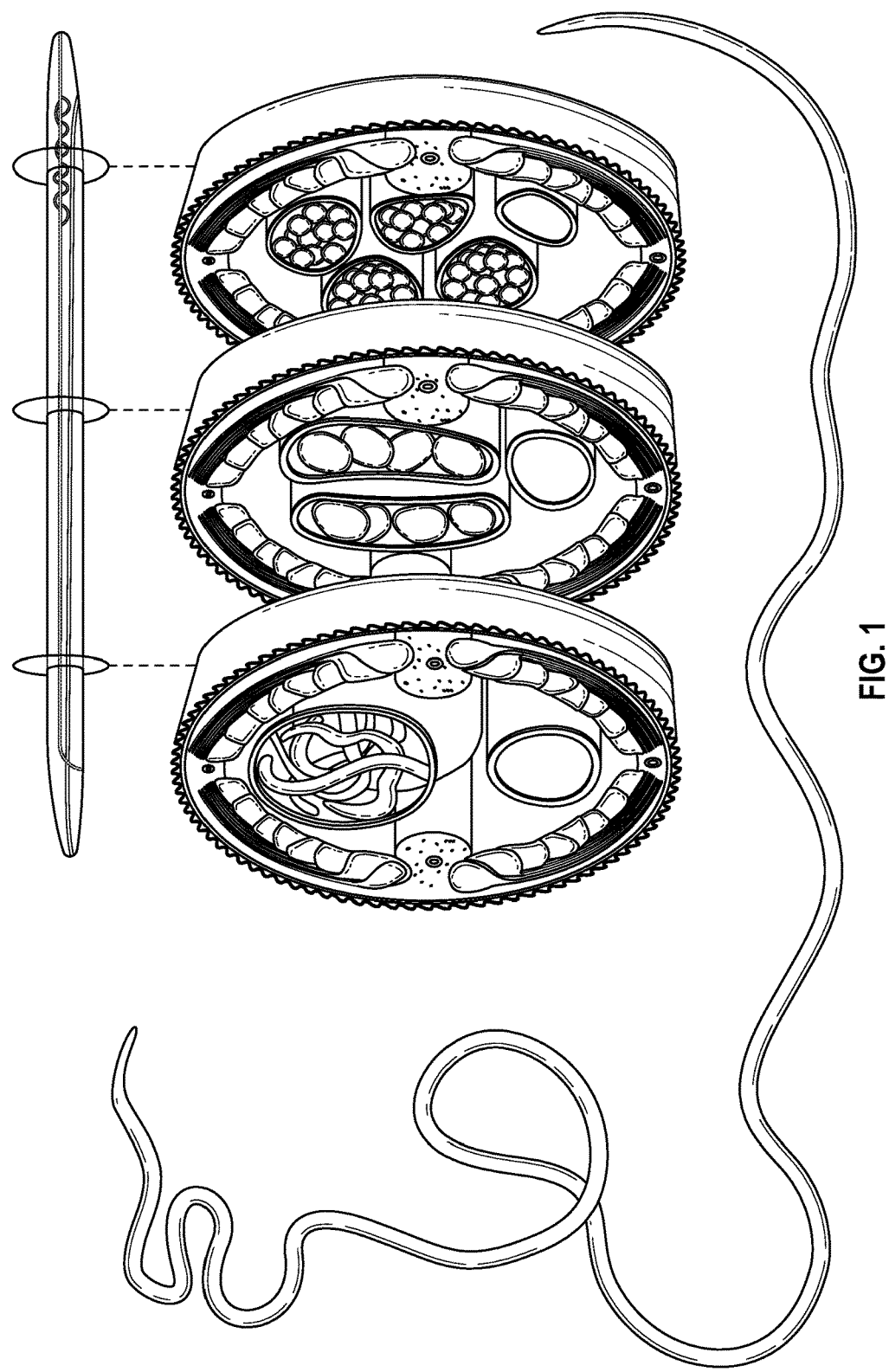
FIG. 1 depicts the anatomy of adult female *B. malayi*. The tissues and structures dissected for the proteomic analysis as described in the Examples include the body wall, reproductive tract and intestine.

The following description of the embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Immunogenic Composition

In some embodiments, the present disclosure encompasses an immunogenic composition comprising at least one isolated polypeptide as described herein or an immunogenic fragment thereof and optionally a pharmaceutically acceptable carrier.

The term "polypeptide" as used herein refers to a polymer of amino acid residues. This term is used interchangeably with the term "protein."

In some embodiments, the present polypeptides are obtained or derived from a filarial worm. A "filarial worm" as used herein refers to parasitic nematodes of the Metazoa kingdom including the superfamily filarioidea, family Filariidae. Filarial worms include, but are not limited to, species belonging to the genera *Brugia*, such *Brugia malyai, Wuchereria*, such as *Wuchereria bancrofti, Onchocerca*, such as *Onchocerca volvulus, Loa*, such as *Loa loa* and *Dirofilaria*, such as *Dirofilaria immitis*. The phrase "derived from" encompasses actually or theoretically "originating from," "obtained from," or "isolated from" a parent polypeptide.

In some embodiments, the polypeptides of the present immunogenic are expressed on a luminal surface of a filarial worm intestine. Without being bound by theory, it is believed that administering such intestinal luminal surface polypeptides to a subject may mitigate the possibility of an allergic reaction in the subject. Because intestinal antigens may be "hidden" from the immune response during natural infection, yet accessible by antibodies induced by administration, intestinal antigens are likely to have a low potential for eliciting allergic responses when administering, such as vaccinating, previously infected individuals. Further, it is believed that administering, such as vaccinating, a subject with particular intestinal antigens, such as the polypeptides or immunogenic fragments thereof described herein, may be more effective than vaccinating with crude homogenates of antigens since, for example, sufficient amounts of effective antigen may not be present in such mixtures. Accordingly, in some embodiments, the present immunogenic composition consists essentially of the isolated polypeptides disclosed herein, such as one or more isolated polypeptides selected from SEQ ID NOS: 1-27 or immunogenic fragments thereof and a pharmaceutically acceptable carrier and does not encompass crude homogenates of antigen, such as a crude homogenate of intestinal proteins.

In various embodiments, the present polypeptides are enriched in the intestine of a filarial worm in comparison to another anatomic fraction of a filarial worm. As used herein, "enriched" or "abundant" refers to a polypeptide that is naturally found to be expressed at a higher level in the intestine, for example, in comparison to other anatomic fractions, such as the reproductive tract or the body wall. See FIG. 1, which depicts the anatomy of a filarial worm. In some embodiments, the expression level of the polypeptide is at least two fold higher, such as at least three fold higher, such as at least five fold higher, such as at least 10 fold higher, such as at least 50 fold higher in the intestine in comparison to the expression level of the polypeptide in the reproductive tract or the body wall of the filarial worm.

Enrichment or abundance of polypeptides can be assessed by any method known in the art. For example, protein separation and comparison by two-dimensional polyacrylamide gel electrophoresis (2D-PAGE), followed by mass spectrometry (MS) or tandem mass spectrometry (MS/MS) identification may be used for quantitative analysis of protein mixtures, see, for example, H. J. Issaq and T. D. Veenstra, BioTechniques, vol. 44, no. 5, pp. 697-700, 2008, which is herein incorporated by reference. In this method, the intensity of the protein stain is used to make a determination regarding the quantity of a particular protein.

Protein quantitation may also be assessed using non-gel-based "shotgun" proteomic techniques such as Multidimensional Protein Identification (MudPIT). See e.g., A. Motoyama and J. R. Yates III, Analytical Chemistry, vol. 80, no. 19, pp. 7187-7193, 2008 and B. Domon and R. Aebersold, Science, vol. 312, no. 5771, pp. 212-217, 2006, which are each herein incorporated by reference.

Non-gel based proteomic methods may include (i) sample preparation including protein extraction, reduction, alkylation, and digestion; (ii) sample separation by liquid chromatography (LC or LC/LC) and analysis by MS/MS; (iii) data analysis including peptide/protein identification, quantification, and statistical analysis. For example, each sample may be separately prepared, then subjected to individual LC-MS/MS or LC/LC-MS/MS runs. Protein abundance may be assessed, for example, using spectral counting of identified proteins after MS/MS analysis. Spectral count may be measured for individual LC-MS/MS or LC/LC-MS/MS runs and changes in protein abundance may be calculated via a direct comparison between different analyses.

Typically, normalization and statistical analysis of spectral counting datasets are used to detect changes in protein abundance in complex mixtures. See, for example, McIlwain et al., 2012, BMC Bioinformatics, 13, 308, Paoletti et al., 2006, Proc. Natl. Acad. Sci. U.S.A., 103, 18928-18933, regarding determining the relative abundance of a single protein between samples and Liu et al., 2004, Anal. Chem., 76, 4193-4201, for example, regarding estimating relative abundance between different proteins in one sample. These references are herein incorporated in their entireties.

The relative abundance of the present polypeptides may be assessed using normalization and statistical analysis of spectral counting datasets as described in the present Examples. For example, Normalized Spectral Abundance Factor (NSAF) and NSAF enrichment values may be determined (see Examples). In some embodiments, the polypeptides of the present disclosure exhibit an NSAF enrichment value of at least 2, such as at least 3, such as at least 4, such as at least 20 in the intestine and less than 2, such as less than 1 or less than 0.5 in other atomic fractions, such as the body wall or the reproductive tract.

In some embodiments, the polypeptides of the present immunogenic composition have at least one transmembrane domain, such as 1-2 transmembrane domains, to facilitate recombinant expression and a non-cytoplasmic portion to increase the likelihood of interaction with antibodies ingested by filariae. The non-cytoplasmic portion may be for example, 50 amino acids in length or more, such as 100 amino acids in length or more, such as 500 amino acids in length or more. Such features may be determined using methods known in the art or predicted using art known software, e.g. Interpro, Zdobnov E M, Apweiler R. 2001. InterProScan-an integration platform for the signature-recognition methods in InterPro. Bioinformatics 17: 847-848, which is herein incorporated by reference.

In some embodiments, the polypeptide of the present disclosure is specific to the intestine. "Specific" in reference to a particular anatomical fraction of the worm means that the polypeptide was only identified within the specific fraction, e.g., the intestine.

In some embodiments, the present polypeptides are non-mitochondrial peptides, i.e. not present, targeted to or expressed in the mitochondria.

As noted above, the present composition comprising at least one isolated polypeptide is an immunogenic composition. As used herein, the term "immunogen" or "immunogenic" refers to any substrate that elicits an immune response in a host, e.g., at least an antibody response. An "immunogenic composition" includes at least one isolated polypeptide with or without a pharmaceutically acceptable carrier, such as an adjuvant. The immunogenic compositions disclosed herein may or may not be immunoprotective or therapeutic. Accordingly, the term "immunogenic" is not intended to be limited to vaccines.

In some embodiments, the immunogenic composition of the present disclosure is a vaccine. As used herein, a vaccine encompasses an immunogenic composition that prevents, ameliorates, palliates, or eliminates disease from a host, such as the diseases described herein.

In other embodiments, the immunogenic composition described herein may be used to obtain an antibody composition, which may then be administered to a subject to provide temporary immunity, i.e., artificially acquired passive immunity. Methods for preparing and administering such antibody compositions are known in the art and are described, for example, in U.S. Pat. No. 4,748,018, which is herein incorporated by reference in its entirety.

As described herein, a polypeptide of the present immunogenic composition is an isolated polypeptide. The terms "isolated" or "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is considered to be substantially purified. The term "purified" denotes that a protein gives rise to essentially one band in an electrophoretic gel. For example, it means that the protein is at least 85% pure, such as at least 95% pure or at least 99% pure.

In some embodiments, the polypeptide of the present immunogenic composition is a polypeptide selected from SEQ ID NOS: 1-27. In some embodiments, the isolated polypeptide is a cell adhesion protein, such as a polypeptide of SEQ ID NOS: 1 or 2. In some embodiments, the isolated polypeptide is a cell signaling protein, such as a polypeptide of SEQ ID NOS: 3 or 4. In some embodiments, the polypeptide is a chaperone/HSP protein, such as a polypeptide of SEQ ID NOS: 5 or 6. In some embodiments, the polypeptide is involved in xenobiotic metabolism using glucuronidation, for example, a UDP-glucuronosyl or a UDP glucosyl transferase, such as a polypeptide of SEQ ID NOS: 7 or 8, respectively. In some embodiments, the isolated polypeptide is a protease such as SEQ ID NOS: 13, 14 or 15. In some embodiments, the isolated polypeptide is a protease inhibitor, such as SEQ ID NO: 17. A description of SEQ ID NOS: 1-27 is found in Table 7 and Tables C and D.

In some embodiments, the polypeptide of the present immunogenic composition is an immunogenic fragment, such as an immunogenic fragment of SEQ ID NOS: 1-27. The phrase "immunogenic fragment" or "immunogenic portion" refers to a fragment or truncated form of an amino acid sequence, for example, an amino acid sequence selected from the group consisting of SEQ ID NOS. 1-27 that elicits an immunological response.

In some embodiments, the polypeptide of the present immunogenic composition is an immunogenic variant, such as an immunogenic variant of SEQ ID NOS: 1-27. The phrase "immunogenic variant" refers to a substituted form of an amino acid sequence, for example, an amino acid sequence selected from the group consisting of SEQ ID NOS. 1-27 that elicits an immunological response. Insertions and/or deletions may also be incorporated into an immunogenic variant.

In some embodiments, the immunogenic variant of the present disclosure comprises a substitution, such as a conservative substitution for example, a substituted form of an amino acid sequence selected from the group consisting of SEQ ID NOS: 1-27 containing one or more conservative amino acid substitutions. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In general, the immunogenic fragments and variants described herein, such as fragments or variants of the polypeptides of SEQ ID NOS: 1-27 comprise at least one epitope and include at least six contiguous amino acids from the full-length protein, e.g., at least six contiguous amino acids from the cell adhesion protein set forth in SEQ ID NO: 1. More typically, the present variants or fragments will have at least 10, even more typically at least 15, and still more typically at least 19, and yet even more typically 30 contiguous amino acids from the full-length protein, e.g., the cell adhesion protein set forth in SEQ ID NO: 1.

The term "epitope" means a segment or fragment of a composition of matter, e.g., a polypeptide, which is recognized by the immune system, specifically by antibodies, B cells, or T cells. In some embodiments, the epitope is generally a fragment or fragments of a polypeptide set forth in SEQ ID NOS: 1-27.

Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J), which is herein incorporated by reference. For example, linear epitopes may be determined by concurrently synthesizing large numbers of peptides on solid supports, the peptides corresponding to portions of a protein molecule, and reacting the peptides with antibodies while the peptides are still attached to the supports. Such techniques are known and described in the art, see e.g., U.S. Pat. No. 4,708,871; Geysen et al., 1984, Proc. Natl. Acad. Sci. U.S.A. 81, 3998-4002; and Geysen et al., 1986, Molec. Immunol. 23,709-715, which are herein incorporated by reference in their entireties. Similarly, conformational epitopes are readily identified by determining spatial conformation of amino acids, such as by, e.g., x-ray crystallography and two-dimensional nuclear magnetic resonance. See Epitope Mapping Protocols, supra.

In some embodiments, the polypeptides of the present disclosure encompass polypeptides that are substantially homologous to the polypeptides set forth in SEQ ID NOS: 1-27. The substantially homologous polypeptides may be from or derived from any filarial species or genera including but not limited to Brugia, such as Brugia malyai, Wuchereria, such as Wuchereria bancrofti, Onchocerca, such as Onchocerca volvulus, Loa, such as Loa loa and Dirofilaria, such as Dirofilaria immitis. In some embodiments, the polypeptides of the present disclosure, which are substantially homologous to the polypeptides set forth in SEQ ID NOS: 1-27 are not substantially homologous to a human polypeptide.

In some embodiments, the immunogenic composition includes at least one isolated polypeptide comprising an amino acid sequence selected from SEQ ID NOS: 1-7, SEQ ID NO: 11, SEQ ID NO: 14, SEQ ID NOS: 18-20, SEQ ID NO: 22, SEQ ID NO: 23 and SEQ ID NO: 26.

In specific embodiments, the immunogenic composition includes at least one, for example, polypeptide obtained Dirofilaria immitis and displaying substantial homology to a polypeptide selected from SEQ ID NOS: 1-7, SEQ ID NO: 11, SEQ ID NO: 14, SEQ ID NOS: 18-20, SEQ ID NO: 22, SEQ ID NO: 23 and SEQ ID NO: 26.

As used herein, "homology" refers to the percent sequence identity between two polypeptide moieties. Two polypeptide sequences "display substantial homology" or are "substantially homologous" to each other when the sequences exhibit at least about 41%, such as at least about 75%, more typically at least about 80%-85%, even more typically at least about 90%, and most typically at least about 95%, 96%, 97%, 98%, 99% or more sequence identity over a defined length of the molecules. As used herein, "substantially homologous" also refers to sequences showing complete (100%) sequence identity to the polypeptide sequences.

In some embodiments, a sequence is not substantially homologous when it exhibits a sequence identity of 40% or less sequence identity.

"Sequence identity" as used herein refers to a relationship between two or more polypeptide sequences, namely a reference polypeptide sequence and a given polypeptide sequence to be compared with the reference polypeptide sequence. Sequence identity is determined by comparing the given polypeptide sequence to the reference polypeptide sequence after the polypeptide sequences have been optimally aligned to produce the highest degree of sequence similarity, as determined by the match between strings of such sequences, with gaps introduced if necessary. Upon such alignment, sequence identity is ascertained on a position-by-position basis, e.g., the sequences are "identical" at a particular position if at that position, the amino acid residues are identical. The total number of such position identities is then divided by the total number of residues in the reference sequence to give % sequence identity.

Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988); the teachings of which are incorporated herein by reference.

Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and BLASTX (Altschul, S. F. et al., J. Molec. Biol., 215:403-410 (1990). The BLAST programs are publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences.

In specific embodiments, the immunogenic composition of the instant disclosure includes at least one isolated polypeptide, such as at least two, such as at least three, such as at least four, such as at least five, such as at least six, such as at least seven, such as at least ten, such as at least fifteen, such as at least twenty, such as at least twenty-five, such as at least twenty-six isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to a polypeptide selected from SEQ ID NOS: 1-27.

In other specific embodiments, the immunogenic composition of the instant disclosure includes no more than one isolated polypeptide, such as no more than two, such as no more than three, such as no more than four, such as no more than five, such as no more than six, such as no more than seven, such as no more than ten, such as no more than fifteen, such as no more than twenty, such as no more than twenty-five, such as no more than twenty-six isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-27.

In further specific embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 1 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 2-27 or immunogenic fragments thereof.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 2 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1, 3 and 4-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 3 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1, 2 and 4-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 4 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-3 and 5-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 5 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-4 and 6-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 6 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-5 and 7-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 7 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-6 and 8-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 8 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-7 and 9-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 9 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-8 and 10-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 10 and optionally least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-9 and 11-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 11 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-10 and 12-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 12 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-11 and 13-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 13 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-12 and 14-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 14 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-13 and 15-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 15 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-14 and 16-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 16 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-15 and 17-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 17 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-16 and 18-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 18 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-17 and 19-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 19 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-18 and 20-27.

In some embodiments, the vaccine composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 20 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-19 and 21-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 21 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-20 and 22-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 22 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-21 and 23-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 23 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-22 and 24-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 24 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-23 and 25-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 25 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-24 and 26-27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 26 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-25 and SEQ ID NO: 27.

In some embodiments, the immunogenic composition of the instant disclosure includes at least one isolated polypeptide comprising an amino acid sequence having a sequence identity of at least 75%, such as at least 80%, such as at least 85%, such as at least 90%, such as at least 95%, such as at least 97%, such as at least 98%, such as at least 99%, such as at least 100% to SEQ ID NO: 27 and optionally at least one additional isolated polypeptide, such as at least two, such as at least three, such as at least four, such as at least five, such as at least six, such as at least seven, such as at least ten, such as at least fifteen, such as at least twenty, such as at least twenty-five, such as at least twenty-six additional isolated polypeptides comprising an amino acid sequence having a sequence identity of at least 75%, such as at least 80%, such as at least 85%, such as at least 90%, such as at least 95%, such as at least 97%, such as at least 98%, such as at least 99%, such as at least 100% to an amino acid sequence selected from SEQ ID NOS: 1-26.

In some embodiments, the polypeptides of the present disclosure are recombinant polypeptides. The term "recombinant polypeptide" refers to a protein produced by recombinant expression methods, such as, for example, in prokaryotic or eukaryotic host cells, or in cell-free in vitro expression systems.

The polypeptides of the present disclosure are typically expressed using an expression vector and purified. Expression vectors may be either self-replicating extrachromosomal vectors or vectors that integrate into a host genome. Generally, expression vectors include transcriptional and translational regulatory nucleic acid sequences, operably linked to the nucleic acid encoding the target protein.

In some embodiments, control sequences may be used for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers. A nucleic acid sequence is "operably linked" when it is placed into a functional relationship with another nucleic acid sequence. For example, DNA for a pre-sequence or secretory leader is operably linked to DNA if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences may be contiguous or non-contiguous. Methods for linking DNA sequences are well-known in the art and include use of the polymerase chain reaction and ligation. The transcriptional and translational regulatory nucleic acid will generally be appropriate to the host cell used to express the target protein; for example, transcriptional and translational regulatory nucleic acid sequences from *E. coli* are typically used to express the target protein in *E. coli*.

Numerous types of appropriate expression vectors, and suitable regulatory sequences are known in the art for a variety of host cells. Methods for expressing polypeptides are well known in the art (e.g., Sambrook et al. (1989) Molecular Cloning, A Laboratory Manual, 2nd ed., vol. 1-3, Cold Spring Harbor Laboratory; Berger and Kimmel (1987) Guide to Molecular Cloning Techniques, Methods in Enzymology, vol. 152, Academic Press, Inc., San Diego, Calif.; Ausubel et al. (1995) Current Protocols in Molecular Biology, John Wiley & Sons, Inc., NY) herein incorporated by reference in their entireties.

The polypeptides of the present disclosure may be produced by culturing a host cell transformed with an expression vector containing nucleic acid encoding polypeptides of the present disclosure, such as encoding one or more of SEQ ID NOS: 1-27 or immunogenic fragments or variants thereof, under the appropriate conditions to induce or cause expression of the polypeptides of the present disclosure. The conditions appropriate for protein expression will vary with the choice of the expression vector and the host cell, and may be easily determined by one skilled in the art using routine experimentation.

Appropriate host cells include yeast, bacteria, archaebacteria, fungi, insect cells, and animal cells, including mammalian cells (such as human cells and cells lines). Thus, host cells include, but are not limited to, *Drosophila melanogaster* cells, *Tetrahymena*, *Saccharomyces cerevisiae* and other yeasts, *E. coli*, *Bacillus subtilis*, Sf9 cells, C129 cells, 293 cells, *Neurospora*, BHK, CHO, COS, HeLa cells, Hep G2 cells, THP1 cell line (a macrophage cell line), and human embryonic kidney cell lines (e.g., HEK293).

Nucleic acid molecules encoding the polypeptides of the present disclosure may be cloned using standard molecular biological methods, including DNA amplification methods, such as the polymerase chain method (PCR) (see e.g., Sambrook et al. (1989) Molecular Cloning: A Laboratory Manual, 2nd ed., Cold Spring Harbour, N.Y.; Berger & Kimmel (1987) Methods in Enzymology. Vol. 152: Guide to Molecular Cloning Techniques, Academic Press, Inc., San Diego, Calif.; Co et al. (1992) J. Immunol. 148:1149), which are each herein incorporated by reference. Thus, for example, a nucleic acid molecule encoding a polypeptide of the present disclosure may be PCR-amplified using a sense primer containing one restriction site and an antisense primer containing another restriction site. This will produce a nucleic acid encoding the desired sequence or subsequence having terminal restriction sites. This nucleic acid can then readily be ligated into a vector having appropriate corresponding restriction sites. Suitable PCR primers may be chosen by one of skill in the art based on the sequence to be expressed. Appropriate restriction sites can also be added by site-directed mutagenesis as is well known in the art.

The methods of introducing exogenous nucleic acids into host cells are also well known in the art, and will vary with the host cell used. Suitable techniques include, but are not limited to, dextran-mediated transfection, calcium phosphate precipitation, polybrene mediated transfection, protoplast fusion, electroporation, viral infection, encapsulation of the nucleic acids in liposomes, and direct microinjection of nucleic acids into nuclei.

The polypeptides of the present disclosure may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography.

Some embodiments of the disclosure provide synthetic polypeptides of the present disclosure. Polypeptides having up to about 100-150 amino acid residues may be prepared by in vitro synthesis using established techniques. Synthetic polypeptides may be prepared by chemical synthesis (such as solid phase peptide synthesis) using methods known in the art.

In some embodiments, the immunogenic composition of the present disclosure includes a pharmaceutically acceptable carrier. The carrier must be "acceptable" in the sense that it is compatible with the active ingredient of the composition, and typically, capable of stabilizing the active ingredient and not deleterious to the subject to be treated. In some embodiments, the pharmaceutically acceptable carrier is a non-naturally occurring pharmaceutically acceptable carrier.

The pharmaceutically acceptable carriers (vehicles) may be conventional, but are not limited to conventional carriers (vehicle). For example, E. W. Martin, Remington's Pharmaceutical Sciences, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21st Edition (2006) describe compositions and formulations suitable for pharmaceutical delivery of one or more molecules and additional pharmaceutical agents.

The present immunogenic compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., argenine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof.

In some embodiments, the present immunogenic compositions may comprise propellants (e.g., hydrofluoroalkane (HFA)) for aerosol delivery. In some embodiments, the immunogenic compositions of the present disclosure may be formulated as described in U.S. Pat. No. 5,192,743 that form a gel when reconstituted and which can improve stability of a protein of interest (e.g., for storage).

Immunogenic compositions of the present disclosure may be appropriately constructed for some or all routes of administration, for example topical administration (including inhalation and nasal administration), oral or enteral administration, intravenous or parenteral administration, transdermal administration, epidural administration or the like. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, immunogenic compositions to be administered can contain minor amounts of non-toxic auxiliary substances, such as wetting or emulsifying agents, preservatives, and pH buffering agents and the like, for example sodium acetate or sorbitan monolaurate.

In some embodiments, a parenteral formulation may comprise injectable fluids that include pharmaceutically and physiologically acceptable fluids such as water, physiological saline, balanced salt solutions, aqueous dextrose, glycerol or the like as a vehicle.

For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The aforementioned immunogenic compositions and protein modifications to increase protein stability can be applied as described in U.S. Patent Application 2009/032692, which is herein incorporated by reference in its entirety.

In some embodiments the pharmaceutically acceptable carrier of the present disclosure includes an adjuvant, such as a non-naturally occurring adjuvant. As used herein, an "adjuvant" is understood as a pharmacological or immunological agent that modifies the effect of other agents (e.g., immunogen or target antigen in an immunogenic composition) while having few if any direct effects when given by itself. In some embodiments, an adjuvant will enhance the recipient's immune response to the polypeptides in the present immunogenic composition while keeping the injected foreign material at a minimum.

Suitable adjuvants are well known in the art (see, for example, *Vaccine Design-The Subunit and Adjuvant Approach* (1995) Pharmaceutical Biotechnology, Volume 6 (eds. Powell, M. F., & Newman, M. J.) Plenum Press, New York and London, ISBN 0-306-44867-X), which is incorporated herein by reference in its entirety. Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing *Corynebacterium parvum* and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucleotide, and aluminum hydroxide.

Other exemplary adjuvants include the adjuvants described in Lanar et al., U.S. Pat. No. 7,029,685 and U.S. Patent Publication No. 2006/0073171, herein incorporated by reference in their entireties. Alternatively, the polypeptides of the immunogenic composition described herein can be used without any adjuvant.

Methods

The present disclosure is further directed to methods for preventing or treating filarial diseases. As used herein, "filarial diseases" refer to diseases caused by thread-like nematodes (filariae) that belong to the roundworm superfamily filarioidea family Filariidae. Such diseases include, but are not limited to lymphatic filariasis, river blindness, loiasis or heartworm. As used herein "preventing" refers to the administration of a therapeutically effective amount of a polypeptide, immunogenic composition, such as a vaccine, of the present disclosure to an animal in order to protect the animal from the development of, for example, lymphatic filariasis, river blindness, loiasis, heartworm or the symptoms thereof. In some embodiments, the immunogenic composition of the disclosure is administered to a subject that is at risk for developing a lymphatic filariasis, river blindness, loiasis or heartworm.

By "treating" a disease associated with filarial infection such as lymphatic filariasis, river blindness, loiasis or heartworm is intended administration of a therapeutically effective amount of a polypeptide, immunogenic composition, such as a vaccine of the present disclosure to an animal that has, for example, lymphatic filariasis, river blindness, loiasis or heartworm or that has been exposed to a filarial infection, such as a filarial worm selected from *Brugia malyai, Wuchereria bancrofti, Onchocerca volvulus, Loa loa,* or *Dirofilaria immitis,* where the purpose is to cure, heal, alleviate, relieve, alter, remedy, ameliorate, improve, or affect the condition or the symptoms of the lymphatic filariasis, river blindness, loiasis or heartworm.

The immunogenic compositions of the present disclosure may be administered to a subject. In some embodiments, the subject is a mammal, e.g., a non-human primate such as a baboon or macaque. In some embodiments, the subject mammal is a human. The subject mammal can also include, but is not limited to, pet or companion animals (e.g. cats, dogs, house rabbits, ferrets, rodents, including gerbils, hamsters, chinchillas, rats, mice, guinea pigs, etc); working animals, such as guide animals (e.g., monkeys; herding animals, etc.), draught animals (e.g., draught horses, oxen, camels, elephants, oxen, camels, donkeys) and sport animals (e.g., racing or show-jumping horses); livestock (e.g., alpaca, banteng, bison, camel, cattle, deer, donkey, gayal, goat, llama, mule, pig, reindeer, sheep, water buffalo, yak, etc.); laboratory animals (e.g., mice, rabbits, rats, non-human primates); and undomesticated animals held in captivity, e.g. in zoological parks and the like. In other embodiments, particularly when the disease being prevented or treated is heartworm, the subject is a dog or a cat, typically a dog.

In various embodiments, a therapeutically effective amount of the immunogenic composition described herein is administered to the subject. As used herein "a therapeutically effective amount" is an amount that provides a therapeutic effect for a given condition and administration regimen. In particular aspects of the disclosure, a "therapeutically effective amount" refers to an amount of a polypeptide, immunogenic composition, or vaccine of the present disclosure that when administered to an animal brings about a positive therapeutic response with respect to the prevention or treatment of a subject for diseases or conditions associated with filarial worms such as *Brugia malyai, Wuchereria bancrofti, Onchocerca volvulus, Loa loa,* or *Dirofilaria immitis*. For example, a positive therapeutic response in regard to treating diseases or conditions associated with filarial worms includes curing or ameliorating the symptoms of the disease.

A positive therapeutic response with respect to preventing a condition associated with a filarial infection includes, for example, the production of filarial antibodies by the subject in a quantity sufficient to protect against development of the disease. The production of antibodies elicited by a treatment is readily ascertained by obtaining a plasma or serum sample from the subject to which an immunogenic composition is administered, and assaying the antibodies therein for their ability to bind to the polypeptide(s) used to elicit the immune response to filarial worms. Exemplary methods include, but are not limited to, ELISA assays, immunofluorescence assays (IFA), or other immunoassays such as a Western blots, as is well known in the art.

The exact dosage is chosen by the individual physician in view of the patient to be treated. Dosage and administration are adjusted to provide sufficient levels of the active moiety or to maintain the desired effect. Additional factors that may be taken into account include the prevalence of filarial worms in the geographical vicinity of the patient, the severity of the disease state of the patient, age, and weight of the patient, diet, time and frequency of administration, drug combination(s), reaction sensitivities, and tolerance/response to therapy. An appropriate effective amount may be readily determined using only routine experimentation. Several doses may be needed per individual in order to achieve a sufficient response to effect treatment. Suitable regimes for initial administration and follow-up administration (e.g., booster shots) are also variable, but are typified by an initial administration followed in intervals (weeks or months) by a subsequent administration. In some embodiments, typical dosages may range from about 0.01 to about 20 mg/kg, and more particularly from about 0.1 to about 10 mg/kg.

EXAMPLES

Example 1. Materials and Methods

Dissections

Adult *Brugia malayi* worms were received in multiple shipments from TRS Labs (Athens, Ga.) and frozen at −80° C. until processing. For separation of anatomic structures, worms were thawed at room temperature and then dissected using a stereomicroscope and fine tipped forceps. One set of forceps was used to grip and steady the center of the parasite after thawing and placement into a petri dish filled with phosphate buffered saline (PBS). Another set of forceps was used to grasp and gently twist the parasite close to the first set of forceps, resulting in a tear of the body wall. The cephalic tip of the body wall was then grasped and gently peeled away from the rest of the organs. The caudal portion of the body wall was then peeled away from the intestines and uterine tubes (FIG. 2). Reproductive organs were identified by their anterior junction and then separated from the intestine. Each anatomic fraction (intestine, reproductive tract, and body wall) was placed in a microcentrifuge tube filled with PBS. These were stored at −20° C. until protein extraction.

Protein Extraction

The samples were thawed and then centrifuged in 1.5 ml eppendorf tubes. The pelleted tissues were frozen and thawed 4 times by cycling through placement on dry ice for 10 minutes followed by placement in a 37° C. water bath. Using a mini disposable micropestle, the samples were homogenized with 50 μl of UPX extraction buffer (Expedeon). The micropestle was washed with 50 μl of UPX extraction buffer and processed as per the manufacturer's instructions. In brief, samples were placed in a 100° C. water bath for 5 minutes, removed and cooled at 4° C. for one hour. Samples were then centrifuged at 15,000×g for 10 minutes and supernatant was collected.

Protein Concentrations were measured by BCA assay. 400 μg proteins of intestine, body wall and reproductive tract each were reduced, alkylated and trypsin digested overnight following filter-aided digestion procedure using a FASP digestion kit (Protein Discovery, San Diego, Calif.) according to vendor protocol. Tryptic peptides were further desalted, lyophilized and reconstituted in 25% acetonitrile with 0.1% formic acid and further fractionated using strong cation exchange (SCX) chromatography. The SCX fractions of the three samples were pooled into 16 to 18 fractions each, lyophilized and reconstituted in 0.1% trifluoroacetic acid to be analyzed by liquid chromatography-mass spectrometry (LC-MS).

Nanobore Reversed-Phase Liquid Chromatography Tandem MS (nanoRPLC-MSMS)

Nanobore RPLC-MSMS was performed using an Agilent 1200 nanoflow LC system coupled online with a LTQ Orbitrap XL mass spectrometer. The RPLC column (75 μm i.d.×10 cm) were slurry-packed in-house with 5 μm, 300 Å pore size C-18 stationary phase into fused silica capillaries with a flame pulled tip. After sample injection, the column was washed for 20 minutes with 98% mobile phase A (0.1% formic acid in water) at 0.5 μl/min. Peptides were eluted using a linear gradient of 2% mobile phase B (0.1% formic acid in acetonitrile) to 35% B in 100 minutes, then to 80% B over an additional 40 minutes. The column flow-rate was maintained at 0.25 μl/min throughout the separation gradient. The mass spectrometer was operated in a data-dependent mode in which each full MS scan was followed by seven MS/MS scans wherein the seven most abundant molecular ions were dynamically selected for collision-induced dissociation (CID) using a normalized collision energy of 35%.

Protein Identification

The LC-MS/MS data were searched using SEQUEST through Bioworks interface against a combined database of *Brugia malayi* database downloaded from The Institute for Genomic Research (TIGR) and the Wolbachia database from New England Biolabs (Beverly, Mass.). SEQUEST was searched with a fragment ion mass tolerance of 0.50 Da and a parent ion tolerance of 25 PPM. Carbamidomethyl of cysteine was specified in SEQUEST as a fixed modification. Oxidation of methionine was specified in SEQUEST as a variable modification. Scaffold (version Scaffold 3.5.2, Proteome Software Inc., Portland, Oreg.) was used to validate MS/MS based peptide and protein identifications. Peptide identifications were accepted if they could be established at greater than 95.0% probability by the Peptide Prophet algorithm (Keller et al., 2002, Anal. Chem., 74, 5383-5392, herein incorporated by reference). Protein identifications were accepted if they could be established at greater than 99.0% probability and contained at least 2 identified peptides. Protein probabilities were assigned by the Protein Prophet algorithm (Nesvizhskii et al., 2003, Anal. Chem., 75, 4646-4658, herein incorporated by reference). Proteins that contained similar peptides and could not be differentiated based on MS/MS analysis alone were grouped to satisfy the principles of parsimony. TIGR accession numbers were matched to PUB_loci from the proteome published by Bennuru et. Al., 2011, Proc. Natl. Acad. Sci. U.S.A., 108, 9649-9654, herein incorporated by reference.

Heat Map Analysis

A heat map of the relative abundance of each protein, defined as the number of unique matching peptides within each anatomic fraction, was made with JMP software.

Quantitative Analysis

Protein quantitation was determined by normalized spectral abundance. This approach provides a theoretical quantitative value useful for determining relative abundance of a single protein between samples (McIlwain et al., 2012, BMC Bioinformatics, 13, 308, Paoletti et al., 2006, Proc. Natl. Acad. Sci. U.S.A., 103, 18928-18933) and an estimation of relative abundance between different proteins in one sample (Liu et al., 2004, Anal. Chem., 76, 4193-4201). Exclusive spectral counts, spectra that match to only 1 protein, were first divided by the length of the protein to account for the differences in numbers of possible spectra. This calculation provides the spectral abundance factor. This was then normalized to obtain the normalized spectral abundance factor (NSAF) by dividing by the sum of the total spectral abundance factors found within that anatomic fraction.

$$NSAF = \frac{\left(\frac{\text{Spectra}}{\text{Length}}\right)p}{\sum_{p=1}^{n}\left(\frac{\text{Spectra}}{\text{length}}\right)p}.$$

NSAF enrichment was then calculated by dividing the NSAF of a given protein in the target fraction divided by the sum of the NSAF of the other two fractions to determine whether a protein was more abundant or "enriched" in one fraction compared to the others.

$$NSAF \text{ enrichment} = \frac{NSAF \text{ (target fraction)}}{NSAF \text{ of other two fractions (added)}}.$$

Proteins were considered enriched when they had an NSAF enrichment value of 2 or greater.

Functional Categories for Gene Set Enrichment Analysis (GSEA)

The proteome of B. malayi had previously been functionally characterized by Bennuru and colleagues (Bennuru, et al., 2011). For proteins previously annotated for function, no further analysis of function was carried out. The 665 newly identified proteins were annotated based loosely on the KOG and PFAM functions. Categories of function were used as previously described (Bennuru, et al., 2011), including cytoskeletal, extracellular matrix, immunological, metabolism, nuclear regulation, protein export, protein modification, protein synthesis, signal transduction, transcription, transporters, and uncharacterized. Functions of anatomic fractions were analyzed based on GSEA, which analyzes the data for bias in a condition (or anatomic fraction) (Subramanian et al., 2005, Proc. Natl. Acad. Sci. U.S.A., 102, 15545-15550, herein incorporated by reference). Proteins were ranked according to abundance using spectral counts. A priori defined sets of proteins, based on functional annotation, were then analyzed using GSEA for bias within each anatomic fraction.

BLASTp

BLASTp was performed on proteins of interest from B. malayi to identify similarity among W. bancrofti, O. volvulus, D. immitis, L. boa, and H. sapiens. BLAST query was conducted with blast+ 2.2.29 downloaded from NCBI. Protein databases for W. bancrofti, O. volvulus, H. sapiens, L. loa were downloaded from uniprotKB. Protein database for D. immitis was downloaded from nematodes.org. A FASTA file containing the B. malayi proteins of interest were blasted against each other genome individually. Percent identity and query coverage were recorded for the top scoring sequence for each protein. Score is determined by an algorithm that takes into account similarity of AA sequence, gaps in homologous regions, and length of homology. Percent identity is defined as the percentage of amino acids that match perfectly over the sequence region with greatest homology.

Example 2. Results

Distinct Anatomic Fractions Exhibit Markedly Different Expression of Proteins

Figure 3A:
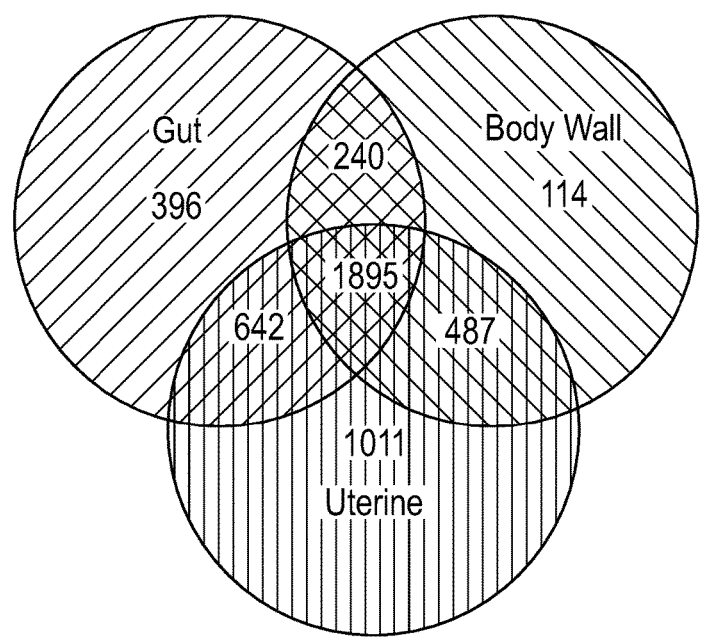
FIG. 3A depicts a Venn diagram of proteins identified within each anatomic fraction of adult female *Brugia malayi* based on a 2 peptide minimum for identification as described in the Examples.
Figure 3B:
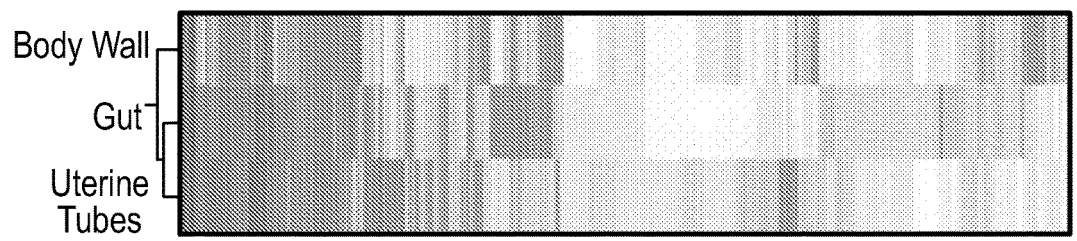
FIG. 3B depicts a heat map of hierarchical clustered proteins found within the different anatomic fractions of adult female *B. malayi*.

Based on a match of 2 unique peptides to a protein, we identified a total of 5023 proteins. Of these, 204 were Wolbachia proteins, and 34 could be matched to more than 1 specific protein, leaving 4,785 specifically identified B. malayi proteins. While 1,895 of the proteins were identified by two peptides in all three anatomical fractions of the parasite, 396 proteins were identified solely within the intestine, 114 solely within the body wall, and 1011 solely within the uterine tubes (data not shown). Additionally, although the majority of proteins were present in all three anatomic fractions, we found that there was a differential expression of each protein among the anatomic fractions (FIG. 3).

Figure 4:
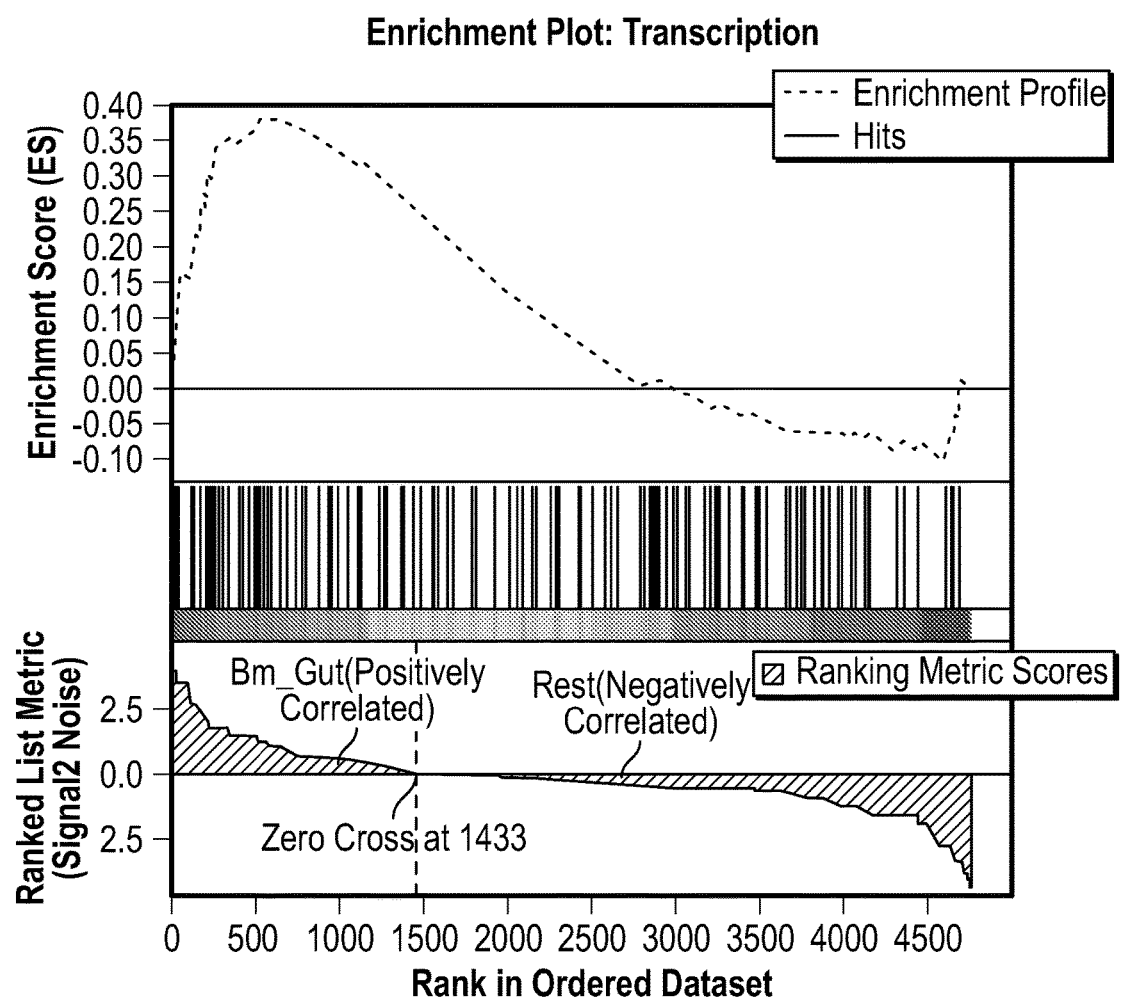
FIG. 4 depicts the association of transporter proteins with the intestine as measured by gene set enrichment analysis (GSEA) P-value=0.005, as described in the Examples.

Proteomic Profiling of the B. malayi Intestine is Consistent with Functional Absorption and Digestion Like all nematodes, filarial parasites have a fully formed intestine. However, the functionality of this tract is not completely clear (Munn, E. A. and Munn, P. D., 2002, Feeding and Digestion. In: Lee, D. L., (Ed., The Biology of Nematodes. CRC Press Taylor and Francis Group, Boca Raton, Fla., pp. 211-233, herein incorporated by reference). We performed several analyses to further elucidate the possible function of the intestine in B. malayi. First, gene set enrichment analysis (GSEA) was performed which showed a bias for proteins with transporter function to be present within the intestine (FIG. 4). Next, we rank ordered the proteins that were enriched within the intestine based on their NSAF value, a measure which takes into account the number of spectra uniquely matching to a protein and the length of the protein in amino acids. Spectral counting has previously been shown to be useful to determine relative abundance of a single protein in different samples (McIlwain, et al., 2012, Paoletti, et al., 2006) and provide a reasonable approximation of protein abundance within a sample compared to other proteins in the same sample (Liu, et al., 2004). Of the 20 most abundant, enriched, and named intestine proteins, 3 are proteolytic enzymes (Bm1_00205, Bm1_18805, Bm1_34740), 2 are transporters (Bm1_42930, and Bm1_24840), and 1 is associated with phagocytosis (Bm1_02265). The abundance of such proteins suggests the intestine is involved in both digestion and active absorption of nutrients. Of the remaining 20 most abundant named proteins in the intestine, 3 are muscle associated proteins (Bm1_28910, Bm1_45035, Bm1_00655) and the rest are involved in various functions including translation, cell trafficking, RNA binding, cell adhesion, hydrolysis, lipid metabolism, catabolism, and cellular structure.

Table 1, below, depicts the twenty most abundant proteins, with proper names, enriched in the intestine of adult female B. malayi based on normalized spectral abundance factor (NSAF). The NSAF enrichment values are also depicted. "Specific" means that the protein was only found within the intestine.

TABLE 1

| Protein Type | Accession | Name | Abundance NSAF Intestine | NSAF enrichment Intestine |
|---|---|---|---|---|
| Translational | Bm1_41515 | 40S ribosomal protein S21, putative | 5.4E−03 | 2.17 |
| Muscle Associated | Bm1_28910 | Calsequestrin, skeletal muscle isoform precursor, putative | 2.5E−03 | 2.90 |
| Cell trafficking | Bm1_14235 | SNARE domain containing protein | 2.4E−03 | 2.0 |
| Muscle Associated | Bm1_45035 | Probable myosin regulatory light chain, putative | 2.2E−03 | 2.5 |
| Protease | Bm1_34740 | aspartic protease BmAsp-1, identical | 1.1E−03 | 16.0 |
| carrier protein | Bm1_21135 | Acyl CoA binding protein | 9.0E−04 | 7.68 |
| Muscle Associated | Bm1_00655 | myosin heavy chain, nonmuscle type 1, putative | 7.8E−04 | 2.0 |
| Phagocytosis associated | Bm1_02265 | MGC69076 protein-related | 7.3E−04 | 3.77 |
| Xenobiotic metabolism | Bm1_13480 | UDP-glucoronosyl and UDP-glucosyl transferase family protein | 7.0E−04 | 28.16 |
| RNA binding | Bm1_20295 | Glycine-rich RNA-binding protein.-related | 6.9E−04 | 8.96 |
| Miscellaneous | Bm1_25280 | Prion-like--related | 6.4E−04 | 2.37 |
| Cell Adhesion | Bm1_10500 | AMOP domain containing protein | 6.1E−04 | 5.99 |
| Hydrolase | Bm1_24820 | Histidine acid phosphatase family protein | 6.1E−04 | 6.32 |
| Cytoskeleton | Bm1_30265 | Tubulin alpha chain, putative | 5.9E−04 | 2.95 |
| Transporter | Bm1_42930 | Excitatory amino acid transporter, putative | 5.7E−04 | 2.75 |
| Lipid Metabolism | Bm1_08150 | NAD-dependent malic enzyme, mitochondrial precursor, putative | 5.5E−04 | 7.10 |
| Catabolism | Bm1_48185 | putative amidase | 5.1E−04 | 3.74 |
| Transporter | Bm1_24840 | Major Facilitator Superfamily protein | 4.7E−04 | 19.88 |
| Protease | Bm1_18805 | Papain family cysteine protease containing protein | 4.4E−04 | Specific |
| Protease | Bm1_00205 | ShTK domain containing protein | 4.2E−04 | 3.42 |

Many Predominant Body Wall Enriched Proteins Provide Muscular Structure or are Involved in Muscular Contraction The body wall of *B. malayi* includes, from superficial to deep, the epicuticle, cuticle, epidermis, musculature (divided into a superficial fibrous portion and a deeper metabolically active portion) and the lateral cords (FIG. 4). The musculature is separated into quadrants by the lateral, ventral and dorsal cords with up to 9 myocytes per quadrant (Vincent et al., 1975, J. Parasitol., 61, 499-512.). The lateral cords contain the cell bodies of the epidermis, which produces and maintains the cuticle. Also associated with the lateral cords is a secretory gland which is connected to the secretory pore by the secretory canal (Landmann et al., 2010, PLoS Negl. Trop. Dis., 4, e758) herein incorporated by reference. The ventral and dorsal cords are associated with nerves that innervate the musculature.

Figure 5A:
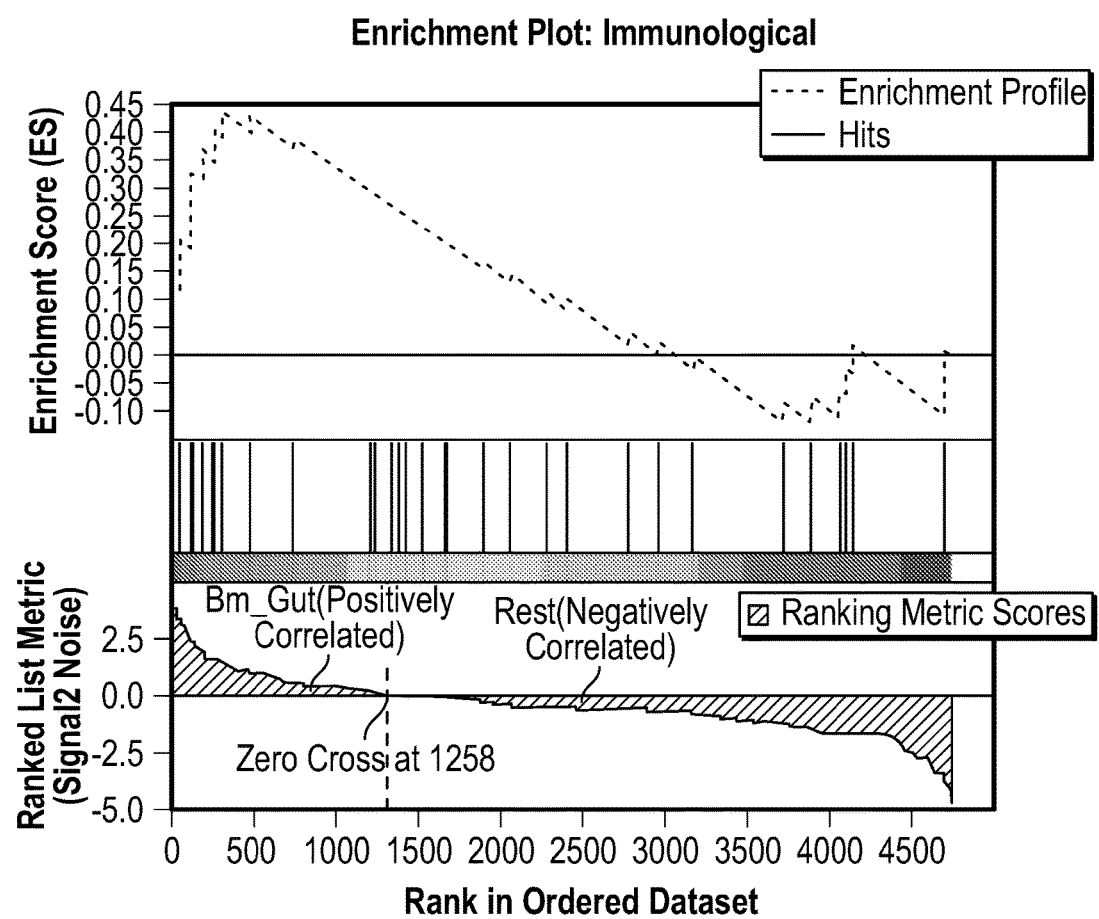
FIG. 5A depicts the association of immunological (P-value=0.003) proteins with the body wall of the adult female *B. malayi* as measured by GSEA, as described in the Examples.
Figure 5B:
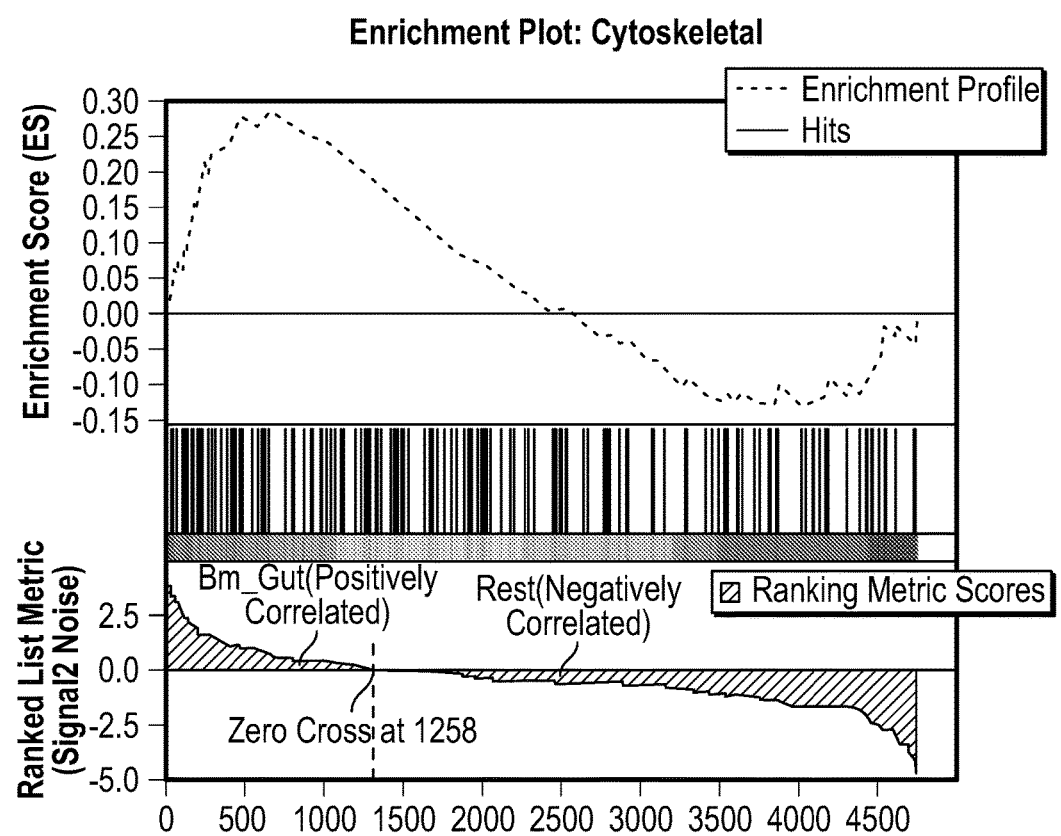
FIG. 5B depicts the association of cytoskeletal proteins (P-value=0 0.009) with the body wall of the adult female *B. malayi* as measured by GSEA, as described in the Examples.

GSEA of the body wall showed a bias for cytoskeletal proteins and proteins of immunological interest to be present within the body wall (FIG. 5). Further, analysis of the 20 most abundant named proteins that were enriched within the body wall by NSAF yielded 12 proteins associated with muscle structure or regulation of muscular contraction (Table 2). These included an actin (Bm1_21705), 4 myosins (Bm1_40715, Bm1_50805, Bm1_00935, Bm1_14060), 2 paramyosins (Bm1_04450, Bm1 02615), 1 tropomyosin (Bm1_02060), and a disorganized muscle protein (Bm1_40320). In addition to the muscular proteins, there were 3 cuticular proteins, a glutathione peroxidase, which provides protection from oxidative damage, a cytoskeletal protein, a heat shock protein, and a glutamine synthetase.

Table 2, below, depicts the twenty most abundant proteins enriched in the body wall of adult female *Brugia malayi*.

TABLE 2

| Protein type | Accession | Name | Abundance (NSAF) Body Wall | NSAF enrichment Body Wall |
|---|---|---|---|---|
| Muscle associated | Bm1_21705 | actin 1, putative | 6.2E−02 | 3.86 |
| Cytoskeletal | Bm1_45215 | intermediate filament protein, putative | 2.0E−02 | 2.94 |
| Muscle associated | Bm1_40320 | Disorganized muscle protein 1, putative | 1.6E−02 | 5.15 |
| HSP | Bm1_19805 | small heat shock protein, putative | 1.4E−02 | 7.97 |
| Muscle associated | Bm1_04450 | Paramyosin, putative | 1.1E−02 | 5.87 |
| Muscle associated | Bm1_02615 | Paramyosin, identical | 1.0E−02 | 6.33 |
| Calcium Binding | Bm1_48810 | EF hand family protein | 6.5E−03 | 9.81 |
| Cuticle | Bm1_13015 | Nematode cuticle collagen N-terminal domain containing protein | 6.1E−03 | 3.05 |

TABLE 2-continued

| Protein type | Accession | Name | Abundance (NSAF) Body Wall | NSAF enrichment Body Wall |
|---|---|---|---|---|
| Muscle associated | Bm1_01235 | Tropomyosin-related | 6.0E−03 | 5.24 |
| Muscle Associated | Bm1_49075 | Calponin homolog OV9M, putative | 5.9E−03 | 3.31 |
| Muscle associated | Bm1_40715 | myosin heavy chain, putative | 5.8E−03 | 3.11 |
| Cuticle | Bm1_54705 | Nematode cuticle collagen N-terminal domain containing protein | 5.5E−03 | 6.57 |
| Muscle associated | Bm1_50805 | Myosin tail family protein | 4.7E−03 | 4.00 |
| Antioxidant | Bm1_40465 | Cuticular glutathione peroxidase precursor, putative | 4.5E−03 | 2.59 |
| Muscle associated | Bm1_00935 | myosin heavy chain B (MHC B), putative | 4.4E−03 | 3.36 |
| Carbohydrate metabolism | Bm1_16060 | carbohydrate phosphorylase, putative | 4.2E−03 | 2.67 |
| Muscle associated | Bm1_14060 | myosin heavy chain B (MHC B), putative | 4.1E−03 | 2.23 |
| Cuticle | Bm1_17485 | Nematode cuticle collagen N-terminal domain containing protein | 3.2E−03 | 2.40 |
| Muscle associated | Bm1_02060 | Tropomyosin family protein | 3.2E−03 | 3.19 |
| Amino Acid Synthesis | Bm1_53470 | glutamine synthetase, putative | 3.0E−03 | 3.16 |

Figure 6A:
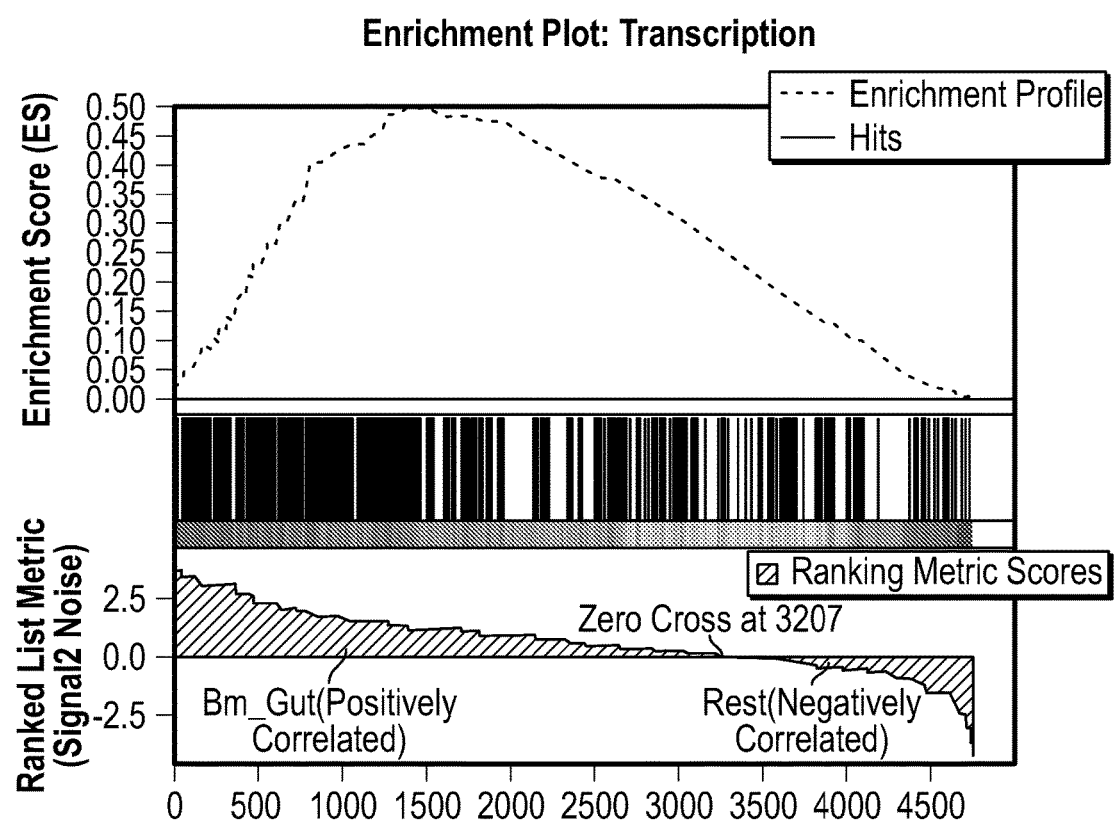
FIG. 6A depicts the association of transcription (P<0.001 with the reproductive tract of adult female *B. malayi* as described in the Examples.
Figure 6B:
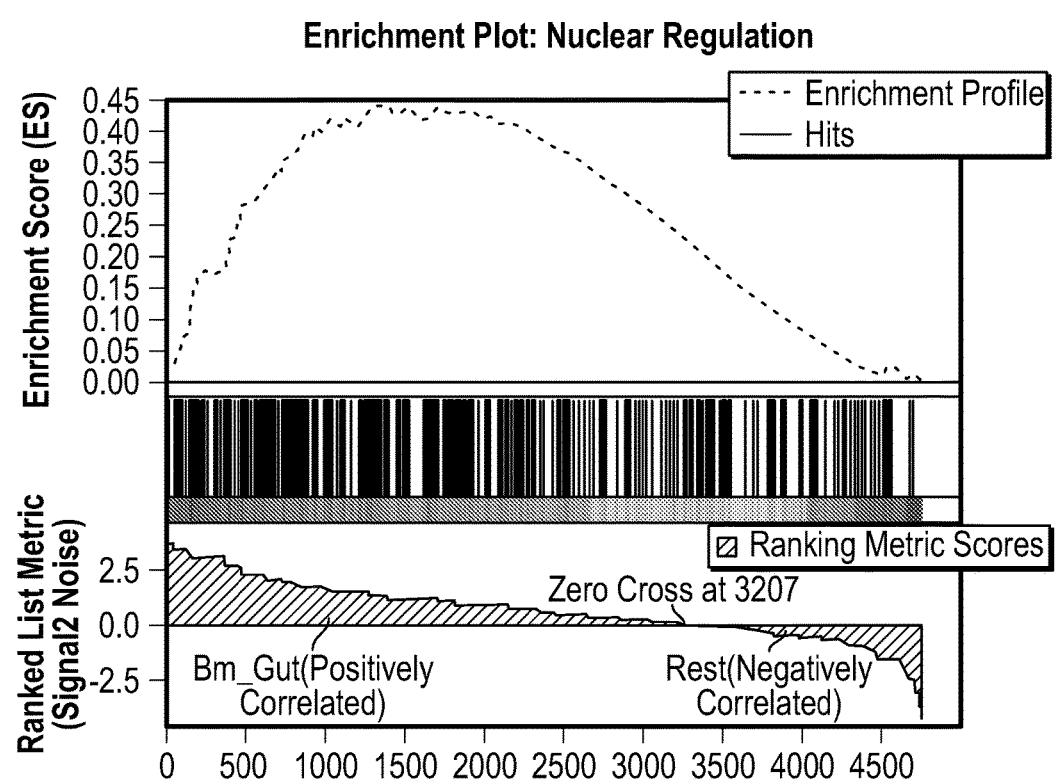
FIG. 6B depicts the association of nuclear regulation proteins (P=0.013) with the reproductive tract of adult female *B. malayi* as described in the Examples.

Nuclear Regulatory Proteins, Including Those Involved in Chromatin Organization are Enriched and Highly Abundant in the Reproductive Tract The nematode female reproductive tract consists of two ovaries where gamete production takes place, two seminal receptacles (aka spermatheca) which store sperm obtained from males, and 2 uterine tubes that allow for embryo and subsequent in utero microfilaria development (FIG. 1). The two uterine tubes merge into the vulva, which is on the ventral surface of the worm in the cephalic region (Fischer et al., 2011, PLoS Negl. Trop. Dis., 5, e1174. Jiang et al., 2012, Int. J. Parasitol., 42, 841-850, Landmann, et al., 2010, Li et al., 2012, BMC Genomics, 13, 184, which are herein incorporated by reference in their entireties). GSEA showed a bias for transcription and nuclear regulation proteins to be present within the female reproductive tract (FIG. 6). Similarly the 20 most abundant named proteins that were enriched in the reproductive tract as assessed by NSAF contained many proteins involved in nuclear regulation. 12 proteins contained domains associated with nucleotide binding or splicing, with 8 of these 12 being histones or histone linkers (Bm1_02505, Bm1_02515, Bm1_20280, Bm1_02495, Bm1_, 20285, Bm1_, 38685, Bm1_02800, Bm1_04110). Three microfilarial sheath proteins were also abundant and enriched within the reproductive tract, which is consistent with presence of developing microfilariae within the uterine tubes. The remaining 7 proteins are involved in trafficking, protection from oxidation, xenobiotic metabolism, proteolysis and cell adhesion.

Table 3, below, depicts the most abundant enriched named proteins in the reproductive tract of adult female *Brugia malayi*. Specific means that the protein was only found within the reproductive tract.

TABLE 3

| Protein Type | | | Abundance NSAF Reproductive tract | NSAF Enrichment Reproductive tract |
|---|---|---|---|---|
| Chromatin organization | Bm1_02505 | histone H2A, putative | 3.4E−02 | 8.1 |
| Chromatin organization | Bm1_02515 | histone H4, putative | 3.1E−02 | 2.7 |
| Chromatin organization | Bm1_20280 | Probable histone H2B 3, putative | 1.1E−02 | 4.3 |
| Chromatin organization | Bm1_02495 | histone H3, putative | 7.8E−03 | 25.9 |
| Sheath | Bm1_19100 | Major microfilarial sheath protein precursor.-related | 6.2E−03 | 2.6 |
| Chromatin organization | Bm1_20285 | histone H2A, putative | 5.9E−03 | 17.2 |
| Chromatin organization | Bm1_38685 | Histone H2A variant, putative | 3.4E−03 | 2.7 |
| Sheath | Bm1_05185 | sheath protein 5, identical | 2.8E−03 | 2.9 |
| Trafficking | Bm1_07925 | peroxisomal membrane anchor protein, putative | 2.2E−03 | 2.6 |
| Antioxidant | Bm1_44840 | Glutathione S-transferase, N-terminal domain containing protein | 2.0E−03 | 2.3 |

TABLE 3-continued

| Protein Type | | | Abundance NSAF Reproductive tract | NSAF Enrichment Reproductive tract |
|---|---|---|---|---|
| DNA binding | Bm1__25620 | high mobility group protein, putative | 1.7E−03 | 10.2 |
| Sheath | Bm1__00650 | microfilarial sheath protein, identical | 1.2E−03 | 2.4 |
| RNA splicing | Bm1__49560 | NOP5/NOP58, putative | 1.2E−03 | 2.2 |
| RNA modulation | Bm1__49460 | small nuclear ribonucleoprotein-associated protein homolog F9F13.90 - *Arabidopsis thaliana*, putative | 1.1E−03 | 2.3 |
| Chromatin organization | Bm1__57630 | retinoblastoma-binding protein., putative | 1.1E−03 | 2.6 |
| Chromatin organization | Bm1__04110 | linker histone H1 and H5 family protein | 9.6E−04 | 4.7 |
| Xenobiotic metabolism | Bm1__32235 | Flavin-binding monooxygenase-like family protein | 9.4E−04 | 2.6 |
| Chromatin organization | Bm1__02800 | Histone H2B 2, putative | 9.0E−04 | Specific |
| Protease | Bm1__45620 | Trypsin family protein | 8.9E−04 | 36.5 |
| Cell Adhesion | Bm1__17270 | Fasciclin domain containing protein | 8.1E−04 | 2.8 |

Identification of Potential Intestine Vaccine Candidates

To identify gastrointestinal proteins that could potentially be used as vaccine candidates, we analyzed the proteomics set for proteins that were enriched in the intestine, had at least one predicted transmembrane domain, and were not predicted to be in the mitochondria. We sought luminal surface proteins because these proteins may be accessible to host antibodies after vaccination. 106 proteins were identified with these criteria (Table A and Table B, below, provided after the Examples) and were categorized based on likely metabolic function within the cell. The amino acid sequences identified by Genbank Accession numbers in Table. A and Table B are herein incorporated by reference.

In order to evaluate the potential of the 106 surface proteins as pan-filarial vaccine candidates, we performed a blast search for each protein against databases for *Homo sapiens*, *Wuchereria bancrofti*, which causes lymphatic filariasis, *Onchocerca volvulus*, which causes river blindness, *L. loa*, which causes loiasis, and *Dirofilaria immitis*, which causes heartworm. Proteins were selected that contained a percent identity of >75% to *W. bancrofti* or *O. volvulus* and <40% homology to humans. 72 proteins matched these criteria.

We then selected those proteins that had 1-2 transmembrane domains for ease of recombinant protein production. These were evaluated with Interpro software for the presence of non-cytoplasmic domains that could be bound by host antibodies. 27 proteins matched all of these criteria (Tables C and D, below, provided after the Examples), with 12 displaying substantial homology between all of the filarial species. Of these 27 proteins, 10 are hypothetical proteins, 3-4 are proteases, 2 are involved in xenobiotic metabolism using glucuronidation, 2 participate in cell adhesion, 2 function in cell signaling, and 2 are chaperones.

Certain Excretory/Secretory (ES) Products are Associated with Specific Anatomic Fractions 227 proteins were found within the ES product of adult female *B. malayi* in a previous study by Bennuru and colleagues (Bennuru et al., 2009, PLoS Negl. Trop. Dis., 3, e410, herein incorporated by reference). To better define the origin of these proteins, we analyzed all adult female ES proteins for enrichment within any of the three worm fractions from this study. Four (1.7%) of these proteins were either enriched or specific to the intestine (Table 4). The most notable of these was the papain family cysteine protease (Bm1_18805). Eight (3.5%) female ES products were enriched within the body wall (Table 5), including two proteins that protect against oxidative damage, cuticular glutathione peroxidase (Bm1_40465) and peptide methionine sulfoxide reductase (Bm1_10795) (Weissbach, et al., 2005). Other ES products enriched within the body wall included a cuticle collagen (Bm_13015), and muscular proteins.

There were 30 adult female ES products (13%) enriched within the female reproductive tract (Table 6). Some of these antigens include Juv-p120 (Bm1_18010), which has been implicated in being critical for MF survival, Von willebrand factor type A domain containing protein (Bm1_27495), which likely binds to collagen, a trypsin inhibitor (Bm1_03520), and an aspartyl amino peptidase (Bm1_16690).

Tables 4, 5, and 6 below depict the intestine-enriched, body-wall enriched, and reproductive tract-enriched ES products, respectively. "Specific" means that the protein was only was only identified within the specified anatomical fraction.

TABLE 4

| ID | Name | Abundance (NSAF) Body wall | NSAF Enrichment Body wall |
|---|---|---|---|
| Bm1__13015 | Nematode cuticle collagen N-terminal domain containing protein | 6.1E−03 | 3.05 |
| Bm1__50805 | Myosin tail family protein | 4.7E−03 | 4.00 |
| Bm1__40465 | Cuticular glutathione peroxidase precursor, putative | 4.5E−03 | 2.59 |
| Bm1__39425 | protein unc-22, putative | 8.8E−04 | 7.42 |
| Bm1__26690 | Prion-like-, putative | 8.0E−04 | 4.73 |
| Bm1__12515 | Immunoglobulin I-set domain containing protein | 4.5E−04 | 7.68 |

TABLE 4-continued

| ID | Name | Abundance (NSAF) Body wall | NSAF Enrichment Body wall |
|---|---|---|---|
| Bm1_45145 | Ryanodine Receptor TM 4-6 family protein | 1.4E−04 | 3.67 |
| Bm1_10795 | Peptide methionine sulfoxide reductase family protein | 9.6E−05 | Specific |

TABLE 5

| ID | Name | Abundance (NSAF) Body wall | NSAF Enrichment Body wall |
|---|---|---|---|
| Bm1_13015 | Nematode cuticle collagen N-terminal domain containing protein | 6.1E−03 | 3.05 |
| Bm1_50805 | Myosin tail family protein | 4.7E−03 | 4.00 |
| Bm1_40465 | Cuticular glutathione peroxidase precursor, putative | 4.5E−03 | 2.59 |

TABLE 5-continued

| ID | Name | Abundance (NSAF) Body wall | NSAF Enrichment Body wall |
|---|---|---|---|
| Bm1_39425 | protein unc-22, putative | 8.8E−04 | 7.42 |
| Bm1_26690 | Prion-like-, putative | 8.0E−04 | 4.73 |
| Bm1_12515 | Immunoglobulin I-set domain containing protein | 4.5E−04 | 7.68 |
| Bm1_45145 | Ryanodine Receptor TM 4-6 family protein | 1.4E−04 | 3.67 |
| Bm1_10795 | Peptide methionine sulfoxide reductase family protein | 9.6E−05 | Specific |

TABLE 6

| ID | Name | Abundance (NSAF) Reproductive Tract | NSAF Enrichment Reproductive Tract |
|---|---|---|---|
| Bm1_29260 | 60S ribosomal protein L34, putative | 4.6E−04 | 2.4 |
| Bm1_20440 | Biotin/lipoate A/B protein ligase family protein | 4.5E−04 | 2.8 |
| Bm1_43080 | hypothetical protein | 3.7E−04 | 2.1 |
| Bm1_02485 | Potential global transcription activator SNF2L, putative | 2.5E−04 | 2.6 |
| Bm1_16970 | hypothetical protein | 1.8E−04 | 2.7 |
| Bm1_16690 | Aspartyl aminopeptidase, putative | 1.6E−04 | 3.4 |
| Bm1_18010 | excretory/secretory protein Juv-p120 precursor-related | 1.4E−04 | 3.4 |
| Bm1_21390 | RNA binding protein, putative | 1.3E−04 | 2.0 |
| Bm1_48000 | RAS FAMILY PROTEIN | 1.1E−04 | 2.7 |
| Bm1_12225 | G-patch domain containing protein | 1.0E−04 | 3.9 |
| Bm1_03520 | Kunitz/Bovine pancreatic trypsin inhibitor domain containing protein | 9.9E−05 | 2.8 |
| Bm1_02770 | Galactosyltransferase family protein | 8.5E−05 | 2.6 |
| Bm1_48025 | Alpha-catulin, putative | 7.5E−05 | 3.5 |
| Bm1_41495 | Gex interacting protein protein 4, isoform c-related | 7.2E−05 | 7.0 |
| Bm1_18480 | HYPOTHETICAL PROTEIN | 7.2E−05 | Specific |
| Bm1_46460 | 26S PROTEASOME REGULATORY CHAIN 4, PUTATIVE | 6.4E−05 | 5.4 |
| Bm1_49790 | tRNA modification GTPase TrmE family protein | 5.1E−05 | 2.0 |
| Bm1_27495 | von Willebrand factor type A domain containing protein | 4.9E−05 | 2.1 |
| Bm1_46930 | HYPOTHETICAL PROTEIN | 4.4E−05 | 2.1 |
| Bm1_21025 | hypothetical protein, conserved | 4.3E−05 | 3.4 |
| Bm1_25670 | hypothetical protein | 4.0E−05 | Specific |
| Bm1_41650 | hypothetical protein | 3.2E−05 | 4.1 |
| Bm1_54890 | RNA recognition motif. | 3.0E−05 | 2.0 |
| Bm1_16685 | hypothetical protein | 2.7E−05 | 2.7 |
| Bm1_40395 | Phosphatidylinositol 3- and 4-kinase family protein | 2.6E−05 | 4.3 |
| Bm1_00750 | RhoGEF domain containing protein | 1.9E−05 | 3.4 |
| Bm1_25450 | Formin Homology 2 Domain containing protein | 1.8E−05 | Specific |
| Bm1_05305 | HYPOTHETICAL PROTEIN, CONSERVED | 1.7E−05 | Specific |
| Bm1_42420 | Eye-specific diacylglycerol kinase, putative | 1.6E−05 | Specific |
| Bm1_17115 | conserved hypothetical protein | 9.8E−06 | Specific |

Summary of the Results

In conclusion, the results detail the proteins found within the major anatomic fractions of *B. malayi*, including the intestine, body wall, and reproductive tract. The results suggest that the intestine of adult filarial worms likely plays an important role in digestion and absorption, and may have other physiologic functions that have not yet been characterized. Further, we have identified vaccine candidates from the *B. malayi* intestine that that could be protective against all major filarial pathogens of humans, and which may provide protective efficacy as vaccines against the causative agents of lymphatic filariasis, river blindness, loiasis as well as heartworm.

Sequences

The sequence identifiers described herein and the sequences set forth in the following sequence listing correspond to the Accession numbers and descriptions described in Table 7, below.

TABLE 7

| SEQ ID NO: | | Gene Symbol and Protein Type | Description |
|---|---|---|---|
| | | Cell Adhesion | |
| 1 | XP_001899381 | Bm1_39630 | Immunoglobulin I-set domain containing protein |
| 2 | XP_001892066 | Bm1_02820 | EGF-like domain containing protein |
| | | Cell Signaling | |
| 3 | XP_001897556 | Bm1_30585 | Tyrosine-protein kinase abl-1.-related |
| 4 | XP_001895334 | Bm1_19395 | Protein kinase domain containing protein |
| 5 | XP_001899110 | Bm1_38285 | Ser/Thr protein phosphatase family protein |
| | | Chaperone/HSP | |
| 6 | XP_001894589 | Bm1_15660 | DnaJ domain containing protein |
| 7 | XP_001895946 | Bm1_22450 | hemimethylated DNA binding domain containing protein |
| | | Glycosylation/ glucuronidation | |
| 8 | XP_001900394 | Bm1_44655 | Fukutin.-related |
| 9 | XP_001894161 | Bm1_13480 | UDP-glucoronosyl and UDP-glucosyl transferase family protein |

TABLE 7-continued

| SEQ ID NO: | | Gene Symbol and Protein Type | Description |
|---|---|---|---|
| | | Miscellaneous | |
| 10 | XP_001901384 | Bm1_49590 | CG3054-PA-related |
| 11 | XP_001893572 | Bm1_10500 | AMOP domain containing protein |
| 12 | XP_001901064 | Bm1_48010 | EGF-like domain containing protein |
| | | Proteases | |
| 13 | XP_001899113 | Bm1_38300 | Peptidase family M1 containing protein |
| 14 | XP_001893672 | Bm1_11005 | MGC84665 protein-related |
| 15 | XP_001902078 | Bm1_53050 Possible Proteases | Reprolysin |
| 16 | XP_001891567 | Bm1_00205 | ShTK domain containing protein |
| | | Protease Inhibitors | |
| 17 | XP_001893428.1 | Bm1_09775 Hypothetical Proteins | "serpin, putative" |
| 18 | XP_001901910 | Bm1_52210 | hypothetical protein |
| 19 | XP_001902925 | Bm1_57335 | "Conserved hypothetical protein, putative" |
| 20 | XP_001895546 | Bm1_20460 | hypothetical protein |
| 21 | XP_001900482 | Bm1_45100 | hypothetical protein |
| 22 | XP_001893045 | Bm1_07875 | CONSERVED HYPOTHETICAL PROTEIN |
| 23 | XP_001894967 | Bm1_17550 | hypothetical protein |
| 24 | XP_001893039 | Bm1_07845 | hypothetical protein |
| 25 | XP_001894908 | Bm1_17255 | hypothetical protein |
| 26 | XP_001895519 | Bm1_20325 | Hypothetical protein-conserved |
| 27 | XP_001900708 | Bm1_46230 | hypothetical protein |

TABLE A

BLAST-P OF INTESTINE ENRICHED NON-MITOCHONDRIAL PROTEINS WITH TRANSMEMBRANE DOMAINS AGAINST *W. BANCROFTI, O. VOLVULUS* AND *H. SAPIENS*

| B. malayi | | H. sapiens | | W. bancrofti | | O. volvulus | |
|---|---|---|---|---|---|---|---|
| Protein Type Gene Symbol/ Accession No./GI No. | Description | % Ident* | Query cov.** | % Ident* | Query Cov** | % Ident* | Query Cov** |
| | Acyltransferase | | | | | | |
| Bm1_43465/ XP_001900154.1/ GI: 170590790 | Temporarily assigned gene name protein 40, putative | xx | xx | 93 | 290-882 | 79 | 50-878 |
| | Carbohydrate Metabolism | | | | | | |
| Bm1_36055/ XP_001898658.1/ GI: 170587792 | hexokinase, putative | 47 | 16-437 | 65 | 22-438 | 82 | 1-439 |
| Bm1_52335/ XP_001901935.1/ GI: 170594367 | UDP-N-acetylglucosamine-dolichyl-phosphate N-acetylglucosaminephosphotransferase, putative | 49 | 2-404 | 94 | 1-406 | 89 | 1-406 |
| Catabolism | | | | | | | |
| Bm1_48180/ XP_001901098.1/ GI: 170592691 | Amidase family protein | 41 | 45-303 | 96 | 90-324 | 75 | 1-373 |

TABLE A-continued

BLAST-P OF INTESTINE ENRICHED NON-MITOCHONDRIAL PROTEINS WITH TRANSMEMBRANE DOMAINS AGAINST *W. BANCROFTI, O. VOLVULUS* AND *H. SAPIENS*

| B. malayi Protein Type Gene Symbol/ Accession No./GI No. | Description | H. sapiens % Ident* | H. sapiens Query cov.** | W. bancrofti % Ident* | W. bancrofti Query Cov** | O. volvulus % Ident* | O. volvulus Query Cov** |
|---|---|---|---|---|---|---|---|
| Cell Adhesion | | | | | | | |
| Bm1_39630/ XP_001899381.1/ GI:170589239 | Immunoglobulin I-set domain containing protein | 28 | 45-1170 | 97 | 628-1171 | 87 | 26-1171 |
| Bm1_02820/ XP_001892066.1/ GI:170572325 | EGF-like domain containing protein | 35 | 53-206 | 96 | 1-269 | 82 | 3-269 |
| Cell Signaling | | | | | | | |
| Bm1_30585/ XP_001897556.1/ GI: 170585572 | Tyrosine-protein kinase abl-1.-related | 24 | 212-281 | 95 | 10-281 | 79 | 10-281 |
| Bm1_19395/ XP_001895334.1/ GI:170580602 | Protein kinase domain containing protein | 34 | 15-1280 | 98 | 1-681 | 92 | 1-1280 |
| Bm1_38285/ XP_001899110.1/ GI: 170588697 | Ser/Thr protein phosphatase family protein | 40 | 22-287 | 95 | 9-293 | 79 | 2-293 |
| Bm1_51260/ XP_001901720.1/ GI: 170593937 | Innexin family protein | 29 | 327-399 | 83 | 1-523 | 64 | 1-533 |
| Bm1_31730/ XP_001897792.1/ GI:170586046 | phosphatidate cytidylyltransferase-related | 27 | 56-127 | 97 | 1-128 | 84 | 1-118 |
| Bm1_36290/ XP_001898705.1/ GI:170587887 | Putative phosphatidate cytidylyltransferase, putative | 50 | 41-480 | 94 | 1-374 | 85 | 5-487 |
| Bm1_43990/ XP_001900260.1/ GI:170591002 | Latrophilin receptor protein 2, putative | 42 | 354-715 | 81 | 59-873 | 68 | 32-873 |
| Bm1_05960/ XP_001892664.1/ GI:170574085 | Patched family protein | 20 | 229-896 | 96 | 66-549 | 73 | 1-933 |
| Bm1_23705/ XP_001896198.1/ GI:170582592 | protein C24B5.3, putative | 21 | 8-957 | 32 | 12-955 | 83 | 2-746 |
| Bm1_39815/ XP_001899418.1/ GI:170589313 | Ly-6-related protein HOT-2-related | 29 | 18-55 | 95 | 97-199 | 89 | 60-199 |
| Bm1_55745/ XP_001902606.1/ GI:170596018 | sulfakinin receptor protein, putative | 28 | 5-333 | 86 | 1-299 | 71 | 1-398 |
| Bm1_54240/ XP_001902307.1/ GI:170595251 | Endonuclease/Exonuclease/phosphatase family protein | 38 | 3-298 | 98 | 1-205 | 85 | 1-391 |
| Bm1_52975/ XP_001902063.1/ GI:170594623 | ER lumen protein retaining receptor, putative | 69 | 1-207 | 99 | 1-213 | 96 | 1-213 |
| Bm1_48590/ XP_001901181.1/ GI:170592857 | Low-density lipoprotein receptor domain class A containing protein | 47 | 4-46 | 91 | 1-154 | 66 | 1-154 |
| Cellular Trafficking | | | | | | | |
| Bm1_14235/ XP_001894314.1/ GI:170578208 | SNARE domain containing protein | 37 | 9-230 | 98 | 1-248 | 86 | 1-248 |
| Chaperone/HSP | | | | | | | |
| Bm1_15660/ XP_001894589.1/ GI:170578901 | DnaJ domain containing protein | 27 | 25-835 | 91 | 1-839 | 77 | 3-839 |
| Bm1_22450/ XP_001895946.1/ GI:170582031 | hemimethylated DNA binding domain containing protein | 25 | 34-112 | 97 | 29-119 | 95 | 29-119 |
| DNA/RNA Binding | | | | | | | |
| Bm1_41070/ XP_001899675.1/ GI:170589828 | Zinc finger DHHC domain containing protein 5, putative | 53 | 11-262 | 97 | 1-445 | 86 | 1-444 |

TABLE A-continued

BLAST-P OF INTESTINE ENRICHED NON-MITOCHONDRIAL PROTEINS WITH TRANSMEMBRANE DOMAINS AGAINST *W. BANCROFTI, O. VOLVULUS* AND *H. SAPIENS*

| B. malayi Protein Type Gene Symbol/ Accession No./GI No. | Description | H. sapiens % Ident* | H. sapiens Query cov.** | W. bancrofti % Ident* | W. bancrofti Query Cov** | O. volvulus % Ident* | O. volvulus Query Cov** |
|---|---|---|---|---|---|---|---|
| Glycosylation/glucuronidation | | | | | | | |
| Bm1_34610/ XP_001898369.1/ GI:170587206 | glycosyl transferase, group 2 family protein | 56 | 80-554 | 96 | 1-447 | 88 | 1-582 |
| Bm1_44655/ XP_001900394.1/ GI:170591272 | Fukutin.-related | 31 | 138-364 | 96 | 1-362 | 73 | 1-364 |
| Bm1_13480/ XP_001894161.1/ GI:170577851 | UDP-glucoronosyl and UDP-glucosyl transferase family protein | 27 | 35-509 | 95 | 1-425 | 29 | 214-293 |
| Immunological | | | | | | | |
| Bm1_50985/ XP_001901665.1/ GI:170593827 | Complement component C6 precursor.-related | 32 | 49-136 | 98 | 1-171 | 72 | 3-161 |
| Miscellaneous | | | | | | | |
| Bm1_15480/ XP_001894556.1/ GI:170578816 | Acyltransferase family protein | 28 | 295-352 | 94 | 44-351 | 80 | 17-649 |
| Bm1_23850/ XP_001896227.1/ GI:170582654 | cDNA sequence BC017158-related | 37 | 38-384 | 93 | 163-353 | 81 | 1-389 |
| Bm1_49590/ XP_001901384.1/ GI:170593263 | CG3054-PA-related | 28 | 97-260 | 81 | 1-242 | 69 | 1-260 |
| Bm1_15855/ XP_001894628.1/ GI:170578992 | D4Ertd196e protein, putative | 56 | 14-174 | 94 | 1-177 | 81 | 1-150 |
| Bm1_10500/ XP_001894628.1/ GI:170578992 | AMOP domain containing protein | 26 | 652-932 | 98 | 679-1377 | 92 | 1-1513 |
| Bm1_06760/ XP_001892822.1/ GI:170574457 | zgc: 100814 protein-related | 39 | 9-355 | 95 | 1-136 | 75 | 1-356 |
| Bm1_41280/ XP_001899713.1/ GI:170589904 | uncharacterized hypothalamus protein HTMP, putative | 56 | 50-295 | 96 | 1-296 | 82 | 4-296 |
| Bm1_17180/ XP_001894893.1/ GI:170579583 | MiaB-like tRNA modifying enzyme, archaeal-type family protein | 56 | 1-402 | 97 | 17-256 | 90 | 1-424 |
| Bm1_48010/ XP_001901064.1/ GI:170592623 | EGF-like domain containing protein | 36 | 10-395 | 91 | 19-338 | 66 | 6-560 |
| Proteases | | | | | | | |
| Bm1_18805/ XP_001895218.1/ GI:170580338 | Papain family cysteine protease containing protein | 34 | 65-309 | 68 | 73-267 | 52 | 35-309 |
| Bm1_38300/ XP_001899113.1/ GI:170588703 | Peptidase family M1 containing protein | 28 | 136-586 | 90 | 90-819 | 67 | 1-819 |
| Bm1_26370/ XP_001896728.1/ GI:170583765 | Rhomboid family protein | 36 | 77-347 | 96 | 1-377 | 83 | 1-377 |
| Bm1_11005/ XP_001896728.1/ GI:170583765 | MGC84665 protein-related | 38 | 2-98 | 95 | 1-96 | 80 | 1-98 |
| Bm1_53050/ XP_001902078.1/ GI:170594653 | Reprolysin | 32 | 153-753 | 91 | 96-845 | 77 | 1-839 |
| Possible Protease | | | | | | | |
| Bm1_00205/ XP_001891567.1/ GI:170571016 | ShTK domain containing protein | 27 | 54-161 | 80 | 142-229 | 52 | 70-227 |
| Protease inhibitor | | | | | | | |
| Bm1_09775/ XP_001893428.1/ GI:170575897 | serpin, putative | 29 | 26-388 | 75 | 84-375 | 52 | 29-390 |

TABLE A-continued

BLAST-P OF INTESTINE ENRICHED NON-MITOCHONDRIAL PROTEINS WITH TRANSMEMBRANE
DOMAINS AGAINST *W. BANCROFTI, O. VOLVULUS* AND *H. SAPIENS*

| B. malayi Protein Type Gene Symbol/ Accession No./GI No. | Description | H. sapiens % Ident* | H. sapiens Query cov.** | W. bancrofti % Ident* | W. bancrofti Query Cov** | O. volvulus % Ident* | O. volvulus Query Cov** |
|---|---|---|---|---|---|---|---|
| Sterol Metabolism | | | | | | | |
| Bm1_37660/ XP_001898982.1/ GI:170588441 | Oxysterol-binding protein | 45 | 37-747 | 93 | 312-748 | 87 | 57-724 |
| Structural | | | | | | | |
| Bm1_53475/ XP_001902163.1/ GI:170594883 | Nematode cuticle collagen N-terminal domain containing protein | 40 | 102-274 | 85 | 48-288 | 61 | 1-291 |
| Bm1_04695/ XP_001892417.1/ GI:170573305 | Cuticle collagen F09G8.6.-related | 40 | 80-251 | 96 | 43-270 | 89 | 1-266 |
| Bm1_19730/ XP_001895401.1/ GI:170580769 | Autophagy protein Apg9 containing protein | 43 | 50-655 | 91 | 204-814 | 82 | 1-814 |
| Transporters | | | | | | | |
| Bm1_08720/ XP_001893214.1/ GI:170575377 | ABC transporter N-terminus family protein | 46 | 65-153 | 94 | 1-150 | 78 | 1-153 |
| Bm1_06830/ XP_001892835.1/ GI:170574488 | ABC transporter transmembrane region family protein | 40 | 80-246 | 92 | 82-183 | 60 | 1-248 |
| Bm1_08185/ XP_001893108.1/ GI:170575121 | Cation transporter family protein | 37 | 35-439 | 96 | 1-444 | 84 | 3-444 |
| Bm1_34425/ XP_001898332.1/ GI:170587131 | Ctr copper transporter family protein | 28 | 63-255 | 89 | 1-276 | 69 | 10-276 |
| Bm1_00795/ XP_001891680.1/ GI:170571314 | E1-E2 ATPase family protein | 49 | 6-523 | 96 | 1-449 | 87 | 1-530 |
| Bm1_42365/ XP_001899937.1/ GI:170590354 | ZIP Zinc transporter family protein | 25 | 17-386 | 92 | 1-387 | 76 | 1-387 |
| Bm1_40010/ XP_001899457.1/ GI:170589391 | NRAMP-like transporter K11G12.4, putative | 59 | 44-457 | 100 | 228-457 | 85 | 34-457 |
| Bm1_38955/ XP_001899244.1/ GI:170588965 | Twik family of potassium channels protein 28, putative | 24 | 101-536 | 93 | 1-561 | 96 | 49-561 |
| Bm1_44770/ XP_001900417.1/ GI:170591318 | TWiK family of potassium channels protein 7, putative | 26 | 136-438 | 98 | 80-330 | 87 | 1-525 |
| Bm1_24840/ XP_001896428.1/ GI:170583097 | Major Facilitator Superfamily protein | 27 | 7-477 | 95 | 102-493 | 85 | 1-493 |
| Bm1_37140/ XP_001898875.1/ GI:170588227 | Major Facilitator Superfamily protein | 34 | 70-221 | 90 | 100-739 | 69 | 1-739 |
| Bm1_24985/ XP_001896457.1/ GI:170583158 | cation efflux family protein | 26 | 181-300 | 97 | 54-483 | 80 | 15-483 |
| Bm1_46360/ XP_001900734.1/ GI:170591953 | Transmembrane amino acid transporter protein | 27 | 29-447 | 97 | 32-443 | 93 | 1-401 |
| Bm1_25200/ XP_001896499.1/ GI:170583257 | Mitochondrial carrier C16C10.1, putative | 47 | 12-332 | 97 | 1-332 | 84 | 1-332 |
| Bm1_01695/ XP_001891855.1/ GI:170571765 | RE11181p-related | 28 | 14-258 | 89 | 1-360 | 22 | 1-258 |
| Bm1_42075/ XP_001899877.1/ GI:170590234 | zgc: 92765, putative | 49 | 11-351 | 81 | 1-397 | 80 | 1-396 |
| Bm1_43555/ XP_001900172.1/ GI:170590826 | ABC TRANSPORTER TRANSMEMBRANE REGION FAMILY PROTEIN | 40 | 19-1536 | 91 | 78-1087 | 71 | 549-1536 |
| Bm1_37475/ XP_001898945.1/ GI:170588367 | Major Facilitator Superfamily protein | 33 | 100-320 | 93 | 67-806 | 76 | 1-791 |

TABLE A-continued

BLAST-P OF INTESTINE ENRICHED NON-MITOCHONDRIAL PROTEINS WITH TRANSMEMBRANE
DOMAINS AGAINST *W. BANCROFTI, O. VOLVULUS* AND *H. SAPIENS*

| B. malayi Protein Type Gene Symbol/ Accession No./GI No. | Description | H. sapiens % Ident* | H. sapiens Query cov.** | W. bancrofti % Ident* | W. bancrofti Query Cov** | O. volvulus % Ident* | O. volvulus Query Cov** |
|---|---|---|---|---|---|---|---|
| Bm1_38360/ XP_001899125.1/ GI:170588727 | major facilitator superfamily protein | 30 | 41-553 | 98 | 31-565 | 92 | 31-564 |
| Bm1_15490/ XP_001894558.1/ GI:170578824 | ABC transporter family protein | 45 | 67-706 | 98 | 35-543 | 81 | 4-712 |
| Bm1_31305/ XP_001897706.1/ GI:170585872 | vesicular acetylcholine transporter unc-17, putative | 50 | 17-440 | 94 | 20-528 | 91 | 1-528 |
| Bm1_42930/ XP_001900048.1/ GI:170590576 | Excitatory amino acid transporter, putative | 59 | 7-469 | 98 | 1-320 | 92 | 245-498 |
| Bm1_02560/ XP_001892014.1/ GI:170572178 | Sodium/calcium exchanger protein | 35 | 29-341 | 86 | 156-342 | 78 | 1-342 |
| Bm1_31865/ XP_001897818.1/ GI:170586099 | Probable calcium-binding mitochondrial carrier F55A11.4, putative | 45 | 46-504 | 93 | 5-508 | 86 | 4-506 |
| | Hypothetical Proteins | | | | | | |
| Bm1_04935/ XP_001892465.1/ GI:170573424 | hypothetical protein | 47 | 4-37 | 28 | 1-54 | 65 | 1-68 |
| Bm1_33605/ XP_001898167.1/ GI:170586800 | hypothetical protein | 41 | 42-70 | 81 | 1-216 | 49 | 58-216 |
| Bm1_34095/ XP_001898267.1/ GI:170587000 | hypothetical protein | 29 | 15-88 | 42 | 55-87 | 68 | 1-131 |
| Bm1_22820/ XP_001896020.1/ GI:170582194/ | hypothetical protein | 35 | 30-69 | 100 | 1-68 | 94 | 1-81 |
| Bm1_26845/ XP_001896819.1/ GI:170584006 | Hypothetical protein | 33 | 77-164 | 92 | 1-162 | 79 | 58-245 |
| Bm1_45625/ XP_001900588.1/ GI:170591660 | hypothetical protein | 38 | 127-171 | 90 | 1-338 | 76 | 25-334 |
| Bm1_52210/ XP_001901910.1/ GI:170594317 | hypothetical protein | 29 | 238-350 | 97 | 53-433 | 85 | 1-431 |
| Bm1_02860 | hypothetical protein | xx | xx | 33 | 11-31 | 38 | 11-31 |
| Bm1_57335/ XP_001902925.1/ GI:170596866/ | Conserved hypothetical protein, putative | 31 | 114-236 | 96 | 1-246 | 89 | 1-246 |
| Bm1_25895/ XP_001896638.1/ GI:170583561 | hypothetical protein | 28 | 115-179 | 96 | 122-325 | 68 | 33-325 |
| Bm1_26820/ XP_001896814.1/ GI:170583994 | hypothetical protein | 38 | 318-378 | 88 | 1-317 | 59 | 1-191 |
| Bm1_46300/ XP_001900722.1/ GI:170591929 | hypothetical protein, conserved | 38 | 129-154 | 91 | 195-387 | 52 | 30-387 |
| Bm1_20460/ XP_001895546.1/ GI:170581122 | hypothetical protein | 30 | 103-147 | 24 | 94-147 | 82 | 1-191 |
| Bm1_27875/ XP_001897026.1/ GI:170584478 | hypothetical protein | 28 | 186-237 | 91 | 61-298 | 76 | 12-202 |
| Bm1_30935/ XP_001897629.1/ GI:170585718 | hypothetical protein | 39 | 37-67 | 82 | 4-90 | 27 | 30-89 |
| Bm1_53700/ XP_001902205.1/ GI:170594994 | hypothetical protein | 37 | 56-108 | 92 | 178-216 | 56 | 1-220 |
| Bm1_57235/ XP_001902905.1/ GI:170596815 | hypothetical protein | 40 | 39-81 | 50 | 45-62 | 65 | 1-67 |
| Bm1_45100/ XP_001900482.1/ GI:170591448 | hypothetical protein | 29 | 330-414 | 85 | 118-727 | 60 | 75-727 |

TABLE A-continued

BLAST-P OF INTESTINE ENRICHED NON-MITOCHONDRIAL PROTEINS WITH TRANSMEMBRANE DOMAINS AGAINST *W. BANCROFTI, O. VOLVULUS* AND *H. SAPIENS*

| B. malayi Protein Type Gene Symbol/ Accession No./GI No. | Description | H. sapiens % Ident* | H. sapiens Query cov.** | W. bancrofti % Ident* | W. bancrofti Query Cov** | O. volvulus % Ident* | O. volvulus Query Cov** |
|---|---|---|---|---|---|---|---|
| Bm1_07875/ XP_001893045.1/ GI:170574981 | CONSERVED HYPOTHETICAL PROTEIN | 31 | 84-225 | 99 | 142-231 | 85 | 53-231 |
| Bm1_30410/ XP_001897520.1/ GI:170585498 | conserved hypothetical protein | 38 | 152-201 | 99 | 112-234 | 89 | 105-234 |
| Bm1_17550/ XP_001894967.1/ GI:170579749 | hypothetical protein | 33 | 63-121 | 87 | 77-129 | 82 | 82-125 |
| Bm1_00920/ XP_001891702.1/ GI:170571368 | Hypothetical 30.5 kDa protein ZK1321.3 in chromosome II.-related | 25 | 5-168 | 93 | 1-176 | 72 | 1-176 |
| Bm1_04875/ XP_001892453.1/ GI:170573392 | hypothetical protein | xx | xx | xx | xx | xx | xx |
| Bm1_29435/ XP_001897329.1/ GI:170585108 | Hypothetical protein | 30 | 23-163 | 96 | 23-204 | 83 | 23-204 |
| Bm1_42465/ XP_001899956.1/ GI:170590392 | hypothetical protein | 28 | 85-134 | 84 | 1-394 | 70 | 1-394 |
| Bm1_48705/ XP_001901204.1/ GI:170592903 | conserved hypothetical protein | 23 | 57-267 | 97 | 96-267 | 74 | 1-268 |
| Bm1_32415/ XP_001897928.1/ GI:170586322 | Hypothetical 21.5 kDa protein in SEC15-SAP4 intergenic region.-related | 52 | 25-168 | 93 | 1-176 | 90 | 1-176 |
| Bm1_07845/ XP_001893039.1/ GI:170574965 | hypothetical protein | 28 | 24-108 | 89 | 1-210 | 64 | 1-210 |
| Bm1_15300/ XP_001894520.1/ GI:170578730 | Hypothetical protein | xx | xx | xx | xx | xx | xx |
| Bm1_17255/ XP_001894908.1/ GI:170579615 | hypothetical protein | 21 | 93-246 | 87 | 17-251 | 78 | 28-251 |
| Bm1_18965/ XP_001895250.1/ GI:170580404 | Hypothetical protein | 45 | 46-235 | 91 | 1-206 | 78 | 1-236 |
| Bm1_20325/ XP_001895519.1/ GI:170581054 | Hypothetical protein-conserved | 37 | 2-215 | 96 | 1-487 | 89 | 1-487 |
| Bm1_44010/ XP_001900264.1/ GI:170591010 | hypothetical protein | 42 | 3-33 | 92 | 91-185 | 26 | 74-156 |
| Bm1_46230/ XP_001900708.1/ GI:170591901 | hypothetical protein | 29 | 184-256 | 91 | 24-278 | 62 | 1-278 |

*"% Ident" is the percentage of amino acids within the query coverage identical to query sequence.
**"Query cov." span of amino acids in the query sequence that aligns with the target sequence producing significant alignment

TABLE B

BLAST P OF THE TABLE A INTESTINE PROTEINS AGAINST *L. LOA* AND *D. IMMITIS*.

| B. malayi Protein Type Gene Symbol/ Accession No./GI No. | Description | L. loa % Ident* | L. loa Query Cov** | D. immitis % Ident* | D. immitis Query Cov** |
|---|---|---|---|---|---|
| Acyltransferase | | | | | |
| Bm1_43465/ XP_001900154.1/ GI: 170590790 | Temporarily assigned gene name protein 40, putative | 88 | 50-664 | 84 | 64-882 |

TABLE B-continued

BLAST P OF THE TABLE A INTESTINE PROTEINS AGAINST *L. LOA* AND *D. IMMITIS*.

*B. malayi*
Protein Type
Gene Symbol/
Accession No./GI No.

| B. malayi Protein Type Gene Symbol/ Accession No./GI No. | Description | L. loa % Ident* | L. loa Query Cov** | D. immitis % Ident* | D. immitis Query Cov** |
|---|---|---|---|---|---|
| Carbohydrate Metabolism | | | | | |
| Bm1_36055/ XP_001898658.1/ GI: 170587792 | hexokinase, putative | 63 | 22-438 | 84 | 1-439 |
| Bm1_52335/ XP_001901935.1/ GI: 170594367 | UDP-N-acetylglucosamine-dolichyl-phosphate N-acetylglucosaminephosphotransferase, putative | 91 | 1-406 | 87 | 1-388 |
| Catabolism | | | | | |
| Bm1_48180/ XP_001901098.1/ GI: 170592691 | Amidase family protein | 78 | 1-373 | 74 | 90-373 |
| Cell Adhesion | | | | | |
| Bm1_39630/ XP_001899381.1/ GI: 170589239 | Immunoglobulin I-set domain containing protein | 89 | 1-1171 | 82 | 1-1171 |
| Bm1_02820/ XP_001892066.1/ GI: 170572325 | EGF-like domain containing protein | 89 | 62-269 | 79 | 2-269 |
| Cell Signaling | | | | | |
| Bm1_30585/ XP_001897556.1/ GI: 170585572 | Tyrosine-protein kinase abl-1.-related | 83 | 10-281 | 84 | 10-281 |
| Bm1_19395/ XP_001895334.1/ GI: 170580602 | Protein kinase domain containing protein | 95 | 1-1280 | 93 | 1-1280 |
| Bm1_38285/ XP_001899110.1/ GI: 170588697 | Ser/Thr protein phosphatase family protein | 88 | 9-293 | 79 | 1-290 |
| Bm1_51260/ XP_001901720.1/ GI: 170593937 | Innexin family protein | 69 | 1-523 | 64 | 1-532 |
| Bm1_31730/ XP_001897792.1/ GI: 170586046 | phosphatidate cytidylyltransferase-related | 93 | 1-125 | 87 | 1-125 |
| Bm1_36290/ XP_001898705.1/ GI: 170587887 | Putative phosphatidate cytidylyltransferase, putative | 89 | 5-487 | 78 | 1-487 |
| Bm1_43990/ XP_001900260.1/ GI: 170591002 | Latrophilin receptor protein 2, putative | 76 | 19-841 | 69 | 27-873 |
| Bm1_05960/ XP_001892664.1/ GI: 170574085 | Patched family protein | 87 | 1-934 | 75 | 1-933 |
| Bm1_23705/ XP_001896198.1/ GI: 170582592 | protein C24B5.3, putative | 90 | 1-934 | 93 | 648-959 |
| Bm1_39815/ XP_001899418.1/ GI: 170589313 | Ly-6-related protein HOT-2-related | 89 | 69-199 | 89 | 6-189 |
| Bm1_55745/ XP_001902606.1/ GI: 170596018 | sulfakinin receptor protein, putative | 36 | 4-333 | 64 | 139-392 |
| Bm1_54240/ XP_001902307.1/ GI: 170595251 | Endonuclease/Exonuclease/phosphatase family protein | 88 | 1-256 | 83 | 1-391 |
| Bm1_52975/ XP_001902063.1/ GI: 170594623 | ER lumen protein retaining receptor, putative | 96 | 1-213 | 96 | 1-209 |
| Bm1_48590/ XP_001901181.1/ GI: 170592857 | Low-density lipoprotein receptor domain class A containing protein | 74 | 4-154 | 67 | 9-154 |

TABLE B-continued

BLAST P OF THE TABLE A INTESTINE PROTEINS AGAINST *L. LOA* AND *D. IMMITIS*.

| B. malayi Protein Type Gene Symbol/ Accession No./GI No. | Description | *L. loa* % Ident* | *L. loa* Query Cov** | *D. immitis* % Ident* | *D. immitis* Query Cov** |
|---|---|---|---|---|---|
| Cellular Trafficking | | | | | |
| Bm1_14235/ XP_001894314.1/ GI: 170578208 | SNARE domain containing protein | 94 | 1-248 | 83 | 1-235 |
| Chaperone/HSP | | | | | |
| Bm1_15660/ XP_001894589.1/ GI: 170578901 | DnaJ domain containing protein | 85 | 11-839 | 80 | 1-839 |
| Bm1_22450/ XP_001895946.1/ GI: 170582031 | hemimethylated DNA binding domain containing protein | 97 | 29-119 | 91 | 28-119 |
| DNA/RNA Binding | | | | | |
| Bm1_41070/ XP_001899675.1/ GI: 170589828 | Zinc finger DHHC domain containing protein 5, putative | 90 | 28-445 | 88 | 1-445 |
| Glycosylation/ glucuronidation | | | | | |
| Bm1_34610/ XP_001898369.1/ GI: 170587206 | glycosyl transferase, group 2 family protein | 89 | 1-435 | 88 | 1-582 |
| Bm1_44655/ XP_001900394.1/ GI: 170591272 | Fukutin.-related | 85 | 1-364 | 75 | 1-364 |
| Bm1_13480/ XP_001894161.1/ GI: 170577851 | UDP-glucoronosyl and UDP-glucosyl transferase family protein | 81 | 1-423 | 72 | 155-502 |
| Immunological | | | | | |
| Bm1_50985/ XP_001901665.1/ GI: 170593827 | Complement component C6 precursor.-related | 61 | 2-166 | 75 | 3-171 |
| Miscellaneous | | | | | |
| Bm1_15480/ XP_001894556.1/ GI: 170578816 | Acyltransferase family protein | 86 | 266-467 | 76 | 49-638 |
| Bm1_23850/ XP_001896227.1/ GI: 170582654 | cDNA sequence BC017158-related | 82 | 1-389 | 72 | 21-389 |
| Bm1_49590/ XP_001901384.1/ GI: 170593263 | CG3054-PA-related | 63 | 1-262 | 67 | 1-254 |
| Bm1_15855/ XP_001894628.1/ GI: 170578992 | D4Ertd196e protein, putative | 86 | 1-177 | 81 | 1-151 |
| Bm1_10500/ XP_001894628.1/ GI: 170578992 | AMOP domain containing protein | 94 | 1-1513 | 90 | 609-1513 |
| Bm1_06760/ XP_001892822.1/ GI: 170574457 | zgc: 100814 protein-related | 84 | 1-357 | 71 | 1-356 |
| Bm1_41280/ XP_001899713.1/ GI: 170589904 | uncharacterized hypothalamus protein HTMP, putative | 81 | 1-296 | 80 | 1-296 |
| Bm1_17180/ XP_001894893.1/ GI: 170579583 | MiaB-like tRNA modifying enzyme, archaeal-type family protein | 94 | 1-390 | 95 | 1-265 |
| Bm1_48010/ XP_001901064.1/ GI: 170592623 | EGF-like domain containing protein | 74 | 6-556 | 64 | 6-546 |
| Proteases | | | | | |
| Bm1_18805/ XP_001895218.1/ GI: 170580338 | Papain family cysteine protease containing protein | 56 | 134-313 | 41 | 1-314 |

TABLE B-continued

BLAST P OF THE TABLE A INTESTINE PROTEINS AGAINST *L. LOA* AND *D. IMMITIS*.

| B. malayi Protein Type Gene Symbol/ Accession No./GI No. | Description | *L. loa* % Ident* | Query Cov** | *D. immitis* % Ident* | Query Cov** |
|---|---|---|---|---|---|
| Bm1_38300/ XP_001899113.1/ GI: 170588703 | Peptidase family M1 containing protein | 74 | 1-819 | 70 | 1-819 |
| Bm1_26370/ XP_001896728.1/ GI: 170583765 | Rhomboid family protein | 83 | 1-377 | 85 | 17-377 |
| Bm1_11005/ XP_001896728.1/ GI: 170583765 | MGC84665 protein-related | 91 | 1-98 | 90 | 1-40 |
| Bm1_53050/ XP_001902078.1/ GI: 170594653 Possible Protease | Reprolysin | 79 | 1-839 | 77 | 1-843 |
| Bm1_00205/ XP_001891567.1/ GI: 170571016 Protease inhibitor | ShTK domain containing protein | 46 | 126-264 | 55 | 110-264 |
| Bm1_09775/ XP_001893428.1/ GI: 170575897 | serpin, putative | 54 | 1-391 | 52 | 1-391 |

| Sterol Metabolism | Sterol Metabolism | | | | |
|---|---|---|---|---|---|
| Bm1_37660/ XP_001898982.1/ GI: 170588441 | Oxysterol-binding protein | 82 | 57-753 | 86 | 57-753 |

| Structural | Structural | | | | |
|---|---|---|---|---|---|
| BBm1_53475/ XP_001902163.1/ GI: 170594883 | Nematode cuticle collagen N-terminal domain containing protein | 64 | 1-281 | 55 | 46-291 |
| Bm1_04695/ XP_001892417.1/ GI: 170573305 | Cuticle collagen F09G8.6.-related | 89 | 1-270 | 86 | 1-269 |
| Bm1_19730/ XP_001895401.1/ GI: 170580769 Transporters | Autophagy protein Apg9 containing protein | 86 | 1-814 | 81 | 1-814 |
| Bm1_08720/ XP_001893214.1/ GI: 170575377 | ABC transporter N-terminus family protein | 84 | 1-153 | 72 | 1-153 |
| Bm1_06830/ XP_001892835.1/ GI: 170574488 | ABC transporter transmembrane region family protein | 81 | 82-248 | 62 | 1-244 |
| Bm1_08185/ XP_001893108.1/ GI: 170575121 | Cation transporter family protein | 57 | 32-345 | 59 | 67-345 |
| Bm1_34425/ XP_001898332.1/ GI: 170587131 | Ctr copper transporter family protein | 74 | 2-276 | 73 | 1-276 |
| Bm1_00795/ XP_001891680.1/ GI: 170571314 | E1-E2 ATPase family protein | 91 | 45-531 | 85 | 1-529 |
| Bm1_42365/ XP_001899937.1/ GI: 170590354 | ZIP Zinc transporter family protein | 81 | 28-387 | 43 | 17-386 |
| Bm1_40010/ XP_001899457.1/ GI: 170589391 | NRAMP-like transporter K11G12.4, putative | 91 | 1-456 | 83 | 1-457 |
| Bm1_38955/ XP_001899244.1/ GI: 170588965 | Twik family of potassium channels protein 28, putative | 92 | 1-561 | 91 | 1-561 |
| Bm1_44770/ XP_001900417.1/ GI: 170591318 | TWiK family of potassium channels protein 7, putative | 94 | 1-525 | 91 | 1-525 |

TABLE B-continued

BLAST P OF THE TABLE A INTESTINE PROTEINS AGAINST *L. LOA* AND *D. IMMITIS*.

*B. malayi*
Protein Type
Gene Symbol/

| Accession No./GI No. | Description | L. loa | | D. immitis | |
|---|---|---|---|---|---|
| | | % Ident* | Query Cov** | % Ident* | Query Cov** |
| Bm1_24840/ XP_001896428.1/ GI: 170583097 | Major Facilitator Superfamily protein | 87 | 1-418 | 86 | 1-493 |
| Bm1_37140/ XP_001898875.1/ GI: 170588227 | Major Facilitator Superfamily protein | 75 | 1-738 | 71 | 1-739 |
| Bm1_24985/ XP_001896457.1/ GI: 170583158 | cation efflux family protein | 85 | 1-483 | 81 | 1-483 |
| Bm1_46360/ XP_001900734.1/ GI: 170591953 | Transmembrane amino acid transporter protein | 86 | 1-443 | 91 | 1-439 |
| Bm1_25200/ XP_001896499.1/ GI: 170583257 | Mitochondrial carrier C16C10.1, putative | 89 | 1-332 | 83 | 1-332 |
| Bm1_01695/ XP_001891855.1/ GI: 170571765 | RE11181p-related | 26 | 4-105 | 23 | 4-258 |
| Bm1_42075/ XP_001899877.1/ GI: 170590234 | zgc: 92765, putative | 84 | 1-396 | 74 | 1-396 |
| Bm1_43555/ XP_001900172.1/ GI: 170590826 | ABC TRANSPORTER TRANSMEMBRANE REGION FAMILY PROTEIN | 71 | 12-996 | 71 | 14-1423 |
| Bm1_37475/ XP_001898945.1/ GI: 170588367 | Major Facilitator Superfamily protein | 82 | 1-792 | 78 | 113-795 |
| Bm1_38360/ XP_001899125.1/ GI: 170588727 | major facilitator superfamily protein | 93 | 31-565 | 91 | 21-564 |
| Bm1_15490/ XP_001894558.1/ GI: 170578824 | ABC transporter family protein | 89 | 4-713 | 77 | 7-638 |
| Bm1_31305/ XP_001897706.1/ GI: 170585872 | vesicular acetylcholine transporter unc-17, putative | 92 | 1-528 | 87 | 1-528 |
| Bm1_42930/ XP_001900048.1/ GI: 170590576 | Excitatory amino acid transporter, putative | 92 | 1-498 | 93 | 1-499 |
| Bm1_02560/ XP_001892014.1/ GI: 170572178 | Sodium/calcium exchanger protein | 79 | 1-342 | 71 | 1-314 |
| Bm1_31865/ XP_001897818.1/ GI: 170586099 | Probable calcium-binding mitochondrial carrier F55A11.4, putative | 82 | 8-501 | 86 | 4-508 |

Hypothetical Proteins

| Bm1_04935/ XP_001892465.1/ GI: 170573424 | hypothetical protein | 72 | 1-111 | 66 | 1-112 |
|---|---|---|---|---|---|
| Bm1_33605/ XP_001898167.1/ GI: 170586800 | hypothetical protein | 58 | 111-216 | 22 | 19-188 |
| Bm1_34095/ XP_001898267.1/ GI: 170587000 | hypothetical protein | 81 | 1-131 | 71 | 1-129 |
| Bm1_22820/ XP_001896020.1/ GI: 170582194/ | hypothetical protein | 98 | 1-81 | 96 | 1-81 |
| Bm1_26845/ XP_001896819.1/ GI: 170584006 | Hypothetical protein | 81 | 63-162 | 72 | 1-245 |
| Bm1_45625/ XP_001900588.1/ GI: 170591660 | hypothetical protein | 82 | 1-332 | 76 | 1-332 |
| Bm1_52210/ XP_001901910.1/ GI: 170594317 | hypothetical protein | 87 | 15-432 | 84 | 1-430 |

TABLE B-continued

BLAST P OF THE TABLE A INTESTINE PROTEINS AGAINST *L. LOA* AND *D. IMMITIS*.

| B. malayi Protein Type Gene Symbol/ Accession No./GI No. | Description | *L. loa* % Ident* | *L. loa* Query Cov** | *D. immitis* % Ident* | *D. immitis* Query Cov** |
|---|---|---|---|---|---|
| Bm1_02860 | hypothetical protein | 33 | 11-31 | 33 | 11-31 |
| Bm1_57335/ XP_001902925.1/ GI: 170596866/ | Conserved hypothetical protein, putative | 91 | 1-246 | 87 | 1-246 |
| Bm1_25895/ XP_001896638.1/ GI: 170583561 | hypothetical protein | 74 | 31-325 | 67 | 24-325 |
| Bm1_26820/ XP_001896814.1/ GI: 170583994 | hypothetical protein | 77 | 1-317 | 72 | 99-317 |
| Bm1_46300/ XP_001900722.1/ GI: 170591929 | hypothetical protein, conserved | 75 | 1-191 | 56 | 18-380 |
| Bm1_20460/ XP_001895546.1/ GI: 170581122 | hypothetical protein | 86 | 1-191 | 85 | 1-191 |
| Bm1_27875/ XP_001897026.1/ GI: 170584478 | hypothetical protein | 79 | 12-202 | 77 | 185-298 |
| Bm1_30935/ XP_001897629.1/ GI: 170585718 | hypothetical protein | 64 | 9-90 | 28 | 17-70 |
| Bm1_53700/ XP_001902205.1/ GI: 170594994 | hypothetical protein | 57 | 53-236 | 62 | 2-103 |
| Bm1_57235/ XP_001902905.1/ GI: 170596815 | hypothetical protein | 85 | 10-67 | 74 | 1-68 |
| Bm1_45100/ XP_001900482.1/ GI: 170591448 | hypothetical protein | 67 | 81-696 | 49 | 271-727 |
| Bm1_07875/ XP_001893045.1/ GI: 170574981 | CONSERVED HYPOTHETICAL PROTEIN | 90 | 42-231 | 90 | 41-231 |
| Bm1_30410/ XP_001897520.1/ GI: 170585498 | conserved hypothetical protein | 90 | 1-234 | 94 | 154-234 |
| Bm1_17550/ XP_001894967.1/ GI: 170579749 | hypothetical protein | 77 | 77-129 | 86 | 82-125 |
| Bm1_00920/ XP_001891702.1/ GI: 170571368 | Hypothetical 30.5 kDa protein ZK1321.3 in chromosome II.-related | 75 | 1-174 | 75 | 1-176 |
| Bm1_04875/ XP_001892453.1/ GI: 170573392 | hypothetical protein | xx | xx | xx | xx |
| Bm1_29435/ XP_001897329.1/ GI: 170585108 | Hypothetical protein | 89 | 23-204 | 81 | 23-204 |
| Bm1_42465/ XP_001899956.1/ GI: 170590392 | hypothetical protein | 25 | 14-387 | 25 | 14-385 |
| Bm1_48705/ XP_001901204.1/ GI: 170592903 | conserved hypothetical protein | 81 | 1-268 | 72 | 1-269 |
| Bm1_32415/ XP_001897928.1/ GI: 170586322 | Hypothetical 21.5 kDa protein in SEC15-SAP4 intergenic region.-related | 93 | 1-176 | 91 | 1-176 |
| Bm1_07845/ XP_001893039.1/ GI: 170574965 | hypothetical protein | 75 | 1-210 | 72 | 60-210 |
| Bm1_15300/ XP_001894520.1/ GI: 170578730 | Hypothetical protein | xx | xx | xx | xx |
| Bm1_17255/ XP_001894908.1/ GI: 170579615 | hypothetical protein | 73 | 13-251 | 75 | 28-251 |
| Bm1_18965/ XP_001895250.1/ GI: 170580404 | Hypothetical protein | 85 | 1-236 | 77 | 1-239 |

TABLE B-continued

BLAST P OF THE TABLE A INTESTINE PROTEINS AGAINST *L. LOA* AND *D. IMMITIS*.

| B. malayi Protein Type Gene Symbol/ Accession No./GI No. | Description | *L. loa* % Ident* | *L. loa* Query Cov** | *D. immitis* % Ident* | *D. immitis* Query Cov** |
|---|---|---|---|---|---|
| Bm1_20325/ XP_001895519.1/ GI: 170581054 | Hypothetical protein-conserved | 91 | 1-487 | 89 | 1-485 |
| Bm1_44010/ XP_001900264.1/ GI: 170591010 | hypothetical protein | 72 | 9-185 | 32 | 61-129 |
| Bm1_46230/ XP_001900708.1/ GI: 170591901 | hypothetical protein | 65 | 18-278 | 31 | 161-281 |

*"% Ident" is the percentage of amino acids within the query coverage identical to query sequence.
**"Query cov." span of amino acids in the query sequence that aligns with the target sequence producing significant alignment

TABLE C

SELECTED PROTEINS FROM TABLES A AND B CONTAINING 1-2 TRANSMEMBRANE DOMAINS, A SIGNIFICANT NON-CYTOPLASMIC PORTION, >75% HOMOLOGY TO EITHER *W. BANCROFTI* OR *O. VOLVULUS* AND <40% HOMOLOGY TO HUMANS.

| SEQ ID NO:/ Gene Symbol | *H. sapiens* % Ident* | *H. sapiens* Query cov**. | *W. bancrofti* % Ident* | *W. bancrofti* Query Cov** | *O. volvulus* % Ident* | *O. volvulus* Query Cov** | *L. loa* % Ident* | *L. loa* Query Cov** | *D. immitis* % Ident* | *D. immitis* Query Cov** |
|---|---|---|---|---|---|---|---|---|---|---|
| 1/Bm1_39630/ XP_001899381.1/ GI:170589239 | 28 | 45-1170 | 97 | 628-1171 | 87 | 26-1171 | 89 | 1-1171 | 82 | 1-1171 |
| 2/Bm1_02820/ XP_001892066.1/ GI:170572325 | 35 | 53-206 | 96 | 1-269 | 82 | 3-269 | 89 | 62-269 | 79 | 2-269 |
| 3/Bm1_30585/ XP_001897556.1/ GI:170585572 | 24 | 212-281 | 95 | 10-281 | 79 | 10-281 | 83 | 10-281 | 84 | 10-281 |
| 4/Bm1_19395/ XP_001895334.1/ GI:170580602 | 34 | 15-1280 | 98 | 1-681 | 92 | 1-1280 | 95 | 1-1280 | 93 | 1-1280 |
| 5/Bm1_38285/ XP_001899110.1/ GI:170588697 | 40 | 22-287 | 95 | 9-293 | 79 | 2-293 | 88 | 9-293 | 79 | 1-290 |
| 6/Bm1_15660/ XP_001894589.1/ GI:170578901 | 27 | 25-835 | 91 | 1-839 | 77 | 3-839 | 85 | 11-839 | 80 | 1-839 |
| 7/Bm1_22450/ XP_001895946.1/ GI:170582031 | 25 | 34-112 | 97 | 29-119 | 95 | 29-119 | 97 | 29-119 | 91 | 28-119 |
| 8/Bm1_44655/ XP_001900394.1/ GI:170591272 | 31 | 138-364 | 96 | 1-362 | 73 | 1-364 | 85 | 1-364 | 75 | 1-364 |
| 9/Bm1_13480/ XP_001894161.1/ GI:170577851 | 27 | 35-509 | 95 | 1-425 | 29 | 214-293 | 81 | 1-423 | 72 | 155-502 |
| 10/Bm1_49590/ XP_001901384.1/ GI:170593263 | 28 | 97-260 | 81 | 1-242 | 69 | 1-260 | 63 | 1-262 | 67 | 1-254 |
| 11/Bm1_10500/ XP_001893572.1/ GI:170576299 | 26 | 652-932 | 98 | 679-1377 | 92 | 1-1513 | 94 | 1-1513 | 90 | 609-1513 |
| 12/Bm1_48010/ XP_001901064.1 GI:170592623/ | 36 | 10-395 | 91 | 19-338 | 66 | 6-560 | 74 | 6-556 | 64 | 6-546 |
| 13/Bm1_38300/ XP_001899113.1/ GI:170588703 | 28 | 136-586 | 90 | 90-819 | 67 | 1-819 | 74 | 1-819 | 70 | 1-819 |
| 14/Bm1_11005/ XP_001893672.1/ GI:170576544 | 38 | 2-98 | 95 | 1-96 | 80 | 1-98 | 91 | 1-98 | 90 | 1-40 |
| 15/Bm1_53050/ XP_001902078.1/ GI:170594653 | 32 | 153-753 | 91 | 96-845 | 77 | 1-839 | 79 | 1-839 | 77 | 1-843 |

TABLE C-continued

SELECTED PROTEINS FROM TABLES A AND B CONTAINING 1-2 TRANSMEMBRANE DOMAINS, A SIGNIFICANT NON-CYTOPLASMIC PORTION, >75% HOMOLOGY TO EITHER *W. BANCROFTI* OR *O. VOLVULUS* AND <40% HOMOLOGY TO HUMANS.

| | H. sapiens | | W. bancrofti | | O. volvulus | | L. loa | | D. immitis | |
|---|---|---|---|---|---|---|---|---|---|---|
| SEQ ID NO:/ Gene Symbol | % Ident* | Query cov**. | % Ident* | Query Cov** | % Ident* | Query Cov** | % Ident* | Query Cov** | % Ident* | Query Cov** |
| 16/Bm1_00205/ XP_001891567.1/ GI:170571016 | 27 | 54-161 | 80 | 142-229 | 52 | 70-227 | 46 | 126-264 | 55 | 110-264 |
| 17/Bm1_09775/ XP_001893428.1/ GI:170575897 | 29 | 26-388 | 75 | 84-375 | 52 | 29-390 | 54 | 1-391 | 52 | 1-391 |
| 18/Bm1_52210/ XP_001901910.1/ GI:170594317 | 29 | 238-350 | 97 | 53-433 | 85 | 1-431 | 87 | 15-432 | 84 | 1-430 |
| 19/Bm1_57335/ XP_001902925.1/ GI:170596866 | 31 | 114-236 | 96 | 1-246 | 89 | 1-246 | 91 | 1-246 | 87 | 1-246 |
| 20/Bm1_20460/ XP_001895546.1/ GI:170581122 | 30 | 103-147 | 24 | 94-147 | 82 | 1-191 | 86 | 1-191 | 85 | 1-191 |
| 21/Bm1_45100/ XP_001900482.1/ GI:170591448 | 29 | 330-414 | 85 | 118-727 | 60 | 75-727 | 67 | 81-696 | 49 | 271-727 |
| 22/Bm1_07875/ XP_001893045.1/ GI:170574981 | 31 | 84-225 | 99 | 142-231 | 85 | 53-231 | 90 | 42-231 | 90 | 41-231 |
| 23/Bm1_17550/ XP_001894967.1/ GI:170579749 | 33 | 63-121 | 87 | 77-129 | 82 | 82-125 | 77 | 77-129 | 86 | 82-125 |
| 24/Bm1_07845/ XP_001893039.1/ GI:170574965 | 28 | 24-108 | 89 | 1-210 | 64 | 1-210 | 75 | 1-210 | 72 | 60-210 |
| 25/Bm1_17255/ XP_001894908.1/ GI:170579615 | 21 | 93-246 | 87 | 17-251 | 78 | 28-251 | 73 | 13-251 | 75 | 28-251 |
| 26/Bm1_20325/ XP_001895519.1/ GI:170581054 | 37 | 2-215 | 96 | 1-487 | 89 | 1-487 | 91 | 1-487 | 89 | 1-485 |
| 27/Bm1_46230/ XP_001900708.1/ GI:170591901 | 29 | 184-256 | 91 | 24-278 | 62 | 1-278 | 65 | 18-278 | 31 | 161-281 |

*"% Ident" is the percentage of amino acids within the query coverage identical to query sequence.
**"Query cov." span of amino acids in the query sequence that aligns with the target sequence producing significant alignment

TABLE D

NORMALIZED SPECTRAL ABUNDANCE FACTOR (NSAF) AND NSAF ENRICHMENT

| | NSAF enrichment* | | | NSAF | | |
|---|---|---|---|---|---|---|
| SEQ ID NO. | Intestine | Body Wall | Reproductive Tract | Abundance** Intestine | Non-cytoplasmic domain$^a$ | Transmembrane (TMHMM)$^b$ |
| 1/Bm1_39630/ XP_001899381.1/ GI:170589239 | 3.84 | 0.26 | 0 | 2.20E-05 | 19-1120 | 1 |
| 2/Bm1_02820/ XP_001892066.1/ GI:170572325 | 9999 | 0 | 0 | 1.30E-04 | 1-225 | 1 |
| 3/Bm1_30585/ XP_001897556.1/ GI:170585572 | 4.42 | 0 | 0.23 | 8.40E-05 | 19-135 | 1 |
| 4/Bm1_19395/ XP_001895334.1/ GI:170580602 | 3.42 | 0.14 | 0.12 | 3.30E-05 | 1-942 | 1 |
| 5/Bm1_38285/ XP_001899110.1/ GI:170588697 | 7.68 | 0.13 | 0 | 1.80E-04 | 41-293 | 1 |
| 6/Bm1_15660/ XP_001894589.1/ GI:170578901 | 10.31 | 0 | 0.1 | 7.20E-05 | 18-220 | 1 |
| 7/Bm1_22450/ XP_001895946.1/ GI:170582031 | 2.74 | 0.17 | 0.14 | 2.70E-04 | 1-125 | 1 |

TABLE D-continued

NORMALIZED SPECTRAL ABUNDANCE FACTOR (NSAF) AND NSAF ENRICHMENT

| SEQ ID NO. | NSAF enrichment* | | | NSAF Abundance** Intestine | Non-cytoplasmic domain$^a$ | Transmembrane (TMHMM)$^b$ |
| --- | --- | --- | --- | --- | --- | --- |
| | Intestine | Body Wall | Reproductive Tract | | | |
| 8/Bm1_44655/ XP_001900394.1/ GI:170591272 | 2.95 | 0 | 0.34 | 4.70E-05 | 28-364 | 1 |
| 9/Bm1_13480/ XP_001894161.1/ GI:170577851 | 28.16 | 0.04 | 0 | 7.40E-04 | 1-486 | 1 |
| 10/Bm1_49590/ XP_001901384.1/ GI:170593263 | 2.95 | 0 | 0.34 | 6.50E-05 | 1-51, 101-265 | 2 |
| 11/Bm1_10500/ XP_001893572.1/ GI:170576299/ | 5.99 | 0.01 | 0.15 | 6.10E-04 | 23-1322 | 1 |
| 12/Bm1_48010/ XP_001901064.1 GI:170592623/ | 2.03 | 0.38 | 0.06 | 2.50E-04 | 1-430 | 1 |
| 13/Bm1_38300/ XP_001899113.1/ GI:170588703 | 9999 | 0 | 0 | 1.60E-05 | 81-1061 | 1 |
| 14/Bm1_11005/ XP_001893672.1/ GI:170576544 | 2.74 | 0.17 | 0.14 | 2.00E-04 | 1-16, 76-169 | 1 |
| 15/Bm1_53050/ XP_001902078.1/ GI:170594653 | 2.95 | 0 | 0.34 | 6.10E-04 | 1-607 | 1 |
| 16/Bm1_00205/ XP_001891567.1/ GI:170571016 | 3.42 | 0.23 | 0.04 | 4.200+00 | 26-264 | 1 |
| 17/Bm1_09775/ XP_001893428.1/ GI:170575897 | 2.56 | 0.39 | 0 | 4.70E-05 | 17-391 | 1 |
| 18/Bm1_52210/ XP_001901910.1/ GI:170594317 | 9999 | 0 | 0 | 4.00E-05 | 1-369 | 1 |
| 19/Bm1_57335/ XP_001902925.1/ GI:170596866 | 9999 | 0 | 0 | 7.00E-05 | 29-211 | 2 |
| 20/Bm1_20460/ XP_001895546.1/ GI:170581122 | 2.95 | 0 | 0.34 | 8.00E-05 | 143-147 | 2 |
| 21/Bm1_45100/ XP_001900482.1/ GI:170591448 | 5.12 | 0.2 | 0 | 4.70E-05 | 285-727 | 1 |
| 22/Bm1_07875/ XP_001893045.1/ GI:170574981 | 4.42 | 0 | 0.23 | 1.10E-04 | 1-56. | 1 |
| 23/Bm1_17550/ XP_001894967.1/ GI:170579749 | 2.56 | 0.39 | 0 | 1.30E-04 | 1-61. | 1 |
| 24/Bm1_07845/ XP_001893039.1/ GI:170574965 | 2.09 | 0.15 | 0.24 | 4.90E-04 | 53-210 | 1 |
| 25/Bm1_17255/ XP_001894908.1/ GI:170579615 | 3.64 | 0.2 | 0.05 | 3.80E-04 | 36-251 | 1 |
| 26/Bm1_20325/ XP_001895519.1/ GI:170581054 | 3.36 | 0.12 | 0.14 | 3.00E-04 | 1-194 | 1 |
| 27/Bm1_46230/ XP_001900708.1/ GI:170591901 | 2.21 | 0 | 0.45 | 1.80E-04 | 121-289 | 1 |

*Calculated as described in the Examples
**Calculated as described in the Examples
$^a$Non-cytoplasmic domain refers to the span of amino acids predicted to be non-cytoplasmic as described in the Examples
$^b$Transmembrane refers to number of transmembrane domains as predicted by a membrane protein topology prediction method TMHMM as described in the Examples.

What is claimed is:

1. An immunogenic composition comprising: at least two isolated polypeptides or immunogenic fragments thereof and an adjuvant, wherein the at least two isolated polypeptides comprise a first polypeptide comprising the amino acid sequence of SEP ID NO: 1 and a second polypeptide comprising the amino acid sequence of SEP ID NO: 9 and the immunogenic fragments thereof comprise at least 30 contiguous amino acid sequences from the amino acid sequence of SEQ ID NO:1 and at least 30 contiguous amino add sequences from the amino acid sequence of SEQ ID NO: 9.

2. The immunogenic composition as in claim 1, further comprising one or more polypeptides having an amino acid sequence selected from the group consisting of SEQ ID NOS: 2-7, 11, 14, 15, 18, 19, 22, 23 and 26.

3. The immunogenic composition as in claim 1, wherein the immunogenic composition consists essentially of five isolated polypeptides and the adjuvant.

4. The immunogenic composition as in claim 1, wherein the immunogenic composition is a vaccine.

5. The immunogenic composition as in claim 1, wherein the adjuvant is Freund's complete adjuvant.

6. A method for treating a filarial disease comprising administering an effective amount of a vaccine comprising the immunogenic composition of claim 1.

7. The method of claim 6, wherein the filarial disease is selected from the group consisting of lymphatic filariasis, river blindness, loiasis and heartworm.

8. The method of claim 6, wherein the subject is a human.

9. The method of claim 6, wherein the filarial disease is heartworm.

10. The method of claim 6, wherein the subject is a dog.

11. The method of claim 6, wherein the vaccine is subcutaneously, intradermally, orally, or nasally administered.

* * * * *